XXXXXXXX

United States Patent
Morsey et al.

(10) Patent No.: US 12,180,288 B2
(45) Date of Patent: Dec. 31, 2024

(54) ANTIBODIES TO CANINE INTERLEUKIN-4 RECEPTOR ALPHA

(71) Applicant: Intervet Inc., Madison, NJ (US)

(72) Inventors: Mohamad Morsey, Omaha, NE (US); Yuanzheng Zhang, Somerset, NJ (US)

(73) Assignee: INTERVET INC., Rahway, NJ (US)

( * ) Notice: Subject to any disclaimer, the term of this patent is extended or adjusted under 35 U.S.C. 154(b) by 487 days.

(21) Appl. No.: 17/081,188

(22) Filed: Oct. 27, 2020

(65) Prior Publication Data

US 2021/0040223 A1  Feb. 11, 2021

Related U.S. Application Data

(62) Division of application No. 15/562,308, filed as application No. PCT/EP2016/057256 on Apr. 1, 2016, now Pat. No. 10,858,437.

(60) Provisional application No. 62/142,108, filed on Apr. 2, 2015, provisional application No. 62/269,486, filed on Dec. 18, 2015, provisional application No. 62/310,250, filed on Mar. 18, 2016.

(51) Int. Cl.
    *C07K 16/28* (2006.01)

(52) U.S. Cl.
    CPC ...... *C07K 16/2866* (2013.01); *C07K 2317/24* (2013.01); *C07K 2317/33* (2013.01); *C07K 2317/34* (2013.01); *C07K 2317/53* (2013.01); *C07K 2317/565* (2013.01); *C07K 2317/71* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| | | | |
|---|---|---|---|
| 5,985,280 A † | 11/1999 | Ritter | |
| 6,716,587 B2 † | 4/2004 | Mosley | |
| 7,208,579 B2 | 4/2007 | Watson et al. | |
| 8,791,242 B2 | 7/2014 | Mattson et al. | |
| 9,505,829 B2 | 11/2016 | Lacy et al. | |
| 2002/0002132 A1 † | 1/2002 | Pluenneke | |
| 2007/0037210 A1 | 2/2007 | Chemtob et al. | |
| 2008/0160035 A1 | 7/2008 | Stevens et al. | |
| 2014/0072583 A1 † | 3/2014 | Ardeleanu | |
| 2014/0356372 A1 | 12/2014 | Stahl et al. | |
| 2015/0017176 A1 | 1/2015 | Kostic et al. | |

FOREIGN PATENT DOCUMENTS

| | | |
|---|---|---|
| JP | 2011508592 A | 3/2011 |
| RU | 2445318 C2 | 3/2012 |
| WO | 2005032399 A2 | 4/2005 |
| WO | 2009081201 A2 | 7/2009 |
| WO | 2010053751 A1 | 5/2010 |
| WO | 2010054667 A1 | 5/2010 |
| WO | 2010070346 A2 | 6/2010 |
| WO | 2012153126 A1 † | 11/2012 |
| WO | 2015091910 A2 | 6/2015 |
| WO | 2016050721 A1 | 9/2015 |
| WO | 2017102920 A1 | 6/2017 |

OTHER PUBLICATIONS

Wu, et al. (Journal of Molecular Biology, 1999. vol. 294, pp. 151-162 (Year: 1999).*
MacCallum, et al. (Journal of Molecular Biology, 1996. vol. 262, pp. 732-774 (Year: 1996).*
Skolnick, et al. (Trends in Biotechnology, 2000. vol. 18, pp. 34-39 (Year: 2000).*
Casset, et al. (Biochemical and Biophysical Research Communications, 2003. vol. 307, pp. 198-205 (Year: 2003).*
Vajdos, et al. (Journal of Molecular Biology, 2002. vol. 320, pp. 415-428 (Year: 2002).*
Al-Lazikani, Standard Conformations for the Canonical Structures of Immunoglobulins, J. Mol. Biol., 1997, 927-948, 273.
Chothia et al, Canonical Structures for the Hypervariable Regions of Immunoglobins, J. Mol. Biol., 1987, 901-917, 196.
Chothia et al., Conformations of immunoglobin hypervariable regions, Nature, 1989, 877-883, 342.
Cobbold, et al., The immunology of companion animals: reagents and therapeutic strategies with potential veterinary and human clinical applications, Immunology Today, 1994, pp. 347-353, 15-18.
Database GenBank: acc. No. U62050.1, Feb. 19, 1997.
Galizzi et al., Molucular cloning of a cDNA encoding the human interleukin 4 receptor, International Immunology, 1990, 669-675, 2(7).
Harskamp et al., Immunology of Atopic Dermatitis: Novel Insights into Mechanisms and Immunomodulatory Therapies, Seminars in Cutaneous Medicine and Surgery, 2013, 132-139, 32.
International Search Report, Sep. 2, 2016, International search report for PCTEP2016057256 mailed on Sep. 2, 2016, 7 pages.
Malajian et al., New pathogenic and therapeutic paradigms in atopic dermatitis, Cytokine, 2015, 311-318, 73.
Minty et al., Interleukin-13 is a new human lymphokine regulating inflammatory and immune responses, Nature, 1993, 248-250, 362.
Mosley et al., The Murine Interleukin-4 Receptor: Molecular Cloning and Characterization of Secreted and Membrane Bound Forms, Cell, 1989, 335-348, 59(2).
Nuttall et al., Canine Atopic Dermatitis—what have we learned?, Veterinary Record, 2013, 201-207, 172(8).
Pakula, Andrew A., Genetic Analysis of Protein Stability and Function, Annu. Rev. Genet., 1989, 289-310, 23.
Rahman et al., The Pathology and Immunology of Atopic Dermatitis, Inflammation & Allergy—Drug Targets, 2011, 486-496, 10.
Rudikoff, S. et al., Single amino acid substitution altering antigen-binding specificity, PNAS, 1982, pp. 1979-1983, 79.

(Continued)

*Primary Examiner* — Michael D Pak
(74) *Attorney, Agent, or Firm* — JONES DAY

(57) ABSTRACT

The present invention discloses antibodies and blocking antibodies to canine IL-4 receptor alpha that have specific sequences and a high binding affinity for canine IL-4 receptor α. The present invention also discloses the use of the antibodies of the present invention in the treatment of atopic dermatitis in dogs. The present invention further discloses unique epitopes that bind to the antibodies to canine IL-4 receptor alpha.

17 Claims, 4 Drawing Sheets

Specification includes a Sequence Listing.

(56) References Cited

OTHER PUBLICATIONS

Sela-Culang, Inbal, The structural basis of antibody-antigen recognition, Frontiers in Immunology, 2013, 1-13, 4:302.
Tang et al., Cloning and characterization of cDNAs encoding four different canine immunoglobulin Y chains, Veterinary Immunology and Immunopathology, 2001, pp. 259-270, 80.
Translation of Yarlin, AA et al., Immunology Principles, Medicine, 1999, pp. 172-174, 5 pages.
Van Der Kaaij et al., Molecular cloning and sequencing of the cDNA for dog interleukin-4, Immunogenetics, 1999, 142-143, 49.
Vatrella, Dupilumab: a novel treatement for asthma, Jornal of Asthma and Allergy, 2014, 123-130, 7.
Yang et al., Canine Interleukin-13: Molecular Cloning of Full-Length cDNA and Expression of Biologically Active Recombinant Protein, Journal of Interferon and Cytokine Research, 2000, 779-785, 20.
Yarlin, AA, Immunology Principles, Medicine, 1999, pp. 172-174.
Yokota et al., Isolation and characterization of a human interleukin cDNA clone, homologous to mouse B-cell stimulatory factor 1, that expresses B-cell- and T-cell-stimulating activities, Proc. Natl. Acad. Sci. USA, 1986, 5894-5898, 83.
Beck, Lisa A. et al., Dupilumab Treatment in Adults with Moderate-to-Severe Atopic Dermatitis, N Engl J Med, 2014, 130-139, 371:2.
Berglund, L et al., The epitope space of the human proteome, Protein Science, 2008, pp. 606-613, 17.
Tahir et al., 2021, "Accurate determination of epitope for antibodies with unknown 3D structures," Mabs, 13(1):e1961349 (10 pages).
Beck et al., "Dupilumab Treatment in Adults with Moderate-to-Severe Atopic Dermatitis," The New England Journal of Medicine (Jul. 10, 2014), vol. 371, No. 2, pp. 130-139.†
Halliwell, et al., "The ACVD task force on canine atopic dermatitis (III): the role of antibodies in canine atopic dermatitis," Veterinary Immunologyand Immunopathology (2001), vol. 81, pp. 159-167.†
Simpson et al., "Treatment of Patients with moderate-to-severe atopic dermatitis with dupilumab (IL-4R MAb): significant improvement in skin disease and pruritus," Clinical & Experimental Allergy (2013), vol. 43, pp. 1428-1472.†
Nuttall et al., "Expression of Th1, Th2 and immunosuppressive cytokine gene transcripts in canine atopic dermatitis," Clin. Exp. Allergy (2002), vol. 32, pp. 789-795.†

\* cited by examiner
† cited by third party

ANTIBODIES TO CANINE INTERLEUKIN-4 RECEPTOR ALPHA

CROSS-REFERENCE TO RELATED APPLICATIONS

This application is divisional application of co-pending U.S. non-provisional patent application Ser. No. 15/562,308, filed on Sep. 27, 2017, which is a national stage entry under 35 U.S.C. § 371 of PCT/EP2016/057256 filed on Apr. 1, 2016, which claims priority to U.S. Provisional Application No. 62/142,108 filed on Apr. 2, 2015; U.S. Provisional Application No. 62/269,486 filed on Dec. 18, 2015; and U.S. Provisional Application No. 62/310,250 filed on Mar. 18, 2016, the contents of all of which are hereby incorporated by reference in their entireties.

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14463-311-999 SUB_SL.txt," was created on Nov. 12, 2024, and is 127,174 bytes in size.

FIELD OF THE INVENTION

The present invention relates to antibodies to canine IL-4 receptor alpha that have specific sequences, a high binding affinity for canine IL-4 receptor alpha, including some that can block the binding of canine IL-4 to canine IL-4 receptor alpha. The present invention further relates to unique epitopes that bind to the antibodies to canine IL-4 receptor alpha. The present invention also relates to use of the antibodies and the epitopes of the present invention in the treatment of atopic dermatitis in dogs.

BACKGROUND OF THE INVENTION

The immune system comprises a network of resident and recirculating specialized cells that function collaboratively to protect the host against infectious diseases and cancer. The ability of the immune system to perform this function depends to a large extent on the biological activities of a group of proteins secreted by leukocytes and collectively referred to as interleukins. Among the well-studied interleukins are two important molecules identified as interleukin-4 (IL-4) and interleukin-13 (IL-13). IL-4 and IL-13 are two closely related proteins that can be secreted by many cell types including CD4+ Th2 cells, natural killer T cells (NKT), macrophages, mast cells, and basophils. IL-4 and IL-13 display many overlapping functions and are critical to the development of T cell-dependent humoral immune responses. Despite their similarities in overall structure, cell sources and biological functions, each of these cytokines mediates certain specialized functions, which has stimulated considerable research aimed at identifying the receptors and the downstream signaling pathways through which these interleukins mediate both their common and unique biological activities.

It is now known that IL-4 binds with high affinity to two receptors i.e., type-I and type-II IL-4 receptors. The type I IL-4 receptor consists of the IL-4 receptor α chain and the common γ C chain, which is also part of the receptor for several other interleukins including IL-2, IL-7, IL-9, and IL-15. The Type II IL-4 receptor consists of the IL-4 receptor α chain and the IL-13 receptor α1 chain. On other hand, IL-13 binds to the type-II IL-4 receptor, and to a unique receptor designated IL-13 receptor α2. The binding of IL-13 to the IL-13 receptor α2 does not transduce a signal and this receptor is also secreted in a soluble form. Accordingly the IL-13 receptor α2 has often been referred to as a decoy receptor.

The genes encoding the IL-4 protein from various species have been cloned and expressed in bacterial and mammalian cells. For example, the cDNA encoding human IL-4 shows that the mature human IL-4 is a secreted polypeptide of 129 amino acids with a predicted molecular weight of 15 Kd [Yokota et al., *Proc Natl Acad Sci USA*. 83(16): 5894-5898 (1986)]. The cDNA encoding the canine IL-4 protein has also been identified and shown to encode a 132 amino acid polypeptide that shares 40% identity with human IL-4 [van der Kaaij et al., *Immunogenetics* 49:142-143 (1999)]. The gene encoding human IL-13 has been cloned and expressed in a variety of host systems [Minty et al., *Nature* 362:248-50 (1993)]. A cDNA encoding human IL-13 shows that the mature IL-13 is a secreted polypeptide with a 12.4 Kd apparent molecular weight. A cDNA encoding canine IL-13 also has been identified [Yang et al., *J. Interferon and Cytokine Research* 20:779-785 (2000)]. The predicted canine IL-13 mature polypeptide consists of 111 amino acids and shares 61.8% identity with human IL-13.

The genes encoding the human and mouse IL-4 receptor α chains have been cloned and expressed in a variety of host systems. For example, the cDNA encoding the human IL-4 receptor α chain has been described by Galizzi et al., [*International Immunology* 2(7):669-675 (1990)] and the cDNA encoding the murine IL-4 receptor α chain has been described by Mosley et al., [*Cell*, 59(2):335-348 (1989)]. The cDNA for human IL-4 receptor α chain encodes for 825 amino acid residues including a 24 amino acid residue signal sequence. Although the murine protein is 15 amino acid residues shorter than the human receptor, both proteins are closely related with an overall sequence identity of 50% at the amino acid level.

Genes encoding equine, canine, and feline IL-4 receptor α chains have also been disclosed [see, U.S. Pat. No. 7,208,579 B2]. In addition, a cDNA predicted to be corresponding to one isoform of canine IL-4 receptor α can be found in Genbank database (SEQ ID NO: 1). The present invention therefore undertook to determine the IL-4 receptor α chain cDNA and to definitively determine its encoded polypeptide sequence.

Although IL-4 and IL-13 are critical cytokines for the development of Th2 immune responses that are required for protection against extracellular pathogens (e.g., tissue or lumen dwelling parasites), both cytokines have been implicated in the pathogenesis of a variety of allergic diseases in humans and animals, including asthma and atopic dermatitis. Asthma is a common respiratory disease in humans. The disease is characterized by lung inflammation, hyper-responsiveness of bronchial airways to external stimuli, and structural modifications of the bronchial wall tissues. The pathophysiology of allergic asthma has been reviewed by Vatrella et al., [*Journal of Asthma and Allergy* 7:123-130 (2014)]. Asthma is sustained by CD4+ Th2 cells which produce large amounts of IL-4 and IL-13 and orchestrate the immune inflammatory response in the allergic airways. Recent progress in understanding the asthmatic response highlights the important roles played by both IL-4 and IL-13 in the disease pathogenesis. For example, both cytokines stimulate immunoglobulin isotype switch in B cells from IgM to IgE, and this allergen-specific IgE contribute to mast cell degranulation and release of inflammatory mediators in the airways. In addition, both IL-4 and IL-13 increase bronchial smooth muscle contraction and stimulate airway recruitment of eosinophils which can also degranulate in response to crosslinking of allergen-bound IgE to its receptor on eosinophils. In addition, IL-13 also stimulates mucus secretion and promotes airway remodeling by stimulating goblet cell hyperplasia, deposition of collagen, and proliferation of airway smooth muscle cells. Thus it is now clear that IL-4 and IL-13 are intimately involved in the pathological changes that lead to expression of asthmatic episodes including bronchial constriction and increased airway hyperactivity.

Atopic dermatitis (AD) is a relapsing pruritic inflammatory skin disease that is characterized by immune system dysregulation and epidermal barrier abnormalities. The pathological and immunological attributes of AD have been the subject of extensive investigations [reviewed in Rahman et al. *Inflammation & Allergy-drug target* 10:486-496 (2011) and Harskamp et al., *Seminar in Cutaneous Medicine and Surgery* 32:132-139 (2013)]. AD is the most common skin disease in man affecting 2-10% of the adult population in the United States and about 25% of children worldwide. In man, AD skin lesions are characterized by infiltrations with Th2 cells, eosinophils, mast cells and dendritic cells. In the acute phase of AD, these lesions display a predominant expression of Th2-type cytokines including IL-4 and IL-13. AD is also characterized by elevated circulating levels of IgE and is positively correlated with IL-4 and IL-13 expression in CD4+ Th2 cells in the skin. Although AD has been classified as a Th2 disease, other T cell subsets such as Th1, Th22 and Th17 might also contribute to disease pathogenesis. Despite the increasing incidence of AD worldwide, treatment options available to patients whose symptoms are not adequately controlled by topical agents are limited to oral corticosteroids, oral cyclosporine and narrow band UVB phototherapy. These therapies are not always effective and their use is associated with a variety of safety effects. Recently, monoclonal antibodies specific to human IL-4 $R_\alpha$ have been developed and some of these antibodies have been tested extensively for their therapeutic utilities in man for treatment of atopic dermatitis [see, e.g, US20150017176 A1].

AD is also a common disease in companion animals, especially dogs, where its prevalence has been estimated to be approximately 10-15% of the canine population. The pathogenesis of AD in dogs and cats [reviewed in Nuttall et al., *Veterinary Records* 172(8):201-207 (2013)] bears significant similarities to that of AD in man including skin infiltration by a variety of immune cells and CD4+ Th2 polarized cytokine milieu including preponderance of IL-4 and IL-13 cytokines. As in humans, current therapies for atopic dermatitis in dogs and cats rely on palliative therapy such as shampoos and moisturizers or symptomatic therapy via the use of oral or systemic corticosteroids and oral cyclosporine. As with human AD, these therapies do not address the underlying mechanism of disease and have significant safety and efficacy issues. Thus, there is an unmet medical need for a safe and effective treatment option for AD in companion animals. Such treatment should preferably interfere with the underlying mechanism of disease.

The citation of any reference herein should not be construed as an admission that such reference is available as "prior art" to the instant application.

SUMMARY OF THE INVENTION

The present invention relates to anti-canine interleukin-4 receptor alpha (IL-4$R_\alpha$) antibodies that have a high binding affinity for canine IL-4$R_\alpha$. In more particular embodiments, the anti-canine interleukin-4 receptor alpha (IL-4$R_\alpha$) antibodies also have the ability to block the binding of canine IL-4 and canine IL-13 to the type-I or type II IL-4 receptors and subsequently inhibit the signaling from both canine IL-4 and IL-13. In particular embodiments such anti-canine IL-4$R_\alpha$ antibodies are murine anti-canine IL-4$R_\alpha$ antibodies. In more particular embodiments the anti-canine IL-4$R_\alpha$ antibodies have a high binding affinity to canine IL-4$R_\alpha$, as well as have the ability to block the binding of canine IL-4 and canine IL-13 to the type-I and type II IL-4 receptors.

Moreover, the present invention relates to the complementary determining regions (CDRs) comprised by these antibodies and the combination of these CDRs (e.g., obtained from murine anti-canine IL-4$R_\alpha$ antibodies) into canine frames to form caninized anti-canine IL-4$R_\alpha$ antibodies. The present invention also relates to use of such antibodies in the treatment of conditions such as atopic dermatitis and/or other adverse conditions due to the downstream effects of the signaling from the binding of canine IL-4 and/or canine IL-13 to the type-I and/or type II IL-4 receptors.

Accordingly, the present invention provides unique sets of CDRs from fourteen (14) exemplified murine anti-canine IL-4$R_\alpha$ antibodies. The 14 exemplified murine anti-canine IL-4$R_\alpha$ antibodies have unique sets of CDRs, i.e., three light chain CDRs: CDR light 1 (CDRL1), CDR light 2 (CDRL2), and CDR light 3 (CDRL3) and three heavy chain CDRs CDR heavy 1 (CDRH1), CDR heavy 2 (CDRH2) and CDR heavy 3 (CDRH3). As detailed below, there is substantial sequence homology within each group of CDRs, and even some redundancy e.g., see, the set of CDRL1s below. Therefore, the present invention not only provides the amino acid sequences of the six CDRs from the 14 exemplified murine anti-canine IL-4$R_\alpha$ antibodies, but further provides conservatively modified variants of these CDRs, as well as variants that comprise (e.g., share) the same canonical structure and/or bind to one or more (e.g., 1 to 4, or more) amino acid residues of canine IL-4$R_\alpha$ that are comprised by an epitope of canine IL-4$R_\alpha$.

Therefore, the present invention provides an antibody or antigen binding fragment thereof that binds IL-4$R_\alpha$ with specificity comprising a light chain complementary determining region 1 (VL CDR1) that comprises the amino acid sequence of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 129, SEQ ID NO: 130, or SEQ ID NO: 131, and/or a light chain complementary determining region 2 (VL CDR2) comprising the amino acid sequence of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132, SEQ ID NO: 133, or SEQ ID NO: 134, and/or a light chain complementary determining region 3 (VL CDR3) comprising the amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 135, SEQ ID NO: 136, SEQ ID NO: 137, SEQ ID NO: 138, or SEQ ID NO: 139, and/or a heavy chain complementary determining region 1 (VH CDR1) in which the CDRH1 comprises the amino acid sequence of SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 140, SEQ ID NO: 141, SEQ ID NO: 142, or SEQ ID NO: 143, and/or a heavy chain complementary determining region 2 (VH CDR2) comprising the amino acid sequence of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 144, SEQ ID NO: 145, SEQ ID NO: 146, SEQ ID NO: 147, or SEQ ID NO: 148 and/or a heavy chain complementary determining region 3 (VH CDR3) comprising the amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 149, SEQ ID NO: 150, SEQ ID NO: 151, SEQ ID NO: 152, or SEQ ID NO: 153. In particular embodiments the antibody is a mammalian antibody. In more particular embodiments the antibody is a caninized antibody.

Accordingly, a caninized antibody of the present invention or antigen binding fragment thereof comprises one or more of the heavy chain complementary determining region 1 (VH CDR1) with an amino acid sequence of SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 140, SEQ ID NO: 141, SEQ ID NO: 142, or SEQ ID NO: 143. In another embodiment, the heavy chain complementary determining region 2 (VH CDR2) comprises an amino acid sequence of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 144, SEQ ID NO: 145, SEQ ID NO: 146, SEQ ID NO: 147, or SEQ ID NO: 148. In still another embodiment the heavy chain complementary determining region 3 (VH CDR3) comprises an amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 149, SEQ ID NO: 150, SEQ ID NO: 151, SEQ ID NO: 152, or SEQ ID NO: 153. In a particular embodiment of this type, the caninized antibody or antigen binding fragment comprises both a VH CDR1 comprising an amino acid sequence of SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 140, SEQ ID NO: 141, SEQ ID NO: 142, or SEQ ID NO: 143 and a VH CDR2 comprising an amino acid sequence of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 144, SEQ ID NO: 145, SEQ ID NO: 146, SEQ ID NO: 147, or SEQ ID NO: 148. In another such embodiment, the caninized antibody or antigen binding fragment comprises both a VH CDR1 comprising an amino acid sequence of SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 140, SEQ ID NO: 141, SEQ ID NO: 142, or SEQ ID NO: 143, and a VH CDR3 comprising an amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100, SEQ ID NO: 149, SEQ ID NO: 150, SEQ ID NO: 151, SEQ ID NO: 152, or SEQ ID NO: 153. In yet another such embodiment, the caninized antibody or antigen binding fragment comprises both a VH CDR2 comprising an amino acid sequence of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 144, SEQ ID NO: 145, SEQ ID NO: 146, SEQ ID NO: 147, or SEQ ID NO: 148 and a VH CDR3 comprising an amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100, SEQ ID NO: 149, SEQ ID NO: 150, SEQ ID NO: 151, SEQ ID NO: 152, or SEQ ID NO: 153. In still another such embodiment, the caninized antibody or antigen binding fragment comprises a VH CDR1 comprising an amino acid sequence of SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 140, SEQ ID NO: 141, SEQ ID NO: 142, or SEQ ID NO: 143, a VH CDR2 comprising an amino acid sequence of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 144, SEQ ID NO: 145, SEQ ID NO: 146, SEQ ID NO: 147, or SEQ ID NO: 148 and a VH CDR3 comprising an amino acid sequence of SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100, SEQ ID NO: 149, SEQ ID NO: 150, SEQ ID NO: 151, SEQ ID NO: 152, or SEQ ID NO: 153.

In particular embodiments, the caninized antibody or antigen binding fragment also comprises a light chain complementary determining region 1 (VL CDR1) comprising an amino acid sequence of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 129, SEQ ID NO: 130, or SEQ ID NO: 131. In related embodiments the light chain complementary determining region 2 (VL CDR2) comprises an amino acid sequence of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132, SEQ ID NO: 133, or SEQ ID NO: 134. In still another embodiment the light chain complementary determining region 3 (VL CDR3) comprises an amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 135, SEQ ID NO: 136, SEQ ID NO: 137, SEQ ID NO: 138, or SEQ ID NO: 139. In a particular embodiment of this type, the caninized antibody or antigen binding fragment comprises both a VL CDR1 comprising an amino acid sequence of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 129, SEQ ID NO: 130, or SEQ ID NO: 131 and a VL CDR2 comprising an amino acid sequence of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132, SEQ ID NO: 133, or SEQ ID NO: 134.

In other such embodiments, the caninized antibody or antigen binding fragment comprises both a VL CDR1 comprising an amino acid sequence of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 129, SEQ ID NO: 130, or SEQ ID NO: 131 and a VL CDR3 comprising an amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 135, SEQ ID NO: 136, SEQ ID NO: 137, SEQ ID NO: 138, or SEQ ID NO: 139. In yet such embodiments, the caninized antibody or antigen binding fragment comprises both a VL CDR2 comprising an amino acid sequence of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO:

63, SEQ ID NO: 64, SEQ ID NO: 132, SEQ ID NO: 133, or SEQ ID NO: 134 and a VL CDR3 comprising an amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 135, SEQ ID NO: 136, SEQ ID NO: 137, SEQ ID NO: 138, or SEQ ID NO: 139.

In still other such embodiments, the caninized antibody or antigen binding fragment comprises a VL CDR1 comprising an amino acid sequence of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 129, SEQ ID NO: 130, or SEQ ID NO: 131, a VL CDR2 comprising an amino acid sequence of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 132, SEQ ID NO: 133, or SEQ ID NO: 134, and a VL CDR3 comprising an amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 135, SEQ ID NO: 136, SEQ ID NO: 137, SEQ ID NO: 138, or SEQ ID NO: 139.

In particular embodiments the caninized anti-canine IL-4R$_\alpha$ antibody comprises complementary determining regions (CDRs) in which the CDRs have canonical structures of: H1-1, H2-3A, and H3-12, respectively for CDR1, CDR2, and CDR3 of the heavy chain, i.e., CDR1 of the heavy chain has the canonical structure class 1, CDR2 of the heavy chain has the canonical structure class 3A, and CDR3 of the heavy chain has the canonical structure class 12. In even more particular embodiments, the CDRs for the corresponding light chains have canonical structures of: L1-1, L2-1, and L3-1, respectively for CDR1, CDR2, and CDR3 of the light chain. In other embodiments the caninized anti-canine IL-4R$_\alpha$ antibody comprises complementary determining regions (CDRs) in which the CDRs have canonical structures of: H1-1, H2-2A, and H3-7, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain. In still other embodiments the caninized anti-canine IL-4R$_\alpha$ antibody further comprises complementary determining regions (CDRs) in which the CDRs have canonical structures of: H1-1, H2-2B, and H3-15, respectively for CDR1, CDR2, and CDR3 of the heavy chain. In even more particular embodiments of this type, the CDRs for the corresponding light chains have canonical structures of: L1-4, L2-1, and L3-1, respectively for CDR1, CDR2, and CDR3 of the light chain. In yet other embodiments the caninized anti-canine IL-4R$_\alpha$ antibody further comprises complementary determining regions (CDRs) in which the CDRs have canonical structures of: H1-1, H2-1, and H3-15, respectively for CDR1, CDR2, and CDR3 of the heavy chain. In even more particular embodiments of this type, the CDRs for the corresponding light chains have canonical structures of: L1-3, L2-1, and L3-1, respectively for CDR1, CDR2, and CDR3 of the light chain. In still other embodiments the caninized anti-canine IL-4R$_\alpha$ antibody further comprises complementary determining regions (CDRs) in which the CDRs have canonical structures of: H1-1, H2-2B, and H3-6, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain.

In yet other embodiments the caninized anti-canine IL-4R$_\alpha$ antibody further comprises complementary determining regions (CDRs) in which the CDRs have canonical structures of: H1-1, H2-2B, and H3-4, respectively for CDR1, CDR2, and CDR3 of the heavy chain. In even more particular embodiments of this type, the CDRs for the corresponding light chains have canonical structures of: L1-6, L2-1, and L3-1, respectively for CDR1, CDR2, and CDR3 of the light chain. In still other embodiments the caninized anti-canine IL-4R$_\alpha$ antibody further comprises complementary determining regions (CDRs) in which the CDRs have canonical structures of: H1-1, H2-1, and H3-13, respectively for CDR1, CDR2, and CDR3 of the heavy chain. In even more particular embodiments of this type, the CDRs for the corresponding light chains have canonical structures of: L1-1, L2-1, and L3-1, respectively for CDR1, CDR2, and CDR3 of the light chain. In yet other embodiments the caninized anti-canine IL-4R$_\alpha$ antibody further comprises complementary determining regions (CDRs) in which the CDRs have canonical structures of: H1-1, H2-2A, and H3-6, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain.

In still other embodiments the caninized anti-canine IL-4R$_\alpha$ antibody further comprises complementary determining regions (CDRs) in which the CDRs have canonical structures of: H1-1, H2-3A, and H3-15 or alternatively H3-13, respectively for CDR1, CDR2, and CDR3 of the heavy chain. In even more particular embodiments of this type, the CDRs for the corresponding light chains have canonical structures of: L1-6, L2-1, and L3-1, respectively for CDR1, CDR2, and CDR3 of the light chain. In yet other embodiments the caninized anti-canine IL-4R$_\alpha$ antibody further comprises complementary determining regions (CDRs) in which the CDRs have canonical structures of: H1-1, H2-2A, and H3-10, respectively for CDR1, CDR2, and CDR3 of the heavy chain. In even more particular embodiments of this type, the CDRs for the corresponding light chains have canonical structures of: L1-6, L2-1, and L3-1, respectively for CDR1, CDR2, and CDR3 of the light chain. In still other embodiments the caninized anti-canine IL-4R$_\alpha$ antibody further comprises complementary determining regions (CDRs) in which the CDRs have canonical structures of: H1-1, H2-3A, and H3-9, respectively for CDR1, CDR2, and CDR3 of the heavy chain. In even more particular embodiments of this type, the CDRs for the corresponding light chains have canonical structures of: L1-3, L2-1, and L3-3, respectively for CDR1, CDR2, and CDR3 of the light chain.

The present invention also provides an isolated caninized antibody or antigen binding fragment thereof that specifically binds IL-4R$_\alpha$ comprising a canine IgG heavy chain and a canine kappa or lambda light chain. In particular embodiments of this type, the canine kappa or lambda light chain that comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3) is obtained from the murine anti-canine IL-4R$_\alpha$ antibodies. Particular embodiments of the caninized antibodies and antigen binding fragments thereof of the present invention bind canine IL-4R$_\alpha$ and/or block the binding of canine IL-4R$_\alpha$ to canine IL-4.

In specific embodiments, the present invention provides an isolated mammalian antibody or antigen binding fragment thereof that binds canine interleukin-4 receptor alpha (IL-4R$_\alpha$) with specificity comprising three light chain complementary determining regions (CDRs): CDR light 1 (CDRL1), CDR light 2 (CDRL2), and CDR light 3 (CDRL3); and three heavy chain CDRs: CDR heavy 1 (CDRH1), CDR heavy 2 (CDRH2) and CDR heavy 3 (CDRH3). In certain embodiments the CDRL1 comprises the amino acid sequence of SEQ ID NO: 47, a variant of SEQ ID NO: 47, a conservatively modified variant of SEQ ID NO: 47, a variant of SEQ ID NO: 47 that comprises the canonical structure class of 1, SEQ ID NO: 48, a variant of SEQ ID NO: 48, a conservatively modified variant of SEQ ID NO: 48, a variant of SEQ ID NO: 48 that comprises the canonical structure class of 2A, SEQ ID NO: 49, a variant of SEQ ID NO: 49, a conservatively modified variant of SEQ ID NO: 49, a variant of SEQ ID NO: 49 that comprises the canonical structure class of 4, SEQ ID NO: 50, a variant of SEQ ID NO: 50, a conservatively modified variant of SEQ ID NO: 50, a variant of SEQ ID NO: 50 that comprises the canonical structure class of 3, SEQ ID NO: 51, a variant of SEQ ID NO: 51, a conservatively modified variant of SEQ ID NO: 51, a variant of SEQ ID NO: 51 that comprises the canonical structure class of 3, SEQ ID NO: 52, a variant of SEQ ID NO: 52, a conservatively modified variant of SEQ ID NO: 52, a variant of SEQ ID NO: 52 that comprises the canonical structure class of 2A, SEQ ID NO: 53, a variant of SEQ ID NO: 53, a conservatively modified variant of SEQ ID NO: 53, a variant of SEQ ID NO: 53 that comprises the canonical structure class of 6, SEQ ID NO: 54, a variant of SEQ ID NO: 54, a conservatively modified variant of SEQ ID NO: 54, a variant of SEQ ID NO: 54 that comprises the canonical structure class of 1, SEQ ID NO: 55, a variant of SEQ ID NO: 55, a conservatively modified variant of SEQ ID NO: 55, a variant of SEQ ID NO: 55 that comprises the canonical structure class of 2A, SEQ ID NO: 129, a variant of SEQ ID NO: 129, a conservatively modified variant of SEQ ID NO: 129, a variant of SEQ ID NO: 129 that comprises the canonical structure class of 6, SEQ ID NO: 130, a variant of SEQ ID NO: 130, a conservatively modified variant of SEQ ID NO: 130, a variant of SEQ ID NO: 130 that comprises the canonical structure class of 6, SEQ ID NO: 131, a variant of SEQ ID NO: 131, a conservatively modified variant of SEQ ID NO: 131, or a variant of SEQ ID NO: 131 that comprises the canonical structure class of 3.

The corresponding CDRL2 comprises the amino acid sequence of SEQ ID NO: 56, a variant of SEQ ID NO: 56, a conservatively modified variant of SEQ ID NO: 56, a variant of SEQ ID NO: 56 that comprises the canonical structure class of 1, SEQ ID NO: 57, a variant of SEQ ID NO: 57, a conservatively modified variant of SEQ ID NO: 57, a variant of SEQ ID NO: 57 that comprises the canonical structure class of 1, SEQ ID NO: 58, a variant of SEQ ID NO: 58, a conservatively modified variant of SEQ ID NO: 58, a variant of SEQ ID NO: 58 that comprises the canonical structure class of 1, SEQ ID NO: 59, a variant of SEQ ID NO: 59, a conservatively modified variant of SEQ ID NO: 59, a variant of SEQ ID NO: 59 that comprises the canonical structure class of 1, SEQ ID NO: 60, a variant of SEQ ID NO: 60, a conservatively modified variant of SEQ ID NO: 60, a variant of SEQ ID NO: 60 that comprises the canonical structure class of 1, SEQ ID NO: 61, a variant of SEQ ID NO: 61, a conservatively modified variant of SEQ ID NO: 61, a variant of SEQ ID NO: 61 that comprises the canonical structure class of 1, SEQ ID NO: 62, a variant of SEQ ID NO: 62, a conservatively modified variant of SEQ ID NO: 62, a variant of SEQ ID NO: 62 that comprises the canonical structure class of 1, SEQ ID NO: 63, a variant of SEQ ID NO: 63, a conservatively modified variant of SEQ ID NO: 63, a variant of SEQ ID NO: 63 that comprises the canonical structure class of 1, SEQ ID NO: 64, a variant of SEQ ID NO: 64, a conservatively modified variant of SEQ ID NO: 64, or a variant of SEQ ID NO: 64 that comprises the canonical structure class of 1, SEQ ID NO: 132, a variant of SEQ ID NO: 132, a conservatively modified variant of SEQ ID NO: 132, a variant of SEQ ID NO: 132 that comprises the canonical structure class of 1, SEQ ID NO: 133, a variant of SEQ ID NO: 133, a conservatively modified variant of SEQ ID NO: 133, a variant of SEQ ID NO: 133 that comprises the canonical structure class of 1, SEQ ID NO: 134, a variant of SEQ ID NO: 134, a conservatively modified variant of SEQ ID NO: 134, or a variant of SEQ ID NO: 134 that comprises the canonical structure class of 1.

The corresponding CDRL3 comprises the amino acid sequence of SEQ ID NO: 65, a variant of SEQ ID NO: 65, a conservatively modified variant of SEQ ID NO: 65, a variant of SEQ ID NO: 65 that comprises the canonical structure class of 1, SEQ ID NO: 66, a variant of SEQ ID NO: 66, a conservatively modified variant of SEQ ID NO: 66, a variant of SEQ ID NO: 66 that comprises the canonical structure class of 1, SEQ ID NO: 67, a variant of SEQ ID NO: 67, a conservatively modified variant of SEQ ID NO: 67, a variant of SEQ ID NO: 67 that comprises the canonical structure class of 1, SEQ ID NO: 68, a variant of SEQ ID NO: 68, a conservatively modified variant of SEQ ID NO: 68, a variant of SEQ ID NO: 68 that comprises the canonical structure class of 1, SEQ ID NO: 69, a variant of SEQ ID NO: 69, a conservatively modified variant of SEQ ID NO: 69, a variant of SEQ ID NO: 69 that comprises the canonical structure class of 1, SEQ ID NO: 70, a variant of SEQ ID NO: 70, a conservatively modified variant of SEQ ID NO: 70, a variant of SEQ ID NO: 70 that comprises the canonical structure class of 1, SEQ ID NO: 71, a variant of SEQ ID NO: 71, a conservatively modified variant of SEQ ID NO: 71, a variant of SEQ ID NO: 71 that comprises the canonical structure class of 1, SEQ ID NO: 72, a variant of SEQ ID NO: 72, a conservatively modified variant of SEQ ID NO: 72, a variant of SEQ ID NO: 72 that comprises the canonical structure class of 1, SEQ ID NO: 73, a variant of SEQ ID NO: 73, a conservatively modified variant of SEQ ID NO: 73, a variant of SEQ ID NO: 73 that comprises the canonical structure class of 1, SEQ ID NO: 135, a variant of SEQ ID NO: 135, a conservatively modified variant of SEQ ID NO: 135, a variant of SEQ ID NO: 135 that comprises the canonical structure class of 1, SEQ ID NO: 136, a variant of SEQ ID NO: 136, a conservatively modified variant of SEQ ID NO: 136, a variant of SEQ ID NO: 136 that comprises the canonical structure class of 1, SEQ ID NO: 137, a variant of SEQ ID NO: 137, a conservatively modified variant of SEQ ID NO: 137, a variant of SEQ ID NO: 137 that comprises the canonical structure class of 1, SEQ ID NO: 138, a variant of SEQ ID NO: 138, a conservatively modified variant of SEQ ID NO: 138, a variant of SEQ ID NO: 138 that comprises the canonical structure class of 3, SEQ ID NO: 139, a variant of SEQ ID NO: 139, a conservatively modified variant of SEQ ID NO: 139, or a variant of SEQ ID NO: 139 that comprises the canonical structure class of 1.

The corresponding CDRH1 comprises the amino acid sequence of SEQ ID NO: 74, a variant of SEQ ID NO: 74, a conservatively modified variant of SEQ ID NO: 74, a variant of SEQ ID NO: 74 that comprises the canonical structure class of 1, SEQ ID NO: 75, a variant of SEQ ID NO: 75, a conservatively modified variant of SEQ ID NO: 75, a variant of SEQ ID NO: 75 that comprises the canonical structure class of 1, SEQ ID NO: 76, a variant of SEQ ID NO: 76, a conservatively modified variant of SEQ ID NO: 76, or a variant of SEQ ID NO: 76 that comprises the canonical structure class of 1, SEQ ID NO: 77, a variant of SEQ ID NO: 77, a conservatively modified variant of SEQ ID NO: 77, or a variant of SEQ ID NO: 77 that comprises the canonical structure class of 1, SEQ ID NO: 78, a variant of SEQ ID NO: 78, a conservatively modified variant of SEQ ID NO: 78, a variant of SEQ ID NO: 78 that comprises the canonical structure class of 1, SEQ ID NO: 79, a variant of SEQ ID NO: 79, a conservatively modified variant of SEQ ID NO: 79, a variant of SEQ ID NO: 79 that comprises the canonical structure class of 1, SEQ ID NO: 80, a variant of SEQ ID NO: 80, a conservatively modified variant of SEQ ID NO: 80, a variant of SEQ ID NO: 80 that comprises the canonical structure class of 1, SEQ ID NO: 81, a variant of SEQ ID NO: 81, a conservatively modified variant of SEQ ID NO: 81, a variant of SEQ ID NO: 81 that comprises the canonical structure class of 1, SEQ ID NO: 82, a variant of SEQ ID NO: 82, a conservatively modified variant of SEQ ID NO: 82, or a variant of SEQ ID NO: 82 that comprises the canonical structure class of 1, SEQ ID NO: 140, a variant of SEQ ID NO: 140, a conservatively modified variant of SEQ ID NO: 140, a variant of SEQ ID NO: 140 that comprises the canonical structure class of 1, SEQ ID NO: 141, a variant of SEQ ID NO: 141, a conservatively modified variant of SEQ ID NO: 141, a variant of SEQ ID NO: 141 that comprises the canonical structure class of 1, SEQ ID NO: 142, a variant of SEQ ID NO: 142, a conservatively modified variant of SEQ ID NO: 142, a variant of SEQ ID NO: 142 that comprises the canonical structure class of 1, SEQ ID NO: 143, a variant of SEQ ID NO: 143, a conservatively modified variant of SEQ ID NO: 143, or a variant of SEQ ID NO: 143 that comprises the canonical structure class of 1.

The corresponding CDRH2 comprises the amino acid sequence of SEQ ID NO: 83, a variant of SEQ ID NO: 83, a conservatively modified variant of SEQ ID NO: 83, a variant of SEQ ID NO: 83 that comprises the canonical structure class of 3A, SEQ ID NO: 84, a variant of SEQ ID NO: 84, a conservatively modified variant of SEQ ID NO: 84, a variant of SEQ ID NO: 84 that comprises the canonical structure class of 2A, SEQ ID NO: 85, a variant of SEQ ID NO: 85, a conservatively modified variant of SEQ ID NO: 85, or a variant of SEQ ID NO: 85 that comprises the canonical structure class of 2B, SEQ ID NO: 86, a variant of SEQ ID NO: 86, a conservatively modified variant of SEQ ID NO: 86, SEQ ID NO: 87, a variant of SEQ ID NO: 87, a conservatively modified variant of SEQ ID NO: 87, a variant of SEQ ID NO: 87 that comprises the canonical structure class of 1, SEQ ID NO: 88, a variant of SEQ ID NO: 88, a conservatively modified variant of SEQ ID NO: 88, a variant of SEQ ID NO: 88 that comprises the canonical structure class of 2B, SEQ ID NO: 89, a variant of SEQ ID NO: 89, a conservatively modified variant of SEQ ID NO: 89, a variant of SEQ ID NO: 89 that comprises the canonical structure class of 2B, SEQ ID NO: 90, a variant of SEQ ID NO: 90, a conservatively modified variant of SEQ ID NO: 90, a variant of SEQ ID NO: 90 that comprises the canonical structure class of 1, SEQ ID NO: 91, a variant of SEQ ID NO: 91, a conservatively modified variant of SEQ ID NO: 91, a variant of SEQ ID NO: 91 that comprises the canonical structure class of 2A, SEQ ID NO: 144, a variant of SEQ ID NO: 144, a conservatively modified variant of SEQ ID NO: 144, a variant of SEQ ID NO: 144 that comprises the canonical structure class of 3A, SEQ ID NO: 145, a variant of SEQ ID NO: 145, a conservatively modified variant of SEQ ID NO: 145, a variant of SEQ ID NO: 145 that comprises the canonical structure class of 2A, SEQ ID NO: 146, a variant of SEQ ID NO: 146, a conservatively modified variant of SEQ ID NO: 146, a variant of SEQ ID NO: 146 that comprises the canonical structure class of 3A, SEQ ID NO: 147, a variant of SEQ ID NO: 147, a conservatively modified variant of SEQ ID NO: 147, a variant of SEQ ID NO: 147 that comprises the canonical structure class of 3A, SEQ ID NO: 148, a variant of SEQ ID NO: 148, a conservatively modified variant of SEQ ID NO: 148, or a variant of SEQ ID NO: 148 that comprises the canonical structure class of 3A.

The corresponding CDRH3 comprises the amino acid sequence of SEQ ID NO: 92, a variant of SEQ ID NO: 92, a conservatively modified variant of SEQ ID NO: 92, a variant of SEQ ID NO: 92 that comprises the canonical structure class of 12, SEQ ID NO: 93, a variant of SEQ ID NO: 93, a conservatively modified variant of SEQ ID NO: 93, a variant of SEQ ID NO: 93 that comprises the canonical structure class of 7, SEQ ID NO: 94, a variant of SEQ ID NO: 94, a conservatively modified variant of SEQ ID NO: 94, or a variant of SEQ ID NO: 94 that comprises the canonical structure class of 15, SEQ ID NO: 95, a variant of SEQ ID NO: 95, a conservatively modified variant of SEQ ID NO: 95, or a variant of SEQ ID NO: 95 that comprises the canonical structure class of 11, SEQ ID NO: 96, a variant of SEQ ID NO: 96, a conservatively modified variant of SEQ ID NO: 96, a variant of SEQ ID NO: 96 that comprises the canonical structure class of 15, SEQ ID NO: 97, a variant of SEQ ID NO: 97, a conservatively modified variant of SEQ ID NO: 97, a variant of SEQ ID NO: 97 that comprises the canonical structure class of 6, SEQ ID NO: 98, a variant of SEQ ID NO: 98, a conservatively modified variant of SEQ ID NO: 98, a variant of SEQ ID NO: 98 that comprises the canonical structure class of 4, SEQ ID NO: 99, a variant of SEQ ID NO: 99, a conservatively modified variant of SEQ ID NO: 99, a variant of SEQ ID NO: 99 that comprises the canonical structure class of 13, SEQ ID NO: 100, a variant of SEQ ID NO: 100, a conservatively modified variant of SEQ ID NO: 100, or a variant of SEQ ID NO: 100 that comprises the canonical structure class of 6, SEQ ID NO: 149, a variant of SEQ ID NO: 149, a conservatively modified variant of SEQ ID NO: 149, a variant of SEQ ID NO: 149 that comprises the canonical structure class of 15, SEQ ID NO: 150, a variant of SEQ ID NO: 150, a conservatively modified variant of SEQ ID NO: 150, a variant of SEQ ID NO: 150 that comprises the canonical structure class of 10, SEQ ID NO: 151, a variant of SEQ ID NO: 151, a conservatively modified variant of SEQ ID NO: 151, a variant of SEQ ID NO: 151 that comprises the canonical structure class of 15, SEQ ID NO: 152, a variant of SEQ ID NO: 152, a conservatively modified variant of SEQ ID NO: 152, a variant of SEQ ID NO: 152 that comprises the canonical structure class of 9, SEQ ID NO: 153, a variant of SEQ ID NO: 153, a conservatively modified variant of SEQ ID NO: 153, or a variant of SEQ ID NO: 153 that comprises the canonical structure class of 13.

In particular embodiments the mammalian antibodies (including chimeric mammalian antibodies) and/or antigen binding fragments thereof of the present invention bind the canine interleukin-4 receptor alpha (IL-4R$_\alpha$) and/or block the binding of canine IL-4R$_\alpha$ to canine IL-4 and/or canine IL-13. In related embodiments the mammalian antibodies and/or antigen binding fragments thereof of the present invention block the binding of canine IL-4 and/or canine IL-13 to the IL-4 Type I receptor and/or the IL-4 Type II receptor. In particular embodiments the mammalian antibodies (whether isolated or not) are caninized antibodies.

Accordingly, in certain embodiments of mammalian antibodies (including caninized antibodies) the CDRL1 comprises the amino acid sequence of SEQ ID NO: 47, a variant of SEQ ID NO: 47, a conservatively modified variant of SEQ ID NO: 47, or a variant of SEQ ID NO: 47 that comprises the canonical structure class of 1; the CDRL2 comprises the amino acid sequence of SEQ ID NO: 56, a variant of SEQ ID NO: 56, a conservatively modified variant of SEQ ID NO: 56, or a variant of SEQ ID NO: 56 that comprises the canonical structure class of 1; the CDRL3 comprises the amino acid sequence of SEQ ID NO: 65, a variant of SEQ ID NO: 65, a conservatively modified variant of SEQ ID NO: 65, or a variant of SEQ ID NO: 65 that comprises the canonical structure class of 1, the CDRH1 comprises the amino acid sequence of SEQ ID NO: 74, a variant of SEQ ID NO: 74, a conservatively modified variant of SEQ ID NO: 74, or a variant of SEQ ID NO: 74 that comprises the canonical structure class of 1; the CDRH2 comprises the amino acid sequence of SEQ ID NO: 83, a variant of SEQ ID NO: 83, a conservatively modified variant of SEQ ID NO: 83, and a variant of SEQ ID NO: 83 that comprises the canonical structure class of 3A, the CDRH3 comprises the amino acid sequence of SEQ ID NO: 92, a variant of SEQ ID NO: 92, a conservatively modified variant of SEQ ID NO: 92, or a variant of SEQ ID NO: 92 that comprises the canonical structure class of 12.

In yet other embodiments of mammalian antibodies (including caninized antibodies) the CDRL1 comprises the amino acid sequence of SEQ ID NO: 48, a variant of SEQ ID NO: 48, a conservatively modified variant of SEQ ID NO: 48, or a variant of SEQ ID NO: 48 that comprises the canonical structure class of 2A; the CDRL2 comprises the amino acid sequence of SEQ ID NO: 57, a variant of SEQ ID NO: 57, a conservatively modified variant of SEQ ID NO: 57, or a variant of SEQ ID NO: 57 that comprises the canonical structure class of 1; the CDRL3 comprises the amino acid sequence of SEQ ID NO: 66, a variant of SEQ ID NO: 66, a conservatively modified variant of SEQ ID NO: 66, or a variant of SEQ ID NO: 66 that comprises the canonical structure class of 1, the CDRH1 comprises the amino acid sequence of SEQ ID NO: 75, a variant of SEQ ID NO: 75, a conservatively modified variant of SEQ ID NO: 75, or a variant of SEQ ID NO: 75 that comprises the canonical structure class of 1; the CDRH2 comprises the amino acid sequence of SEQ ID NO: 84, a variant of SEQ ID NO: 84, a conservatively modified variant of SEQ ID NO: 84, and a variant of SEQ ID NO: 84 that comprises the canonical structure class of 2A, the CDRH3 comprises the amino acid sequence of SEQ ID NO: 93, a variant of SEQ ID NO: 93, a conservatively modified variant of SEQ ID NO: 93, or a variant of SEQ ID NO: 93 that comprises the canonical structure class of 7.

In still other embodiments of mammalian antibodies (including caninized antibodies) the CDRL1 comprises the amino acid sequence of SEQ ID NO: 49, a variant of SEQ ID NO: 49, a conservatively modified variant of SEQ ID NO: 49, or a variant of SEQ ID NO: 49 that comprises the canonical structure class of 4; the CDRL2 comprises the amino acid sequence of SEQ ID NO: 58, a variant of SEQ ID NO: 58, a conservatively modified variant of SEQ ID NO: 58, or a variant of SEQ ID NO: 58 that comprises the canonical structure class of 4; the CDRL3 comprises the amino acid sequence of SEQ ID NO: 67, a variant of SEQ ID NO: 67, a conservatively modified variant of SEQ ID NO: 67, or a variant of SEQ ID NO: 67 that comprises the canonical structure class of 1, the CDRH1 comprises the amino acid sequence of SEQ ID NO: 76, a variant of SEQ ID NO: 76, a conservatively modified variant of SEQ ID NO: 76, or a variant of SEQ ID NO: 76 that comprises the canonical structure class of 1; the CDRH2 comprises the amino acid sequence of SEQ ID NO: 85, a variant of SEQ ID NO: 85, a conservatively modified variant of SEQ ID NO: 85, and a variant of SEQ ID NO: 85 that comprises the canonical structure class of 2B, the CDRH3 comprises the amino acid sequence of SEQ ID NO: 94, a variant of SEQ ID NO: 94, a conservatively modified variant of SEQ ID NO: 94, or a variant of SEQ ID NO: 94 that comprises the canonical structure class of 15.

In yet other embodiments of mammalian antibodies (including caninized antibodies) the CDRL1 comprises the amino acid sequence of SEQ ID NO: 51, a variant of SEQ ID NO: 51, a conservatively modified variant of SEQ ID NO: 51, or a variant of SEQ ID NO: 51 that comprises the canonical structure class of 3; the CDRL2 comprises the amino acid sequence of SEQ ID NO: 60, a variant of SEQ ID NO: 60, a conservatively modified variant of SEQ ID NO: 60, or a variant of SEQ ID NO: 60 that comprises the canonical structure class of 1; the CDRL3 comprises the amino acid sequence of SEQ ID NO: 69, a variant of SEQ ID NO: 69, a conservatively modified variant of SEQ ID NO: 69, or a variant of SEQ ID NO: 69 that comprises the canonical structure class of 1, the CDRH1 comprises the amino acid sequence of SEQ ID NO: 78, a variant of SEQ ID NO: 78, a conservatively modified variant of SEQ ID NO: 78, or a variant of SEQ ID NO: 78 that comprises the canonical structure class of 1; the CDRH2 comprises the amino acid sequence of SEQ ID NO: 87, a variant of SEQ ID NO: 87, a conservatively modified variant of SEQ ID NO: 87, and a variant of SEQ ID NO: 87 that comprises the canonical structure class of 1, the CDRH3 comprises the amino acid sequence of SEQ ID NO: 96, a variant of SEQ ID NO: 96, a conservatively modified variant of SEQ ID NO: 96, or a variant of SEQ ID NO: 96 that comprises the canonical structure class of 15.

In still other embodiments of mammalian antibodies (including caninized antibodies) the CDRL1 comprises the amino acid sequence of SEQ ID NO: 52, a variant of SEQ ID NO: 52, a conservatively modified variant of SEQ ID NO: 52, or a variant of SEQ ID NO: 52 that comprises the canonical structure class of 2A; the CDRL2 comprises the amino acid sequence of SEQ ID NO: 61, a variant of SEQ ID NO: 61, a conservatively modified variant of SEQ ID NO: 61, or a variant of SEQ ID NO: 61 that comprises the canonical structure class of 1; the CDRL3 comprises the amino acid sequence of SEQ ID NO: 70, a variant of SEQ ID NO: 70, a conservatively modified variant of SEQ ID NO: 70, or a variant of SEQ ID NO: 70 that comprises the canonical structure class of 1, the CDRH1 comprises the amino acid sequence of SEQ ID NO: 79, a variant of SEQ ID NO: 79, a conservatively modified variant of SEQ ID NO: 79, or a variant of SEQ ID NO: 79 that comprises the canonical structure class of 1; the CDRH2 comprises the amino acid sequence of SEQ ID NO: 88, a variant of SEQ ID NO: 88, a conservatively modified variant of SEQ ID NO: 88, and a variant of SEQ ID NO: 88 that comprises the canonical structure class of 2B, the CDRH3 comprises the amino acid sequence of SEQ ID NO: 97, a variant of SEQ ID NO: 97, a conservatively modified variant of SEQ ID NO: 97, or a variant of SEQ ID NO: 97 that comprises the canonical structure class of 6.

In yet other embodiments of mammalian antibodies (including caninized antibodies) the CDRL1 comprises the amino acid sequence of SEQ ID NO: 53, a variant of SEQ ID NO: 53, a conservatively modified variant of SEQ ID NO: 53, or a variant of SEQ ID NO: 53 that comprises the canonical structure class of 6; the CDRL2 comprises the amino acid sequence of SEQ ID NO: 62, a variant of SEQ ID NO: 62, a conservatively modified variant of SEQ ID NO: 62, or a variant of SEQ ID NO: 62 that comprises the canonical structure class of 1; the CDRL3 comprises the amino acid sequence of SEQ ID NO: 71, a variant of SEQ ID NO: 71, a conservatively modified variant of SEQ ID NO: 71, or a variant of SEQ ID NO: 71 that comprises the canonical structure class of 1, the CDRH1 comprises the amino acid sequence of SEQ ID NO: 80, a variant of SEQ ID NO: 80, a conservatively modified variant of SEQ ID NO: 80, or a variant of SEQ ID NO: 80 that comprises the canonical structure class of 1; the CDRH2 comprises the amino acid sequence of SEQ ID NO: 89, a variant of SEQ ID NO: 89, a conservatively modified variant of SEQ ID NO: 89, and a variant of SEQ ID NO: 89 that comprises the canonical structure class of 2B, the CDRH3 comprises the amino acid sequence of SEQ ID NO: 98, a variant of SEQ ID NO: 98, a conservatively modified variant of SEQ ID NO: 98, or a variant of SEQ ID NO: 98 that comprises the canonical structure class of 4.

In still other embodiments of mammalian antibodies (including caninized antibodies) the CDRL1 comprises the amino acid sequence of SEQ ID NO: 54, a variant of SEQ ID NO: 54, a conservatively modified variant of SEQ ID NO: 54, or a variant of SEQ ID NO: 54 that comprises the canonical structure class of 1; the CDRL2 comprises the amino acid sequence of SEQ ID NO: 63, a variant of SEQ ID NO: 63, a conservatively modified variant of SEQ ID NO: 63, or a variant of SEQ ID NO: 63 that comprises the canonical structure class of 1; the CDRL3 comprises the amino acid sequence of SEQ ID NO: 72, a variant of SEQ ID NO: 72, a conservatively modified variant of SEQ ID NO: 72, or a variant of SEQ ID NO: 72 that comprises the canonical structure class of 1, the CDRH1 comprises the amino acid sequence of SEQ ID NO: 81, a variant of SEQ ID NO: 81, a conservatively modified variant of SEQ ID NO: 81, or a variant of SEQ ID NO: 81 that comprises the canonical structure class of 1; the CDRH2 comprises the amino acid sequence of SEQ ID NO: 90, a variant of SEQ ID NO: 90, a conservatively modified variant of SEQ ID NO: 90, and a variant of SEQ ID NO: 90 that comprises the canonical structure class of 1, the CDRH3 comprises the amino acid sequence of SEQ ID NO: 99, a variant of SEQ ID NO: 99, a conservatively modified variant of SEQ ID NO: 99, or a variant of SEQ ID NO: 99 that comprises the canonical structure class of 13. In particular embodiments of this type, when the antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 157, or SEQ ID NO: 158, or within both SEQ ID NO: 157 and SEQ ID NO: 158.

In yet other embodiments of mammalian antibodies (including caninized antibodies) the CDRL1 comprises the amino acid sequence of SEQ ID NO: 55, a variant of SEQ ID NO: 55, a conservatively modified variant of SEQ ID NO: 55, or a variant of SEQ ID NO: 55 that comprises the canonical structure class of 2A; the CDRL2 comprises the amino acid sequence of SEQ ID NO: 64, a variant of SEQ ID NO: 64, a conservatively modified variant of SEQ ID NO: 64, or a variant of SEQ ID NO: 64 that comprises the canonical structure class of 1; the CDRL3 comprises the amino acid sequence of SEQ ID NO: 73, a variant of SEQ ID NO: 73, a conservatively modified variant of SEQ ID NO: 73, or a variant of SEQ ID NO: 73 that comprises the canonical structure class of 1, the CDRH1 comprises the amino acid sequence of SEQ ID NO: 82, a variant of SEQ ID NO: 82, a conservatively modified variant of SEQ ID NO: 82, or a variant of SEQ ID NO: 82 that comprises the canonical structure class of 1; the CDRH2 comprises the amino acid sequence of SEQ ID NO: 91, a variant of SEQ ID NO: 91, a conservatively modified variant of SEQ ID NO: 91, and a variant of SEQ ID NO: 91 that comprises the canonical structure class of 2A, the CDRH3 comprises the amino acid sequence of SEQ ID NO: 100, a variant of SEQ ID NO: 100, a conservatively modified variant of SEQ ID NO: 100, or a variant of SEQ ID NO: 100 that comprises the canonical structure class of 6.

In still other embodiments of mammalian antibodies (including caninized antibodies) the CDRL1 comprises the amino acid sequence of SEQ ID NO: 129, a variant of SEQ ID NO: 129, a conservatively modified variant of SEQ ID NO: 129, or a variant of SEQ ID NO: 129 that comprises the canonical structure class of 6; the CDRL2 comprises the amino acid sequence of SEQ ID NO: 132, a variant of SEQ ID NO: 132, a conservatively modified variant of SEQ ID NO: 132, or a variant of SEQ ID NO: 132 that comprises the canonical structure class of 1; the CDRL3 comprises the amino acid sequence of SEQ ID NO: 135, a variant of SEQ ID NO: 135, a conservatively modified variant of SEQ ID NO: 135, or a variant of SEQ ID NO: 135 that comprises the canonical structure class of 1, the CDRH1 comprises the amino acid sequence of SEQ ID NO: 140, a variant of SEQ ID NO: 140, a conservatively modified variant of SEQ ID NO: 140, or a variant of SEQ ID NO: 140 that comprises the canonical structure class of 1; the CDRH2 comprises the amino acid sequence of SEQ ID NO: 144, a variant of SEQ ID NO: 144, a conservatively modified variant of SEQ ID NO: 144, and a variant of SEQ ID NO: 144 that comprises the canonical structure class of 3A, the CDRH3 comprises the amino acid sequence of SEQ ID NO: 149, a variant of SEQ ID NO: 149, a conservatively modified variant of SEQ ID NO: 149, or a variant of SEQ ID NO: 149 that comprises the canonical structure class of 15. In particular embodiments of this type, when the antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 127, or SEQ ID NO: 128, or within both SEQ ID NO: 127 and SEQ ID NO: 128.

In yet other embodiments of mammalian antibodies (including caninized antibodies) the CDRL1 comprises the amino acid sequence of SEQ ID NO: 130, a variant of SEQ ID NO: 130, a conservatively modified variant of SEQ ID NO: 130, or a variant of SEQ ID NO: 130 that comprises the canonical structure class of 6; the CDRL2 comprises the amino acid sequence of SEQ ID NO: 133, a variant of SEQ ID NO: 133, a conservatively modified variant of SEQ ID NO: 133, or a variant of SEQ ID NO: 133 that comprises the canonical structure class of 1; the CDRL3 comprises the amino acid sequence of SEQ ID NO: 136, a variant of SEQ ID NO: 136, a conservatively modified variant of SEQ ID NO: 136, or a variant of SEQ ID NO: 136 that comprises the canonical structure class of 1, the CDRH1 comprises the amino acid sequence of SEQ ID NO: 141, a variant of SEQ ID NO: 141, a conservatively modified variant of SEQ ID NO: 141, or a variant of SEQ ID NO: 141 that comprises the canonical structure class of 1; the CDRH2 comprises the amino acid sequence of SEQ ID NO: 145, a variant of SEQ ID NO: 145, a conservatively modified variant of SEQ ID NO: 145, and a variant of SEQ ID NO: 145 that comprises the canonical structure class of 2A, the CDRH3 comprises the amino acid sequence of SEQ ID NO: 150, a variant of SEQ ID NO: 150, a conservatively modified variant of SEQ ID NO: 150, or a variant of SEQ ID NO: 150 that comprises the canonical structure class of 10. In particular embodiments of this type, when the antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 158, or SEQ ID NO: 162, or within both SEQ ID NO: 158 and SEQ ID NO: 162.

In still other embodiments of mammalian antibodies (including caninized antibodies) the CDRL1 comprises the amino acid sequence of SEQ ID NO: 129, a variant of SEQ ID NO: 129, a conservatively modified variant of SEQ ID NO: 129, or a variant of SEQ ID NO: 129 that comprises the canonical structure class of 6; the CDRL2 comprises the amino acid sequence of SEQ ID NO: 134, a variant of SEQ ID NO: 134, a conservatively modified variant of SEQ ID NO: 134, or a variant of SEQ ID NO: 134 that comprises the canonical structure class of 1; the CDRL3 comprises the amino acid sequence of SEQ ID NO: 137, a variant of SEQ ID NO: 137, a conservatively modified variant of SEQ ID NO: 137, or a variant of SEQ ID NO: 137 that comprises the canonical structure class of 1, the CDRH1 comprises the amino acid sequence of SEQ ID NO: 140, a variant of SEQ ID NO: 140, a conservatively modified variant of SEQ ID NO: 140, or a variant of SEQ ID NO: 140 that comprises the canonical structure class of 1; the CDRH2 comprises the amino acid sequence of SEQ ID NO: 146, a variant of SEQ ID NO: 146, a conservatively modified variant of SEQ ID NO: 146, and a variant of SEQ ID NO: 146 that comprises the canonical structure class of 3A, the CDRH3 comprises the amino acid sequence of SEQ ID NO: 151, a variant of SEQ ID NO: 151, a conservatively modified variant of SEQ ID NO: 151, or a variant of SEQ ID NO: 151 that comprises the canonical structure class of 15. In particular embodiments of this type, when the antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 125 or SEQ ID NO: 126, or within both SEQ ID NO: 125 and SEQ ID NO: 126.

In yet other embodiments of mammalian antibodies (including caninized antibodies) the CDRL1 comprises the amino acid sequence of SEQ ID NO: 131, a variant of SEQ ID NO: 131, a conservatively modified variant of SEQ ID NO: 131, or a variant of SEQ ID NO: 131 that comprises the canonical structure class of 3; the CDRL2 comprises the amino acid sequence of SEQ ID NO: 60, a variant of SEQ ID NO: 60, a conservatively modified variant of SEQ ID NO: 60, or a variant of SEQ ID NO: 60 that comprises the canonical structure class of 1; the CDRL3 comprises the amino acid sequence of SEQ ID NO: 138, a variant of SEQ ID NO: 138, a conservatively modified variant of SEQ ID NO: 1385, or a variant of SEQ ID NO: 138 that comprises the canonical structure class of 3, the CDRH1 comprises the amino acid sequence of SEQ ID NO: 142, a variant of SEQ ID NO: 142, a conservatively modified variant of SEQ ID NO: 142, or a variant of SEQ ID NO: 142 that comprises the canonical structure class of 1; the CDRH2 comprises the amino acid sequence of SEQ ID NO: 147, a variant of SEQ ID NO: 147, a conservatively modified variant of SEQ ID NO: 147, and a variant of SEQ ID NO: 147 that comprises the canonical structure class of 3A, the CDRH3 comprises the amino acid sequence of SEQ ID NO: 152, a variant of SEQ ID NO: 152, a conservatively modified variant of SEQ ID NO: 152, or a variant of SEQ ID NO: 152 that comprises the canonical structure class of 9. In particular embodiments of this type, when the antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 154, or SEQ ID NO: 155, or SEQ ID NO: 156, or any combination thereof.

In still other embodiments of mammalian antibodies (including caninized antibodies) the CDRL1 comprises the amino acid sequence of SEQ ID NO: 129, a variant of SEQ ID NO: 129, a conservatively modified variant of SEQ ID NO: 129, or a variant of SEQ ID NO: 129 that comprises the canonical structure class of 6; the CDRL2 comprises the amino acid sequence of SEQ ID NO: 132, a variant of SEQ ID NO: 132, a conservatively modified variant of SEQ ID NO: 132, or a variant of SEQ ID NO: 132 that comprises the canonical structure class of 1; the CDRL3 comprises the amino acid sequence of SEQ ID NO: 139, a variant of SEQ ID NO: 139, a conservatively modified variant of SEQ ID NO: 139, or a variant of SEQ ID NO: 139 that comprises the canonical structure class of 1, the CDRH1 comprises the amino acid sequence of SEQ ID NO: 143, a variant of SEQ ID NO: 143, a conservatively modified variant of SEQ ID NO: 143, or a variant of SEQ ID NO: 143 that comprises the canonical structure class of 1; the CDRH2 comprises the amino acid sequence of SEQ ID NO: 148, a variant of SEQ ID NO: 148, a conservatively modified variant of SEQ ID NO: 148, and a variant of SEQ ID NO: 148 that comprises the canonical structure class of 3A, the CDRH3 comprises the amino acid sequence of SEQ ID NO: 153, a variant of SEQ ID NO: 153, a conservatively modified variant of SEQ ID NO: 153, or a variant of SEQ ID NO: 153 that comprises the canonical structure class of 13. In particular embodiments of this type, when the antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 159, or SEQ ID NO: 160, or SEQ ID NO: 161, or any combination thereof.

The present invention includes antibodies and antigen binding fragments thereof that bind canine interleukin-4 receptor alpha (IL-4R$_\alpha$) with specificity. In particular embodiments of this type, the antibodies and antigen binding fragments thereof bind canine IL-4R$_\alpha$ and block the binding of canine IL-4R$_\alpha$ to canine IL-4 and/or IL-13. As indicated above, the isolated mammalian antibodies or antigen binding fragments thereof can be caninized antibodies or caninized antigen binding fragments thereof. In other embodiments, the isolated mammalian antibodies or antigen binding fragments thereof can be murine antibodies or murine antigen binding fragments thereof.

The caninized antibodies or caninized antigen binding fragments thereof of the present invention can comprise a hinge region. In a particular embodiment of this type, the hinge region comprises the amino acid sequence of SEQ ID NO: 101. In another embodiment the hinge region comprises the amino acid sequence of SEQ ID NO: 102. In still another embodiment the hinge region comprises the amino acid sequence of SEQ ID NO: 103. In yet another embodiment the hinge region comprises the amino acid sequence of SEQ ID NO: 104.

In certain embodiments the caninized antibody or antigen binding fragment thereof, comprises a heavy chain that comprises the amino acid sequence of SEQ ID NO: 164. In particular embodiments of this type, the heavy chain is encoded by the nucleotide sequence of SEQ ID NO: 163. In other embodiments the caninized antibody or antigen binding fragment thereof, comprises a heavy chain that comprises the amino acid sequence of SEQ ID NO: 166. In particular embodiments of this type, the heavy chain is encoded by the nucleotide sequence of SEQ ID NO: 165. In still other embodiments, the caninized antibody or antigen binding fragment thereof, comprises a heavy chain that comprises the amino acid sequence of SEQ ID NO: 168. In particular embodiments of this type, the heavy chain is encoded by the nucleotide sequence of SEQ ID NO: 167. In specific embodiments of such types, when the caninized antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 154, or SEQ ID NO: 155, or SEQ ID NO: 156, or any combination thereof.

In related embodiments the caninized antibody or antigen binding fragment thereof, comprises a light chain that comprises the amino acid sequence of SEQ ID NO: 170. In particular embodiments of this type, the light chain is encoded by the nucleotide sequence of SEQ ID NO: 169. In other embodiments the caninized antibody or antigen binding fragment thereof, comprises a light chain comprising the amino acid sequence of SEQ ID NO: 172. In particular embodiments of this type, the light chain is encoded by the nucleotide sequence of SEQ ID NO: 171. In yet other embodiments the caninized antibody or antigen binding fragment thereof, comprises a light chain comprising the amino acid sequence of SEQ ID NO: 174. In particular embodiments of this type, the light chain is encoded by the nucleotide sequence of SEQ ID NO: 173. In particular embodiments of such types, when the caninized antibody (or antigen binding fragment thereof) binds canine interleukin-4 receptor α (IL-4R$_\alpha$) the antibody binds to at least one amino acid residue, preferably two to five amino acid residues, and/or more preferably three to eight amino acid residues or more within the amino acid sequence of SEQ ID NO: 154, or SEQ ID NO: 155, or SEQ ID NO: 156, or any combination thereof.

The present invention further provides antibodies comprising a combination of such heavy chains and light chains. In particular embodiments the heavy chain comprises the amino acid sequence of SEQ ID NO: 164 and the light chain comprises the amino acid sequence of SEQ ID NO: 170. In more particular embodiments of this type, the heavy chain is encoded by the nucleotide sequence of SEQ ID NO: 163 and the light chain is encoded by the nucleotide sequence of SEQ ID NO: 169. In other embodiments the heavy chain comprises the amino acid sequence of SEQ ID NO: 166 and the light chain comprises the amino acid sequence of SEQ ID NO: 172. In more particular embodiments of this type, the heavy chain is encoded by the nucleotide sequence of SEQ ID NO: 165 and the light chain is encoded by the nucleotide sequence of SEQ ID NO: 171. In still other embodiments the heavy chain comprises the amino acid sequence of SEQ ID NO: 168 and the light chain comprises the amino acid sequence of SEQ ID NO: 174. In more particular embodiments of this type, the heavy chain is encoded by the nucleotide sequence of SEQ ID NO: 167 and the light chain is encoded by the nucleotide sequence of SEQ ID NO: 173.

In related embodiments the heavy chain comprises the amino acid sequence of SEQ ID NO: 164 and the light chain comprises the amino acid sequence of SEQ ID NO: 172. In other embodiments the heavy chain comprises the amino acid sequence of SEQ ID NO: 164 and the light chain comprises the amino acid sequence of SEQ ID NO: 174. In still other embodiments the heavy chain comprises the amino acid sequence of SEQ ID NO: 166 and the light chain comprises the amino acid sequence of SEQ ID NO: 170. In yet other embodiments the heavy chain comprises the amino acid sequence of SEQ ID NO: 166 and the light chain comprises the amino acid sequence of SEQ ID NO: 174. In still other embodiments the heavy chain comprises the amino acid sequence of SEQ ID NO: 168 and the light chain comprises the amino acid sequence of SEQ ID NO: 170. In other embodiments the heavy chain comprises the amino acid sequence of SEQ ID NO: 168 and the light chain comprises the amino acid sequence of SEQ ID NO: 172.

In particular embodiments of such types, when the caninized antibody (or antigen binding fragment thereof) binds canine interleukin-4 receptor α (IL-4R$_\alpha$) the antibody binds to at least one amino acid residue, preferably two to five amino acid residues, and/or more preferably three to eight or more amino acid residues within the amino acid sequence of SEQ ID NO: 154, or SEQ ID NO: 155, or SEQ ID NO: 156, or any combination thereof.

Accordingly, the present invention further provides isolated mammalian antibodies or antigen binding fragments thereof (including caninized antibodies or antigen binding fragments thereof) that bind canine interleukin-4 receptor α (IL-4R$_\alpha$) with specificity, and when bound to canine IL-4R$_\alpha$ the antibody binds to at least one amino acid residue, preferably two to five amino acid residues, and/or more preferably three to eight amino acid residues or more within the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162, or any combination thereof. In particular embodiments, the antibody or antigen binding fragment thereof binds canine IL-4R$_\alpha$ and blocks the binding of canine IL-4R$_\alpha$ to canine interleukin-4.

The present invention further provides mammalian antibodies or antigen binding fragments thereof that bind to canine IL-4R$_\alpha$ with a dissociation constant (Kd) that is lower (e.g., $1 \times 10^{-13}$ M, or lower) than $1 \times 10^{-12}$ M. In particular embodiments the mammalian antibodies or antigen binding fragments thereof bind to canine IL-4R$_\alpha$ with a dissociation constant of $1 \times 10^{-5}$ M to $1 \times 10^{-12}$ M. In more particular embodiments the mammalian antibodies or antigen binding fragments thereof bind to canine IL-4R$_\alpha$ with a dissociation constant of $1 \times 10^{-7}$ M to $1 \times 10^{-11}$ M. In still more particular embodiments the mammalian antibodies or antigen binding fragments thereof bind to canine IL-4R$_\alpha$ with a dissociation constant of $1 \times 10^{-8}$ M to $1 \times 10^{-11}$ M. In yet more particular embodiments the mammalian antibodies or antigen binding fragments thereof bind to canine IL-4R$_\alpha$ with a dissociation constant of $1\times10^{-8}$M to $1\times10^{-10}$ M.

The present invention also provides mammalian antibodies or antigen binding fragments thereof that bind to canine IL-4R$_\alpha$ with an on rate ($k_{on}$) that is greater than $1\times10^7$M$^{-1}$s$^{-1}$. In particular embodiments the mammalian antibodies or antigen binding fragments thereof bind to canine IL-4R$_\alpha$ with an on rate of $1\times10^2$ M$^{-1}$s$^{-1}$ to $1\times10^7$M$^{-1}$s$^{-1}$. In more particular embodiments the mammalian antibodies or antigen binding fragments thereof bind to canine IL-4R$_\alpha$ with an on rate of $1\times10^3$ M$^{-1}$s$^{-1}$ to $1\times10^6$M$^{-1}$s$^{-1}$. In still more particular embodiments the mammalian antibodies or antigen binding fragments thereof bind to canine IL-4R$_\alpha$ with an on rate of $1\times10^3$ M$^{-1}$s$^{-1}$ to $1\times10^5$M$^{-1}$s$^{-1}$. In yet more particular embodiments the mammalian antibodies or antigen binding fragments thereof bind to canine IL-4R$_\alpha$ on rate of $1\times10^4$ M$^{-1}$s$^{-1}$ to $1\times10^5$M$^{-1}$s$^{-1}$.

The present invention further provides mammalian antibodies or antigen binding fragments thereof that bind to canine IL-4R$_\alpha$ with an off rate ($k_{off}$) slower than $1\times10^{-7}$ s$^{-1}$. In particular embodiments the mammalian antibodies or antigen binding fragments thereof bind to canine IL-4R$_\alpha$ with an off rate of $1\times10^{-3}$ s$^{-1}$ to $1\times10^{-8}$ s$^{-1}$. In more particular embodiments the mammalian antibodies or antigen binding fragments thereof bind to canine IL-4R$_\alpha$ with an off rate of $1\times10^{-4}$ s$^{-1}$ to $1\times10^{-7}$ s$^{-1}$. In still more particular embodiments the mammalian antibodies or antigen binding fragments thereof bind to canine IL-4R$_\alpha$ with an off rate of $1\times10^{-5}$ s$^{-1}$ to $1\times10^{-7}$ s$^{-1}$.

In particular embodiments, a mammalian antibody of the present invention (including chimeric antibodies) blocks the binding of canine IL-4 with IL-4R$_\alpha$. In more particular embodiments the antibody blocks the binding of canine IL-4 to IL-4R$_\alpha$ with a minimum EC50 of $1\times10^{-8}$M to $1\times10^{-9}$M or an even lower concentration. In still more particular embodiments the EC50 is $5\times10^{-9}$M to $5\times10^{-13}$M. In still more particular embodiments the EC50 is between $5\times10^{-9}$M and $5\times10^{-11}$M.

In related embodiments, the mammalian antibodies or antigen binding fragments thereof negatively attenuate, e.g., inhibit, the cell signaling pathway(s) mediated by IL-4 and/or IL-13 binding to type I and/or type II IL-4 receptors. In particular embodiments, the mammalian antibodies or antigen binding fragments thereof ameliorate a pruritic inflammatory skin disease, e.g., atopic dermatitis, in an animal subject. In more specific embodiments the animal subject is a canine. In a related embodiment, the animal subject is a feline.

Accordingly, any of the antibodies of the present invention can exhibit one, two, three, four, or all these properties, i.e., the aforesaid dissociation constants with canine IL-4R$_\alpha$, the aforesaid on rates for binding with canine IL-4R$_\alpha$, the aforesaid off rates for dissociating from the antibody-canine IL-4R$_\alpha$ binding complex, inhibiting the cell signaling pathway(s) mediated by IL-4 and/or IL-13 binding to type I and/or type II IL-4 receptors, or ameliorating a pruritic inflammatory skin disease, e.g., atopic dermatitis, in an animal subject.

As indicated above, the antibodies (and antigen binding fragments thereof) of the present invention, including the aforesaid antibodies (and antigen binding fragments thereof), can be monoclonal antibodies (and antigen binding fragments thereof), mammalian antibodies (and antigen binding fragments thereof), e.g., murine (mouse) antibodies (and antigen binding fragments thereof), caninized antibodies (and antigen binding fragments thereof) including caninized murine antibodies (and antigen binding fragments thereof), and in certain embodiments the antibodies (and antigen binding fragments thereof) are isolated.

The present invention further provides nucleic acids (including isolated nucleic acids) that encode any one of the light chains of the caninized antibody of the present invention. Similarly, the present invention provides isolated nucleic acids that encode any one of the heavy chains of the caninized antibody of the present invention.

The present invention further provides expression vectors that comprise one or more of the nucleic acids (including isolated nucleic acids) of the present invention. The present invention further provides host cells that comprise one or more expression vectors of the present invention.

In particular embodiments, the antibody is a recombinant antibody or an antigen binding fragment thereof. In related embodiments, the variable heavy chain domain and variable light chain domain are connected by a flexible linker to form a single-chain antibody.

In particular embodiments, the antibody or antigen binding fragment is a Fab fragment.

In other embodiments, the antibody or antigen binding fragment is a Fab' fragment. In other embodiments, the antibody or antigen binding fragment is a (Fab')$_2$ fragment. In still other embodiments, the antibody or antigen binding fragment is a diabody. In particular embodiments, the antibody or antigen binding fragment is a domain antibody. In particular embodiments, the antibody or antigen binding fragment is a single domain antibody.

In particular embodiments, a caninized murine anti-canine IL-4R$_\alpha$ antibody or antigen binding fragment negatively attenuates the cell signaling pathway(s) mediated by IL-4 and/or IL-13 binding to type I and/or type II IL-4 receptors in an animal subject (e.g., canine) being treated. In more particular embodiments, administration of a caninized murine anti-canine IL-4R$_\alpha$ antibody or antigen binding fragment of the present invention serves to ameliorate one or more symptom of atopic dermatitis in the animal subject (e.g., canine) being treated.

The present invention further provides isolated nucleic acids that encode caninized murine anti-canine IL-4R$_\alpha$ antibodies or portions thereof. In related embodiments such antibodies or antigen binding fragments can be used for the preparation of a medicament to treat atopic dermatitis in a canine subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

In yet additional embodiments, an expression vector is provided comprising an isolated nucleic acid encoding any of the caninized murine anti-canine IL-4R$_\alpha$ antibodies or antigen binding fragments of the invention. The invention also relates to a host cell comprising any of the expression vectors described herein. In particular embodiments, these nucleic acids, expression vectors or polypeptides of the invention are useful in methods of making an antibody.

The present invention further provides peptides (including isolated antigenic peptides) that consist of 80 or fewer amino acid residues that comprise the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162. In related embodiments, the peptides (including isolated antigenic peptides) consist of 60 or fewer amino acid residues that comprise the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162. In related embodiments, the peptides (including isolated antigenic peptides) consist of 10 to 45 amino acid residues that comprise the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162. In yet other embodiments the peptides (including isolated antigenic peptides) consist of 5 to 25 amino acid residues from the, or that comprise the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162.

The present invention further provides antigenic peptides (including isolated peptides) that consist of 80 or fewer amino acid residues that comprise an amino acid sequence that is 80%, 85%, 90%, 95% or 100% identical with the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162 and binds to an isolated mammalian antibody or antigen binding fragment thereof the present invention. In related embodiments, the antigenic peptides (including isolated antigenic peptides) consist of 60 or fewer amino acid residues that comprise an amino acid sequence that is 80%, 85%, 90%, 95% or 100% identical with the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162 and binds to an isolated mammalian antibody or antigen binding fragment thereof. In other embodiments the peptides consist of 5 to 25 amino acid residues from the, or that comprise an amino acid sequence that is 80%, 85%, 90%, 95% or 100% identical with the amino acid sequence of SEQ ID NO: 125, or SEQ ID NO: 126, or SEQ ID NO: 127, or SEQ ID NO: 128, or SEQ ID NO: 154, or SEQ ID NO: 155, or SEQ ID NO: 156, or SEQ ID NO: 157, or SEQ ID NO: 158, or SEQ ID NO: 159, or SEQ ID NO: 160, or SEQ ID NO: 161, or SEQ ID NO: 162 and binds to an isolated mammalian antibody or antigen binding fragment thereof. In particular embodiments the mammalian antibody comprises the CDRs of 4D8. In other embodiments the mammalian antibody comprises the CDRs of 11H2. In yet other embodiments the mammalian antibody comprises the CDRs of 4H3. In still other embodiments the mammalian antibody comprises the CDRs of 11B6. In yet other embodiments the mammalian antibody comprises the CDRs of 2E2. In still other embodiments the mammalian antibody comprises the CDRs of 6C12.

The present invention further provides fusion proteins that comprise any of the aforesaid peptides. In a particular embodiment, the fusion protein comprises such an antigenic peptide and an Fc region of a non-canine mammalian IgG antibody. In a more particular embodiment the fusion protein comprises an Fc region of a non-canine mammalian IgG antibody. In certain embodiments the non-canine mammalian IgG antibody is a murine IgG. In alternative embodiments the non-canine mammalian IgG antibody is a human IgG. In other embodiments the non-canine mammalian IgG antibody is an equine IgG. In still other embodiments the non-canine mammalian IgG antibody is a porcine IgG. In yet other embodiments the non-canine mammalian IgG antibody is a bovine IgG.

In particular embodiments the non-canine mammalian IgG antibody is an IgG1. In other embodiments the non-canine mammalian IgG antibody is an IgG2a. In still other embodiments the non-canine mammalian IgG antibody is an IgG3. In yet other embodiments the non-canine mammalian IgG antibody is an IgG4. In other embodiments the fusion protein comprises any of the aforesaid antigenic peptides and maltose-binding protein. In yet other embodiments, the fusion protein comprises any of the aforesaid antigenic peptides and beta-galactosidase. In still other embodiments the fusion protein comprises any of the aforesaid antigenic peptides and glutathione S-transferase. In yet other embodiments, the fusion protein comprises any of the aforesaid antigenic peptides and thioredoxin. In still other embodiments the fusion protein comprises any of the aforesaid antigenic peptides and Gro EL. In yet other embodiments the fusion protein comprises any of the aforesaid antigenic peptides and NusA.

The present invention further provides nucleic acids (including isolated nucleic acids) that encode the antigenic peptides and the corresponding fusion proteins of the present invention. The present invention also provides expression vectors that comprise these nucleic acids and host cells that comprise one or more expression vectors of the present invention.

In addition, the present invention includes pharmaceutical compositions comprising anti-canine IL-4R$_\alpha$ antibodies or antigen binding fragments thereof of the present invention, antigenic peptides (including isolated antigenic peptides) from canine IL-4R$_\alpha$, fusion proteins comprising the antigenic peptides from canine IL-4R$_\alpha$ of the present invention, nucleic acids (including isolated nucleic acids) encoding the antigenic fragments and/or fusion proteins of the present invention, the expression vectors comprising such nucleic acids, or any combination thereof, and a pharmaceutically acceptable carrier or diluent.

In addition, the present invention provides methods of negatively attenuating the activity of IL-4 and/or IL-13 comprising administering to an animal subject in need thereof a therapeutically effective amount of such pharmaceutical compositions. In certain embodiments the method is used for the treatment of atopic dermatitis in a canine.

These and other aspects of the present invention will be better appreciated by reference to the following Brief Description of the Drawings and the Detailed Description.

BRIEF DESCRIPTION OF THE DRAWINGS

FIG. 3A depicts the concentration-dependent ability of the monoclonal antibodies 11B6 (♦), 4D8(■), 4H3(▲), 2E2(▼), and 11H2(♦) to individually block the binding of IL-4 with the cell-based CHO-cIL-4R$_\alpha$. FIG. 3B depicts the concentration-dependent ability of monoclonal antibodies 11H2(♦), and 6C12(■) to individually block the binding of IL-4 with the cell-based CHO-cIL-4R$_\alpha$. The abscissa depicts the log concentration of the mAb (nM) being added, the ordinate depicts the mean fluorescence intensity (MFI) employing FACS.

DETAILED DESCRIPTION

Figure 1:
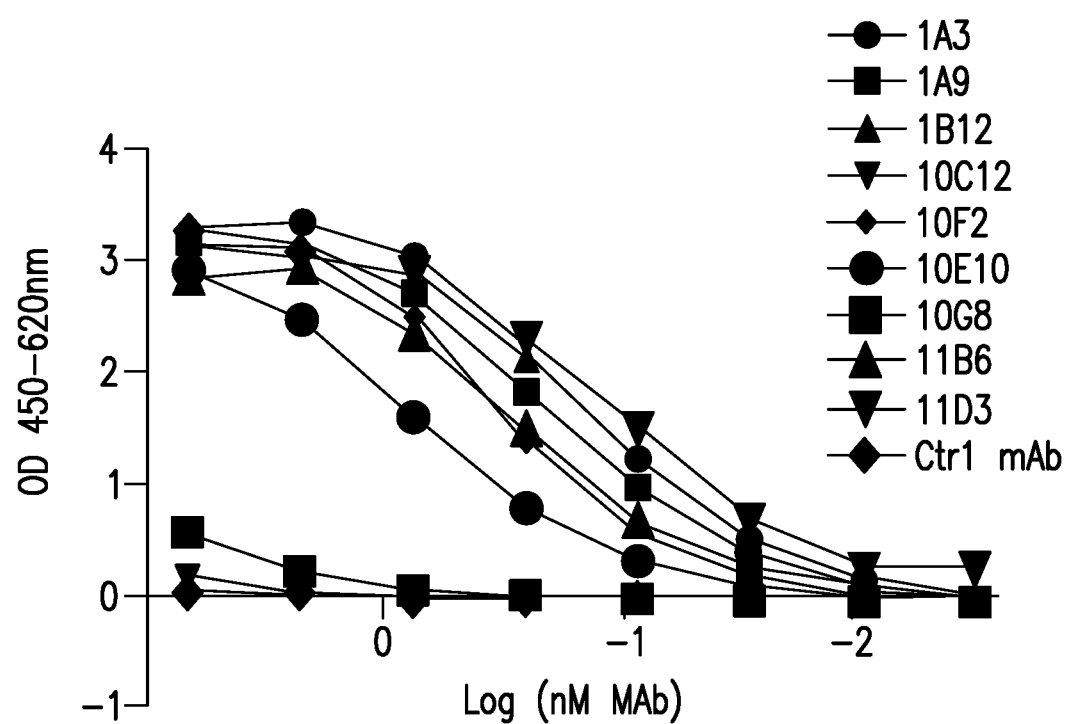
FIG. 1 shows the reactivity of purified mouse anti-canine IL-4R$_\alpha$ monoclonal antibodies (mAbs) against the extracellular domain of canine IL-4R$_\alpha$. Various mouse mAbs were tested for their binding to the extracellular domain of canine IL-4R$_\alpha$ by ELISA. The mAbs tested are designated as: 1A3(●), 1A9(■), 1B12 (▲), 10C12(▼), 10F2(♦), 10E10 (●), 10 G8(■), 11B6(▲), 11D3(▼) and the control antibody (♦). The abscissa depicts the log concentration of the mAB (nM) being added, the ordinate depicts the optical density obtained by the ELISA.

A variety of approaches for treatment of human AD are now under investigation in many clinical trials [reviewed in Malajian et al., *New pathogenic and therapeutic paradigms in atopic dermatitis Cytokine*, (2014)]. Some of these approaches aim to interfere with one or more of the signaling molecules/events leading to the development and activation of Th2 cells. One line of investigation in this area encompasses approaches for blockade of the actions of key interleukin drivers of the Th2 pathway. Based on the observations that AD is largely a Th2 dominated disease and the accumulating data supporting a key role for the combined actions of both IL-4 and IL-13 as key drivers of Th2 cell development, and based on the data indicating that IL-4 receptor α chain is a requisite receptor for signaling from both cytokines, the present invention describes the generation and characterization of monoclonal antibodies that block the binding of canine IL-4 and canine IL-13 to the type-I and type II IL-4 receptors and subsequently inhibit the signaling from both canine IL-4 and IL-13. These antibodies have utilities in treatment of atopic dermatitis and other diseases in companion animals as disclosed herein.

Abbreviations

Throughout the detailed description and examples of the invention the following abbreviations will be used:
ADCC Antibody-dependent cellular cytotoxicity
CDC Complement-dependent cytotoxicity
CDR Complementarity determining region in the immunoglobulin variable regions, defined using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat [*Sequences of Proteins of Immunological Interest*, 5th Ed. Public Health Service, National Institutes of Health, Bethesda, Md. (1991)]
mAb Monoclonal antibody (also Mab or MAb)
MES 2-(N-morpholino)ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VL Immunoglobulin light chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, e.g., a canine experimental subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., canine, feline, or human) and most preferably a canine.

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

"Treat" or "treating" means to administer a therapeutic agent, such as a composition containing any of the antibodies or antigen binding fragments of the present invention, internally or externally to a canine subject or patient having one or more disease symptoms, or being suspected of having a disease, for which the agent has therapeutic activity.

Typically, the agent is administered in an amount effective to alleviate and/or ameliorate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient (e.g., canine), and the ability of the pharmaceutical composition to elicit a desired response in the subject. Whether a disease symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine) or research subject, refers to therapeutic treatment, as well as research and diagnostic applications. "Treatment" as it applies to a human, veterinary (e.g., canine), or research subject, or cell, tissue, or organ, encompasses contact of the antibodies or antigen binding fragments of the present invention to a canine or other animal subject, a cell, tissue, physiological compartment, or physiological fluid.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse antibody) in both chains. Optionally the heavy and/or light chains of the canine antibody may contain some foreign non-CDR residues, e.g., so as to preserve the conformation of the foreign CDRs within the canine antibody, and/or to modify the Fc function, as exemplified below.

Canine IL-4R$_\alpha$ has been found to comprise the amino acid sequence of SEQ ID NO: 2 [SEQ ID NO: 4, without the signal sequence]. In a specific embodiment canine IL-4R$_\alpha$ is encoded by a nucleic acid that comprises the nucleotide sequence of SEQ ID NO: 1 [SEQ ID NO: 3, without the signal sequence]. Canine IL-4R$_\alpha$ sequences may differ by having, for example, conserved variations in non-conserved regions, but the canine IL-4R$_\alpha$ will have substantially the same biological function as the canine IL-4R$_\alpha$ comprising the amino acid sequence of SEQ ID NO: 2 [SEQ ID NO: 4, without the signal sequence].

The cytokines IL-4 and IL-13 have been implicated in the pathogenesis of a variety of allergic diseases in humans and animals, including asthma and atopic dermatitis. Because the IL-4 receptor α chain is a requisite receptor for the signaling from either of these cytokines, the present invention describes the generation and characterization of monoclonal antibodies that block the binding of canine IL-4 and canine IL-13 to IL-4R$_\alpha$ and thereby inhibits the signaling from both canine IL-4 and IL-13. These antibodies therefore have utility in treatment of atopic dermatitis and other diseases in companion animals as disclosed herein. In addition, a biological function of canine IL-4R$_\alpha$ may be having, for example, an epitope in the extracellular domain that is specifically bound by an antibody of the instant disclosure.

A particular canine IL-4R$_\alpha$ amino acid sequence will generally be at least 90% identical to the canine IL-4R$_\alpha$ comprising the amino acid sequence of SEQ ID NO: 4. In certain cases, a canine IL-4R$_\alpha$ may be at least 95%, or even at least 96%, 97%, 98% or 99% identical to the canine IL-4R$_\alpha$ comprising the amino acid sequence of SEQ ID NO: 4. In certain embodiments, a canine IL-4R$_\alpha$ amino acid sequence will display no more than 10 amino acid differences from the canine IL-4R$_\alpha$ comprising the amino acid sequence of SEQ ID NO: 4. In certain embodiments, the canine IL-4R$_\alpha$ amino acid sequence may display no more than 5, or even no more than 4, 3, 2, or 1 amino acid difference from the canine IL-4R$_\alpha$ comprising the amino acid sequence of SEQ ID NO: 4. Percent identity can be determined as described herein below.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

Anti-Canine IL-4$R_\alpha$ Antibodies

The present invention provides isolated antibodies (particularly murine anti-canine IL-4$R_\alpha$ antibodies and caninized antibodies thereof) or antigen binding fragments thereof that bind canine IL-4$R_\alpha$ and uses of such antibodies or fragments thereof. In specific embodiments murine anti-canine IL-4$R_\alpha$ CDRs from murine anti-canine IL-4$R_\alpha$ antibodies are provided that have been shown to both bind canine IL-4$R_\alpha$ and to block the binding of canine IL-4$R_\alpha$ to one or more of its ligands, canine IL-4 or IL-13. These CDRs can be inserted into a modified canine frame of a canine antibody to generate a caninized murine anti-canine IL-4$R_\alpha$ antibody.

As used herein, an "anti-canine IL-4$R_\alpha$ antibody" refers to an antibody that was raised against canine IL-4$R_\alpha$ (e.g., in a mammal such as a mouse or rabbit) and that specifically binds to canine IL-4$R_\alpha$. An antibody that "specifically binds to canine IL-4$R_\alpha$," and in particular canine IL-4$R_\alpha$, or an antibody that "specifically binds to a polypeptide comprising the amino acid sequence of canine IL-4$R_\alpha$", is an antibody that exhibits preferential binding to canine IL-4$R_\alpha$ as compared to other antigens, but this specificity does not require absolute binding specificity. An anti-canine IL-4$R_\alpha$ antibody is considered "specific" for canine IL-4$R_\alpha$ if its binding is determinative of the presence of canine IL-4$R_\alpha$ in a sample, or if it is capable of altering the activity of canine IL-4$R_\alpha$ without unduly interfering with the activity of other molecules in a canine sample, e.g. without producing undesired results such as false positives in a diagnostic context or side effects in a therapeutic context. The degree of specificity necessary for an anti-canine IL-4$R_\alpha$ antibody may depend on the intended use of the antibody, and at any rate is defined by its suitability for use for an intended purpose. The antibody, or binding compound derived from the antigen-binding site of an antibody, of the contemplated method binds to its antigen, or a variant or mutein thereof, with an affinity that is at least two-fold greater, preferably at least ten-times greater, more preferably at least 20-times greater, and most preferably at least 100-times greater than the affinity with any other antigen.

As used herein, an antibody is said to bind specifically to a polypeptide comprising a given antigen sequence (in this case a portion of the amino acid sequence of canine IL-4$R_\alpha$) if it binds to polypeptides comprising the portion of the amino acid sequence of canine IL-4$R_\alpha$, but does not bind to other canine proteins lacking that portion of the sequence of canine IL-4$R_\alpha$. For example, an antibody that specifically binds to a polypeptide comprising canine IL-4$R_\alpha$, may bind to a FLAG®-tagged form of canine IL-4$R_\alpha$, but will not bind to other FLAG®-tagged canine proteins. An antibody, or binding compound derived from the antigen-binding site of an antibody, binds to its canine antigen, or a variant or mutein thereof, "with specificity" when it has an affinity for that canine antigen or a variant or mutein thereof which is at least ten-times greater, more preferably at least 20-times greater, and even more preferably at least 100-times greater than its affinity for any other canine antigen tested.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), canonized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antigen binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "fragment crystallizable" ("Fc") region contains two heavy chain fragments comprising the $C_H3$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. [See, Pluckthun, THE PHARMACOLOGY OF MONOCLONAL ANTIBODIES, vol. 113 Rosenburg and Moore eds., Springer-Verlag, New York, pp. 269-315 (1994); WO 88/01649; and U.S. Pat. Nos. 4,946,778 and 5,260,203.]

As used herein, the term "canonical structure" refers to the local conformation that can be adopted by each of the hypervariable regions of the heavy and light chain of an antibody within the framework that they reside. For each hypervariable region, there are a small number of canonical structures (generally denoted by simple integers such as 1 or 2 etc.), which can be predicted with great accuracy from the amino acid sequences of the corresponding hypervariable region [particularly within the context of the amino acid sequence of its framework, as provided below for the corresponding anti-canine IL-4$R_\alpha$ variable domains (see, Table 3 below)]. These canonical structures can be determinative regarding whether a modification of the amino acid sequence of a given CDR will result in the retention or loss of the ability to bind to its antigen binding partner [See, Chothia and Lesk, *Canonical Structures for the hypervariable regions of immunoglobulins, J. Mol. Biol.* 196:901-917 (1987); Chothia et al., *Conformation of immunoglobulin hypervariable regions, Nature,* 34:877-883(1989); and Al-Lazikani et al., *Standard Conformations for the canonical structures of immunoglobulins, J. Mol. Biol.* 273:927-948 (1997)].

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. [See, e.g., Muyldermans et al., *Trends Biochem. Sci.* 26:230 (2001); Reichmann et al., *J. Immunol. Methods* 231:25 (1999); WO 94/04678; WO 94/25591; U.S. Pat. No. 6,005,079]. In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. [See, EP 0 404 097 B1; WO 93/11161; and Holliger et al., *Proc. Natl. Acad. Sci. USA* 90: 6444-6448 (1993)]. For a review of engineered antibody variants [generally see Holliger and Hudson *Nat. Biotechnol.* 23:1126-1136 (2005)].

Typically, an antibody or antigen binding fragment of the invention retains at least 10% of its canine IL-4$R_\alpha$ binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine IL-4$R_\alpha$ binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., *Proc. Natl. Acad. Sci. USA* 81: 6851-6855 (1984)]. Typically the variable domains are obtained from an antibody from an experimental animal (the "parental antibody"), such as a rodent, and the constant domain sequences are obtained from the animal subject antibodies, e.g., human or canine so that the resulting chimeric antibody will be less likely to elicit an adverse immune response in a canine or human subject respectively, than the parental (e.g., rodent) antibody.

As used herein, the term "caninized antibody" refers to forms of antibodies that contain sequences from both canine and non-canine (e.g., murine) antibodies. In general, the caninized antibody will comprise substantially all of at least one or more typically, two variable domains in which all or substantially all of the hypervariable loops correspond to those of a non-canine immunoglobulin (e.g., comprising 6 murine anti-canine IL-4$R_\alpha$ CDRs as exemplified below), and all or substantially all of the framework (FR) regions (and typically all or substantially all of the remaining frame) are those of a canine immunoglobulin sequence. As exemplified herein, a caninized antibody comprises both the three heavy chain CDRs and the three light chain CDRS from a murine anti-canine IL-4$R_\alpha$ antibody together with a canine frame or a modified canine frame. A modified canine frame comprises one or more amino acids changes as exemplified herein that further optimize the effectiveness of the caninized antibody, e.g., to increase its binding to canine IL-4$R_\alpha$ and/or its ability to block the binding of canine IL-4 and/or canine IL-13 to the type-I and/or type II IL-4 receptors.

The term "fully canine antibody" refers to an antibody that comprises canine immunoglobulin protein sequences only. A fully canine antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully canine antibody may contain rat carbohydrate chains if produced in a rat, in a rat cell, or in a hybridoma derived from a rat cell. Similarly, "rat antibody" refers to an antibody that comprises rat immunoglobulin sequences only.

There are four known IgG heavy chain subtypes of dog IgG and they are referred to as IgG-A, IgG-B, IgG-C, and IgG-D. The two known light chain subtypes are referred to as lambda and kappa.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest,* 5th Ed. Public Health Service, National Institutes of Health, Bethesda, Md. (1991), defining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

Besides binding and activating of canine immune cells, a canine or caninized antibody against IL-4R$_\alpha$ optimally has two attributes:
1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but displays undesirable ADCC activity. Moreover, neither IgG-C nor IgG-D can be purified on protein A columns, although IgG-D display no ADCC activity. (IgG-C has considerable ADCC activity). One way the present invention overcomes this difficulty is by providing mutant canine IgG-B antibodies specific to IL-4R$_\alpha$; such antibodies lack effector functions such as ADCC and can be easily of purified using industry standard protein A chromatography.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of Murine Anti-Canine IL-4R$_\alpha$ and Caninized Murine Anti-Canine IL-4R$_\alpha$ Antibodies The present invention provides isolated murine anti-canine IL-4R$_\alpha$ antibodies and caninized antibodies thereof, methods of use of the antibodies or antigen binding fragments thereof in the treatment of disease e.g., the treatment of atopic dermatitis in canines. In canine, there are four IgG heavy chains referred to as A, B, C, and D. These heavy chains represent four different subclasses of dog IgG, which are referred to as IgGA, IgGB, IgGC and IgGD. Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region".

The DNA and amino acid sequences of these four heavy chains were first identified by Tang et al. [*Vet. Immunol. Immunopathol.* 80: 259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example the kappa light chain amino acid sequence has accession number ABY 57289.1 and the lambda light chain has accession number ABY 55569.1.

In the present invention, the amino acid sequence for each of the four canine IgG Fc fragments is based on the identified boundary of CH1 and CH2 domains as determined by Tang et al, supra. Caninized murine anti-canine IL-4R$_\alpha$ antibodies that bind canine IL-4R$_\alpha$ include, but are not limited to: antibodies that comprise canine IgG-A, IgG-B, and IgG-D heavy chains and/or canine kappa light chains together with murine anti-canine IL-4R$_\alpha$ CDRs. Accordingly, the present invention provides isolated murine anti-canine IL-4R$_\alpha$ and/or caninized murine anti-canine IL-4R$_\alpha$ antibodies or antigen binding fragments thereof that bind to canine IL-4R$_\alpha$ and block the binding of canine IL-4 and canine IL-13 to the type-I or type II IL-4 receptors.

The present invention further provides full length canine heavy chains that can be matched with corresponding light chains to make a caninized antibody. Accordingly, the present invention further provides caninized murine anti-canine antigen antibodies (including isolated caninized murine anti-canine IL-4R$_\alpha$ antibodies) and methods of use of the antibodies or antigen binding fragments thereof in the treatment of disease e.g., the treatment of atopic dermatitis in canines.

The present invention also provides caninized murine anti-canine-IL-4Rα antibodies that comprise a canine fragment crystallizable region (cFc region) in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function. In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

In order to generate variants of canine IgG that lack effector functions, a number of mutant canine IgGB heavy chains were generated. These variants may include one or more of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to Fc$_\gamma$RI and C1q to assess their potential for mediation of immune effector functions. [see, U.S. provisional patent application 62/030, 812, filed Jul. 30, 2014, and U.S. provisional patent application 62/092,496, filed Dec. 16, 2014, the contents of both of which are hereby incorporated by reference in their entireties.]

The present invention also provides modified canine IgGDs which in place of its natural IgGD hinge region they comprise a hinge region from:

```
IgGA:
                                SEQ ID NO: 101
FNECRCTDTPPCPVPEP,;

IgGB:
                                SEQ ID NO: 102
PKRENGRVPRPPDCPKCPAPEM,;
or

IgGC:
                                SEQ ID NO: 103
AKECECKCNCNNCPCPGCGL,.
```

Alternatively, the IgGD hinge region can be genetically modified by replacing a serine residue with a proline residue, i.e., PKESTCKCIPCPVPES, SEQ ID NO: 104 (with the proline residue (P) underlined and in bold substituting for the naturally occurring serine residue). Such modifications can lead to a canine IgGD lacking fab arm exchange. The modified canine IgGDs can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgGD can be modified so that it encodes the modified IgGDs. The modified nucleic acid sequences are then cloned into expression plasmids for protein expression.

The antibody or antigen binding fragment thereof that binds canine IL-4R$_\alpha$ can comprise one, two, three, four, five, or six of the complementarity determining regions (CDRs) of the murine anti-canine antibody as described herein. The one, two, three, four, five, or six CDRs may be independently selected from the CDR sequences of those provided below. In a further embodiment, the isolated antibody or antigen-binding fragment thereof that binds canine IL-4R$_\alpha$ comprises a canine antibody kappa light chain comprising a murine light chain CDR-1, CDR-2 and/or CDR-3 and a canine antibody heavy chain IgG comprising a murine heavy chain CDR-1, CDR-2 and/or CDR-3.

In other embodiments, the invention provides antibodies or antigen binding fragments thereof that specifically binds IL-4R$_\alpha$ and have canine antibody kappa light chains comprising one to six different CDRs comprising at least 80%, 85%, 90%, 95%, 98% or 99% sequence identity with the amino acid sequences of SEQ ID NOs: 47, 48, 49, 50, 51, 52, 53, 54, 55, 56, 57, 58, 59, 60, 61, 62, 63, 64, 65, 66, 67, 68, 69, 70, 71, 72, and/or 73 and canine antibody heavy chain IgG comprising one to six different CDRs comprising at least 80%, 85%, 90%, 95%, 98% or 99% sequence identity with the amino acid sequences of SEQ ID NOs: 74, 75, 76, 77, 78, 79, 80, 81, 82, 83, 84, 85, 87, 88, 89, 90, 91, 92, 93, 94, 95, 96, 97, 98, 99, and/or 100, while still exhibiting the desired binding and functional properties. In another embodiment the antibody or antigen binding fragment of the present invention comprises a canine frame comprising a combination of IgG heavy chain sequence with a kappa light chain having one or more of the above-mentioned CDR amino acid sequences with 0, 1, 2, 3, 4, or 5 conservative or non-conservative amino acid substitutions, while still exhibiting the desired binding and functional properties.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed "Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table 1 directly below.

TABLE 1

Exemplary Conservative Amino Acid Substitutions

| Original residue | Conservative substitution |
|---|---|
| Ala (A) | Gly; Ser; |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specifity. Such variants include, but are not limited to, replacement of an amino acid with one having similar properties, such as the conservative amino acid substitutions of Table 1 above.

Nucleic Acids

The present invention further comprises the nucleic acids encoding the immunoglobulin chains of murine anti-canine IL-4R$_\alpha$ and/or caninized murine anti-canine IL-4R$_\alpha$ antibodies and antigen binding fragments thereof disclosed herein (see Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the CDRs and antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

As used herein, nucleotide and amino acid sequence percent identity can be determined using C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); *Natl. Biomed. Res. Found.*, Washington, DC; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), *Natl. Biomed. Res. Found.*, Washington, DC; Altschul, S. F., *J. Mol. Biol.* 219:555-565 (1991); States, D. J., et al., *Methods* 3:66-70(1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, New York (1997).

This present invention also provides expression vectors comprising the isolated nucleic acids of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

Epitope Binding and Binding Affinity

The present invention further provides antibodies or antigen binding fragments thereof that bind to amino acid residues of the same epitope of canine IL-4R$_\alpha$ as the murine anti-canine IL-4R$_\alpha$ antibodies disclosed herein. In particular embodiments the murine anti-canine IL-4R$_\alpha$ antibodies or antigen binding fragments thereof are also capable of inhibiting/blocking the binding of canine IL-4 and canine IL-13 to the type-I and/or type II IL-4 receptors.

A caninized murine anti-canine IL-4R$_\alpha$ antibody can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the murine anti-canine IL-4R$_\alpha$ antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_v$ fragment is a $V_L$ or $V_H$ region.

In one embodiment, the antibody or antigen binding fragment comprises a heavy chain constant region, e.g., a canine constant region, such as IgG-A, IgG-B, IgG-C and IgG-D canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation, the canine heavy chain constant region can be from IgG-B and the canine light chain constant region can be from kappa.

Antibody Engineering

Caninized murine anti-canine IL-4R$_\alpha$ antibodies of the present invention can be engineered to include modifications to canine framework and/or canine frame residues within the variable domains of a parental (i.e., canine) monoclonal antibody, e.g. to improve the properties of the antibody.

Experimental and Diagnostic Uses

Murine anti-canine IL-4R$_\alpha$ and/or caninized murine anti-canine IL-4R$_\alpha$ antibodies or antigen-binding fragments thereof of the present invention may also be useful in diagnostic assays for canine IL-4R$_\alpha$ protein, e.g., detecting its expression in conjunction with and/or relation to atopic dermatitis.

For example, such a method comprises the following steps:
(a) coat a substrate (e.g., surface of a microtiter plate well, e.g., a plastic plate) with a murine anti-canine IL-4R$_\alpha$ antibody or an antigen-binding fragment thereof;
(b) apply a sample to be tested for the presence of canine IL-4R$_\alpha$ to the substrate;
(c) wash the plate, so that unbound material in the sample is removed;
(d) apply detectably labeled antibodies (e.g., enzyme-linked antibodies) which are also specific to the IL-4R$_\alpha$ antigen;
(e) wash the substrate, so that the unbound, labeled antibodies are removed;
(f) if the labeled antibodies are enzyme linked, apply a chemical which is converted by the enzyme into a fluorescent signal; and
(g) detect the presence of the labeled antibody.

In a further embodiment, the labeled antibody is labeled with peroxidase which react with ABTS [e.g., 2,2'-azino-bis (3-ethylbenzthiazoline-6-sulphonic acid)] or 3,3',5,5'-Tetramethylbenzidine to produce a color change which is detectable. Alternatively, the labeled antibody is labeled with a detectable radioisotope (e.g., $^3$H) which can be detected by scintillation counter in the presence of a scintillant. Murine anti-canine IL-4R$_\alpha$ antibodies of the invention may be used in a Western blot or immuno protein blot procedure.

Such a procedure forms part of the present invention and includes for example:

(i) contacting a membrane or other solid substrate to be tested for the presence of bound canine IL-4R$_\alpha$ or a fragment thereof with a murine anti-canine IL-4R$_\alpha$ antibody or antigen-binding fragment thereof of the present invention. Such a membrane may take the form of a nitrocellulose or vinyl-based [e.g., polyvinylidene fluoride (PVDF)] membrane to which the proteins to be tested for the presence of canine IL-4R$_\alpha$ in a nondenaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the murine anti-canine IL-4R$_\alpha$ antibody or antigen-binding fragment thereof, the membrane is optionally blocked, e.g., with non-fat dry milk or the like so as to bind non-specific protein binding sites on the membrane.

(ii) washing the membrane one or more times to remove unbound murine anti-canine IL-4R$_\alpha$ antibody or an antigen-binding fragment thereof and other unbound substances; and (iii) detecting the bound murine anti-canine IL-4R$_\alpha$ antibody or antigen-binding fragment thereof.

Detection of the bound antibody or antigen-binding fragment may be by binding the antibody or antigen-binding fragment with a secondary antibody (an anti-immunoglobulin antibody) which is detectably labeled and, then, detecting the presence of the secondary antibody.

The murine anti-canine IL-4R$_\alpha$ antibodies and antigen-binding fragments thereof disclosed herein may also be used for immunohistochemistry. Such a method forms part of the present invention and comprises, e.g., (1) contacting a cell to be tested for the presence of canine IL-4R$_\alpha$ with a murine anti-canine IL-4R$_\alpha$ antibody or antigen-binding fragment thereof of the present invention; and (2) detecting the antibody or fragment on or in the cell. If the antibody or antigen-binding fragment itself is detectably labeled, it can be detected directly. Alternatively, the antibody or antigen-binding fragment may be bound by a detectably labeled secondary antibody which is detected.

Imaging techniques include SPECT imaging (single photon emission computed tomography) or PET imaging (positron emission tomography). Labels include e.g., iodine-123 ($^{123}$1) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 [See e.g., Gordon et al., *International Rev. Neurobiol.* 67:385-440 (2005)].

Cross-Blocking Antibodies

Furthermore, an anti-canine IL-4R$_\alpha$ antibody or antigen-binding fragment thereof of the present invention includes any antibody or antigen-binding fragment thereof that binds to the same epitope in canine IL-4R$_\alpha$ to which the antibodies and fragments discussed herein bind and any antibody or antigen-binding fragment that cross-blocks (partially or fully) or is cross-blocked (partially or fully) by an antibody or fragment discussed herein for canine IL-4R$_\alpha$ binding; as well as any variant thereof.

The cross-blocking antibodies and antigen-binding fragments thereof discussed herein can be identified based on their ability to cross-compete with the antibodies disclosed herein (on the basis of the CDRs as provided below in Example 5), i.e., 1A3, 1A9, 1B12, 10C12, 10F2, 10E10, 10G8, and/or 11D3; or more particularly, 11B6 and/or 6C12; and even more particularly 4D8, 4H3, 2E2, and/or 11H2, in standard binding assays (e.g., BIACore®, ELISA, as exemplified below, or flow cytometry). For example, standard ELISA assays can be used in which a recombinant canine IL-4R$_\alpha$ protein is immobilized on the plate, one of the antibodies is fluorescently labeled and the ability of non-labeled antibodies to compete off the binding of the labeled antibody is evaluated. Additionally or alternatively, BIAcore® analysis can be used to assess the ability of the antibodies to cross-compete. The ability of a test antibody to inhibit the binding of, for example, 1A3, 1A9, 1B12, 10C12, 10F2, 10E10, 10G8, and/or 11D3; or more particularly, 11B6 and/or 6C12; and even more particularly 4D8, 4H3, 2E2, and/or 11H2, to canine IL-4R$_\alpha$ demonstrates that the test antibody can compete with 1A3, 1A9, 1B12, 10C12, 10F2, 10E10, 10G8, 11D3, 11B6, 6C12, 4D8, 4H3, 2E2, and/or 11H2 for binding to canine IL-4R$_\alpha$ and thus, may, in some cases, bind to the same epitope on canine IL-4R$_\alpha$ as 1A3, 1A9, 1B12, 10C12, 10F2, 10E10, 10G8, 11D3, 11B6, 6C12, 4D8, 4H3, 2E2, and/or 11H2. As stated above, antibodies and fragments that bind to the same epitope as any of the anti-canine IL-4R$_\alpha$ antibodies or fragments of the present invention also form part of the present invention.

Pharmaceutical Compositions and Administration

To prepare pharmaceutical or sterile compositions of a caninized murine anti-canine IL-4R$_\alpha$ antibody or antigen binding fragment thereof it can be admixed with a pharmaceutically acceptable carrier or excipient. [See, e.g., *Remington's Pharmaceutical Sciences* and *U.S. Pharmacopeia: National Formulary*, Mack Publishing Company, Easton, PA (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets,* Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY]. In one embodiment, anti-IL-4R$_\alpha$ antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the LD$_{50}$ (the dose lethal to 50% of the population) and the ED$_{50}$ (the dose therapeutically effective in 50% of the population). The dose ratio between toxic and therapeutic effects is the therapeutic index (LD$_{50}$/ED$_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the murine anti-canine IL-4R$_\alpha$ antibody or antigen binding fragment thereof can be administered by an invasive route such as by injection. In further embodiments of the invention, a murine anti-canine IL-4R$_\alpha$ antibody or antigen binding fragment thereof, or pharmaceutical composition thereof, is administered intravenously, subcutaneously, intramuscularly, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion.

Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer a murine anti-canine or a caninized murine anti-canine IL-4R$_\alpha$ antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis*, Marcel Dekker, New York, NY (1991); Bach (ed.) *Monoclonal Antibodies and Peptide Therapy in Autoimmune Diseases*, Marcel Dekker, New York, NY (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies or antigen binding fragments thereof disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of a caninized murine anti-canine IL-4R$_\alpha$ antibody in the subject's serum, such as 0.1, 0.3, 1, 3, 10, 30, 100, 300 µg/ml or more. In other embodiments, a caninized murine anti-canine IL-4R$_\alpha$ antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

The antigenic peptides recognized by anti-canine IL-4R$_\alpha$ mAbs also may be used as vaccines to elicit antibodies that block the binding of canine IL-4 and canine IL-13 to the type-I and type II IL-4 receptors. Such vaccines may be useful as therapeutic vaccines for diseases such as atopic dermatitis. In order to use these antigenic peptides as vaccines, one or more of these peptides may be coupled chemically or through the techniques of recombinant DNA technology to another carrier protein in order to enhance the immunogenicity of these peptides and elicit peptide-specific antibodies. Techniques for coupling peptides to carrier proteins are known to those skilled in the art. Peptide vaccines may be used to vaccinate animals by IM, S/C, oral, spray or in ovo routes. Peptide vaccines may be used as subunit proteins expressed from bacterial, viral, yeast or baculovirus virus systems. Alternatively such peptide vaccines may be delivered following administration of a variety of viral or bacterial vectors that express such peptide vaccines as can be practiced by methods known to those skilled in the art. The peptide vaccines may be administered in doses from 1-1000 µg and may optionally contain an adjuvant and an acceptable pharmaceutical carrier.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a caninized murine anti-canine IL-4R$_\alpha$ antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Other Combination Therapies

As previously described, a caninized murine anti-canine IL-4R$_\alpha$ antibody or antigen binding fragment thereof and/or an antigenic peptide of the present invention may be coadministered with one or other more therapeutic agents (such as an inhibitor as discussed in the next paragraph) and/or a murine (or caninized murine) anti-canine TSLP antibody [see, U.S. Pat. No. 8,791,242]. The antibod(ies) may be linked to the agent (as an immunocomplex) and/or can be administered separately from the agent or other antibody. In the latter case (separate administration), the antibodies can be administered before, after or concurrently with the agent or can be coadministered with other known therapies.

Kits

Further provided are kits comprising one or more components that include, but are not limited to, an antibody or antigen binding fragment, as discussed herein, which specifically binds IL-4R$_\alpha$ (e.g., a caninized murine anti-canine IL-4R$_\alpha$ antibody or antigen binding fragment thereof) in association with one or more additional components including, but not limited to a pharmaceutically acceptable carrier and/or an inhibitor such as a Janus kinase (JAK) inhibitor, e.g., oclacitinib [see, WO 2013/040241], a spleen tyrosine kinase (SYK) inhibitor [see e.g., U.S. Pat. No. 8,759,366], or an antagonist to a chemoattractant receptor-homologous molecule expressed on TH2 cells [see e.g., WO 2010/099039; WO 2010/031183; and U.S. Pat. No. 8,546,422]. The binding composition and/or an inhibitor, as described directly above, can be formulated as a pure composition or in combination with a pharmaceutically acceptable carrier, in a pharmaceutical composition.

In one embodiment, the kit includes a binding composition of the present invention (e.g., a caninized murine anti-canine IL-4R$_\alpha$ or a pharmaceutical composition thereof in one container (e.g., in a sterile glass or plastic vial) and a pharmaceutical composition thereof and/or an inhibitor as described above in another container (e.g., in a sterile glass or plastic vial).

If the kit includes a pharmaceutical composition for parenteral administration to a subject, the kit can also include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Identification and Cloning of Canine IL-4 Receptor α Chain Receptor

The cDNA encoding a predicted full length canine IL-4 receptor alpha chain (SEQ ID NO: 1) was identified through a search of the Genbank database (accession #XM_547077.4; see also, U.S. Pat. No. 7,208,579 B2). This predicted cDNA encodes an 823 amino acids (SEQ ID NO: 2) including a 25 amino acid leader sequence and is identified as accession #XP_547077.3. The mature predicted canine IL-4 receptor α chain protein (SEQ ID NO: 4) shares 65% identity with human IL-4 receptor α chain (accession #NP_000409.1) and 70% identity with swine IL-4 receptor α chain (accession #NP_999505.1). The mature predicted canine IL-4 receptor α chain protein is encoded by the nucleotide sequence identified as SEQ ID NO: 3. Comparison of the predicted mature IL-4 receptor α chain with the known sequences of human IL-4 receptor α chain identified the extracellular domain (ECD) of the mature canine IL-4 receptor α chain protein and is designated as SEQ ID NO: 6. The DNA sequence encoding the ECD of the mature canine IL-4 receptor α chain is identified as SEQ ID NO: 5.

```
Canine IL-4 receptor α chain full length DNA with signal sequence
(SEQ ID NO: 1):
atgggcagactgtgcagcggcctgaccttccccgtgagctgcctggtgctggtgtgggtggccagcagcggcagcgtg aaggtgctgcacgagcccagctgcttcagcgactacatcagcaccagcgtgtgccagtggaagatggaccaccccacc aactgcagcgccgagctgagactgagctaccagctggacttcatgggcagcgagaaccacacctgcgtgcccgagaac agagaggacagcgtgtgcgtgtgcagcatgcccatcgacgacgccgtggaggccgacgtgtaccagctggacctgtgg gccggccagcagctgctgtggagcggcagcttccagcccagcaagcacgtgaagcccagaaccccgggcaacctgacc gtgcaccccaacatcagccacacctggctgctgatgtggaccaaccctaccccaccgagaaccacctgcacagcgag ctgacctacatggtgaacgtgagcaacgacaacgaccccgaggacttcaaggtgtacaacgtgacctacatgggcccc accctgagactggccgccagcaccctgaagagcggcgcagctacagcgccagagtgagagcctgggcccagacctac aacagcacctggagcgactggagccccagcaccacctggctgaactactacgagccctgggagcagcacctgcccctg ggcgtgagcatcagctgcctggtgatcctggccatctgcctgagctgctacttcagcatcatcaagatcaagaagggc tggtgggaccagatccccaaccccgccacagcccctgtggccatcgtgatccaggacagccaggtgagcctgtgg ggcaagagaagcagaggccaggagcccgccaagtgcccccactggaagacctgcctgaccaagctgctgccctgcctg ctggagcacggcctgggcagagaggaggagagccccaagaccgccaagaacggcccctgcagggcccggcaagccc gcctggtgccccgtggaggtgagcaagaccatcctgtggcccgagagcatcagcgtggtgcagtgcgtggagctgagc gaggcccccgtggacaacgaggaggaggaggaggtggaggaggacaagagaagcctgtgcccagcctggagggcagc ggcggcagcttccaggagggcagagagggcatcgtggccagactgaccgagagcctgttcctggacctgctgggcggc gagaacggcggcttctgccccagggcctggaggagagctgcctgccccccccagcggcagcgtgggcgcccagatg ccctgggcccagttccccagagccggccccagagccgcccccgagggccccgagcagcccagaagacccgagagcgcc ctgcaggccagccccaccagagcgccggcagcagcgccttccccgagccccccccgtggtgaccgacaaccccgcc tacagaagcttcggcagcttcctgggccagagcagcgaccccggcgacggcgacagcgaccccgagctggccgacaga cccggcgaggccgaccccggcatccccagcgccccccagcccccgagccccgcgccctgcagcccgagcccgag agctgggagcagatcctgagacagagcgtgctgcagcacagagccgccccgcccccggccccggccccggcagcggc tacagagttcacctgcgccgtgaagcagggcagcgcccccgacgccggcggccccggcttcggcccagcggcgag gccggctacaaggccttctgcagcctgctgcccggcggcgccacctgccccggcaccagcggcggcgaggccggcagc ggcgagggcggctacaagcccttccagagcctgaccccggctgccccggcgccccaccccgtgccgtgcccctg ttcaccttcggcctggacaccgagcccccggcagcccccaggacagcctgggcgccggcagcagccccgagcacctg ggcgtggagcccgccggcaaggaggaggacagcagaaagaccctgctggccccgagcaggccaccgaccccctgaga gacgacctggccagcagcatcgtgtacagcgccctgacctgccacctgtgcggccacctgaagcagtggcacgaccag gaggagagaggcaaggcccacatcgtgcccagccctgctgcggctgctgctgcggcgacagaagcagcctgctgctg agcccctgagagcccccaacgtgctgcccggcggcgtgctgctggaggccagcctgagcccgccagcctggtgccc agcggcgtgagcaaggagggcaagagcagcccttcagccagcccgccagcagcagcgcccagagcagcagccagacc cccaagaagctggccgtgctgagcaccgagcccacctgcatgagcgccagc Canine IL-4 receptor α full length protein with signal sequence in bold font
(SEQ ID NO: 2).
MGRLCSGLTFPVSCLVLVWVASSGSVKVLHEPSCFSDYISTSVCQWKMDHPTNCSAELRLSYQLDFMGSENHTCVPEN

REDSVCVCSMPIDDAVEADVYQLDLWAGQQLLWSGSFQPSKHVKPRTPGNLTVHPNISHTWLLMWTNPYPTENHLHSE

LTYMVNVSNDNDPEDFKVYNVTYMGPTLRLAASTLKSGASYSARVRAWAQTYNSTWSDWSPSTTWLNYYEPWEQHLPL

GVSISCLVILAICLSCYFSIIKIKKGWWDQIPNPAHSPLVAIVIQDSQVSLWGKRSRGQEPAKCPHWKTCLTKLLPCL
```

-continued

LEHGLGREEESPKTAKNGPLQGPGKPAWCPVEVSKTILWPESISVVQCVELSEAPVDNEEEEEVEEDKRSLCPSLEGS

GGSFQEGREGIVARLTESLELDLLGGENGGFCPQGLEESCLPPPSGSVGAQMPWAQFPRAGPRAAPEGPEQPRRPESA

LQASPTQSAGSSAFPEPPPVVTDNPAYRSEGSFLGQSSDPGDGDSDPELADRPGEADPGIPSAPQPPEPPAALQPEPE

SWEQILRQSVLQHRAAPAPGPGPSGYREFTCAVKQGSAPDAGGPGFGPSGEAGYKAFCSLLPGGATCPGTSGGEAGS

GEGGYKPFQSLTPGCPGAPTPVPVPLFTFGLDTEPPGSPQDSLGAGSSPEHLGVEPAGKEEDSRKTLLAPEQATDPLR

DDLASSIVYSALTCHLCGHLKQWHDQEERGKAHIVPSPCCGCCCGDRSSLLLSPLRAPNVLPGGVLLEASLSPASLVP

SGVSKEGKSSPFSQPASSSAQSSSQTPKKLAVLSTEPTCMSAS

Canine IL-4 receptor mature full length protein without signal sequence
(SEQ ID NO: 4)
VKVLHEPSCFSDYISTSVCQWKMDHPTNCSAELRLSYQLDFMGSENHTCVPENREDSVCVCSMPIDDAVEADVYQLDL

WAGQQLLWSGSFQPSKHVKPRTPGNLTVHPNISHTWLLMWTNPYPTENHLHSELTYMVNVSNDNDPEDFKVYNVTYMG

PTLRLAASTLKSGASYSARVRAWAQTYNSTWSDWSPSTTWLNYYEPWEQHLPLGVSISCLVILAICLSCYFSIIKIKK

GWWDQIPNPAHSPLVAIVIQDSQVSLWGKRSRGQEPAKCPHWKTCLTKLLPCLLEHGLGREEESPKTAKNGPLQGPGK

PAWCPVEVSKTILWPESISVVQCVELSEAPVDNEEEEEVEEDKRSLCPSLEGSGGSFQEGREGIVARLTESLFLDLLG

GENGGFCPQGLEESCLPPPSGSVGAQMPWAQFPRAGPRAAPEGPEQPRRPESALQASPTQSAGSSAFPEPPPVVTDNP

AYRSFGSFLGQSSDPGDGDSDPELADRPGEADPGIPSAPQPPEPPAALQPEPESWEQILRQSVLQHRAAPAPGPGPGS

GYREFTCAVKQGSAPDAGGPGFGPSGEAGYKAFCSLLPGGATCPGTSGGEAGSGEGGYKPFQSLTPGCPGAPTPVPVP

LFTFGLDTEPPGSPQDSLGAGSSPEHLGVEPAGKEEDSRKTLLAPEQATDPLRDDLASSIVYSALTCHLCGHLKQWHD

QEERGKAHIVPSPCCGCCCGDRSSLLLSPLRAPNVLPGGVLLEASLSPASLVPSGVSKEGKSSPFSQPASSSAQSSSQ

TPKKLAVLSTEPTCMSAS

Canine IL-4 receptor mature full length DNA without signal sequence
(SEQ ID NO: 3)
gtgaaggtgctgcacgagcccagctgcttcagcgactacatcagcaccagcgtgtgccagtggaagatggaccacccc accaactgcagcgccgagctgagactgagctaccagctggacttcatgggcagcgagaaccacacctgcgtgcccgag aacagagaggacagcgtgtgcgtgtgcagcatgcccatcgacgacgccgtggaggccgacgtgtaccagctggacctg tgggccggccagcagctgctgtggagcggcagcttccagcccagcaagcacgtgaagcccagaaccccccggcaacctg accgtgcaccccaacatcagccacacctggctgctgatgtggaccaaccccaccccaccgagaaccacctgcacagc gagctgacctacatggtgaacgtgagcaacgacaacgaccccgaggacttcaaggtgtacaacgtgacctacatgggc cccaccctgagactggccgccagcaccctgaagagcggcgccagctacagcgccagagtgagagcctgggcccagacc tacaacagcacctggagcgactggagccccagcaccacctggctgaactactacgagccctgggagcagcacctgccc ctgggcgtgagcatcagctgcctggtgatcctggccatctgcctgagctgctacttcagcatcatcaagatcaagaag ggctggtgggaccagatccccaaccccgcccacagcccctggtggccatcgtgatccaggacagccaggtgagcctg tggggcaagagaagcagaggccaggagcccgccaagtgcccccactggaagacctgcctgaccaagctgctgccctgc ctgctggagcacggcctgggcagagaggaggagagccccaagaccgccaagaacggccccctgcagggccccggcaag cccgcctggtgccccgtggaggtgagcaagaccatcctgtggcccgagagcatcagcgtggtgcagtgcgtggagctg agcgaggcccccgtggacaacgaggaggaggaggaggtggaggaggacaagagaagcctgtgccccagcctggagggc agcggcggcagcttccaggagggcagagagggcatcgtggccagactgaccgagagcctgttcctggacctgctgggc ggcgagaacggcggcttctgcccccagggcctggaggagagctgcctgccccccccagcggcagcgtgggcgcccag atgccctgggcccagttccccagagccggccccagagccgcccccgagggccccgagcagcccagaagacccgagagc gccctgcaggccagccccacccagagcgccggcagcagcgccttccccgagcccccccccgtggtgaccgacaacccc gcctacagaagcttcggcagcttcctgggccagagcagcgacccccggcgacggcgacagcgaccccgagctggccgac agacccggcgaggccgaccccggcatccccagcgccccccagccccccgagccccccgccgccctgcagcccgagccc gagagctgggagcagatcctgagacagagcgtgctgcagcacagagccgcccccgccccccggccccggccccggcagc -continued

```
ggctacagagagttcacctgcgccgtgaagcagggcagcgccccgacgccggcggccccggcttcggcccccagcggc gaggccggctacaaggccttctgcagcctgctgcccggcggcgccacctgccccggcaccagcggcggcgaggccggc agcggcgagggcggctacaagcccttccagagcctgaccccggctgccccggcgccccacccccgtgccccgtgccc ctgttcaccttcggcctggacaccgagccccggcagccccaggacagcctgggcgccggcagcagcccgagcac ctgggcgtggagcccgccggcaaggaggaggacagcagaaagaccctgctggcccccgagcaggccaccgacccctg agagacgacctggccagcagcatcgtgtacagcgccctgacctgccacctgtgcggccacctgaagcagtggcacgac caggaggagagaggcaaggcccacatcgtgcccagcccctgctgcggctgctgctgcggcgacagaagcagcctgctg ctgagcccctgagagcccccaacgtgctgcccggcggcgtgctgctggaggccagcctgagccccgccagcctggtg cccagcggcgtgagcaaggagggcaagagcagcccttcagccagcccgccagcagcagcgcccagagcagcagccag accccaagaagctggccgtgctgagcaccgagcccacctgcatgagcgccagc
```

Canine IL-4 receptor α chain extracellular protein domain without the signal
sequence (SEQ ID NO: 6):
VKVLHEPSCFSDYISTSVCQWKMDHPTNCSAELRLSYQLDFMGSENHTCVPENREDSVCVCSMPIDDAVEADVYQLDL

WAGQQLLWSGSFQPSKHVKPRTPGNLTVHPNISHTWLLMWTNPYPTENHLHSELTYMVNVSNDNDPEDFKVYNVTYMG

PTLRLAASTLKSGASYSARVRAWAQTYNSTWSDWSPSTTWLNYYEPWEQHLP

Canine IL-4 receptor α chain extracellular DNA domain without the signal
sequence (SEQ ID NO: 5):
```
gtgaaggtgctgcacgagcccagctgcttcagcgactacatcagcaccagcgtgtgccagtggaagatggaccacccc accaactgcagcgccgagctgagactgagctaccagctggacttcatgggcagcgagaaccacacctgcgtgcccgag aacagagaggacagcgtgtgcgtgtgcagcatgcccatcgacgacgccgtggaggccgacgtgtaccagctggacctg tgggccggccagcagctgctgtggagcggcagcttccagcccagcaagcacgtgaagcccagaaccccggcaacctg accgtgcaccccaacatcagccacacctggctgctgatgtggaccaacccctaccccaccgagaaccacctgcacagc gagctgacctacatggtgaacgtgagcaacgacaacgaccccgaggacttcaaggtgtacaacgtgacctacatgggc cccaccctgagactggccgccagcaccctgaagagcggcgccagctacagcgccagagtgagagcctgggcccagacc tacaacagcacctggagcgactggagcccagcaccacctggctgaactactacgagccctgggagcagcacctgccc
```

Canine IL-4 receptor α chain extracellular domain with a c-terminal 8 HIS Tag
(SEQ ID NO: 8):
VKVLHEPSCFSDYISTSVCQWKMDHPTNCSAELRLSYQLDFMGSENHTCVPENREDSVCVCSMPIDDAVEADVYQLDL

WAGQQLLWSGSFQPSKHVKPRTPGNLTVHPNISHTWLLMWTNPYPTENHLHSELTYMVNVSNDNDPEDFKVYNVTYMG

PTLRLAASTLKSGASYSARVRAWAQTYNSTWSDWSPSTTWLNYYEPWEQHLPHHHHHHHH

Canine IL-4 receptor α chain extracellular DNA domain with a c-terminal 8 HIS
Tag (SEQ ID NO: 7):
```
gtgaaggtgctgcacgagcccagctgcttcagcgactacatcagcaccagcgtgtgccagtggaagatggaccacccc accaactgcagcgccgagctgagactgagctaccagctggacttcatgggcagcgagaaccacacctgcgtgcccgag aacagagaggacagcgtgtgcgtgtgcagcatgcccatcgacgacgccgtggaggccgacgtgtaccagctggacctg tgggccggccagcagctgctgtggagcggcagcttccagcccagcaagcacgtgaagcccagaaccccggcaacctg accgtgcaccccaacatcagccacacctggctgctgatgtggaccaacccctaccccaccgagaaccacctgcacagc gagctgacctacatggtgaacgtgagcaacgacaacgaccccgaggacttcaaggtgtacaacgtgacctacatgggc cccaccctgagactggccgccagcaccctgaagagcggcgccagctacagcgccagagtgagagcctgggcccagacc tacaacagcacctggagcgactggagcccagcaccacctggctgaactactacgagccctgggagcagcacctgccc caccaccaccaccaccaccac
```

Canine IL-4 receptor α chain extracellular domain plus human IgG1 Fc
(SEQ ID NO: 10):
VKVLHEPSCFSDYISTSVCQWKMDHPTNCSAELRLSYQLDFMGSENHTCVPENREDSVCVCSMPIDDAVEADVYQLDL

WAGQQLLWSGSFQPSKHVKPRTPGNLTVHPNISHTWLLMWTNPYPTENHLHSELTYMVNVSNDNDPEDFKVYNVTYMG

-continued

```
PTLRLAASTLKSGASYSARVRAWAQTYNSTWSDWSPSTTWLNYYEPWEQHLEPKSCDKTHTCPPCPAPELLGGPSVFL

FPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Canine IL-4 receptor α chain extracellular DNA domain plus human IgG1 Fc
(SEQ ID NO: 9):

```
gtgaaggtgctgcacgagcccagctgcttcagcgactacatcagcaccagcgtgtgccagtggaagatggaccacccc accaactgcagcgccgagctgagactgagctaccagctggacttcatgggcagcgagaaccacacctgcgtgcccgag aacagagaggacagcgtgtgcgtgtgcagcatgcccatcgacgacgccgtggaggccgacgtgtaccagctggacctg tgggccggccagcagctgctgtggagcggcagcttccagcccagcaagcacgtgaagcccagaaccccggcaacctg accgtgcaccccaacatcagccacacctggctgctgatgtggaccaaccccaccaccgagaaccacctgcacagc gagctgacctacatggtgaacgtgagcaacgacaacgaccccgaggacttcaaggtgtacaacgtgacctacatgggc cccaccctgagactggccgccagcaccctgaagagcggcgccagctacagcgccagagtgagagcctgggcccagacc tacaacagcacctggagcgactggagcccagcaccacctggctgaactactacgagcctgggagcagcacctggag cccaagagctgcgacaagacccacacctgccccccctgccccgcccccgagctgctgggcggcccagcgtgttcctg ttccccccaagcccaaggacaccctgatgatcagcagaaccccgaggtgacctgcgtggtggtggacgtgagccac gaggaccccgaggtgaagttcaactggtacgtggacggcgtggaggtgcacaacgccaagaccaagcccagagaggag cagtacaacagcacctacagagtggtgagcgtgctgaccgtgctgcaccaggactggctgaacggcaaggagtacaag tgcaaggtgagcaacaaggccctgcccgcccccatcgagaagaccatcagcaaggccaagggccagcccagagagccc caggtgtacaccctgcccccagcagagacgagctgaccaagaaccaggtgagcctgacctgcctggtgaagggcttc taccccagcgacatcgccgtggagtgggagagcaacggccagcccgagaacaactacaagaccaccccccccgtgctg gacagcgacggcagcttcttcctgtacagcaagctgaccgtggacaagagcagatggcagcagggcaacgtgttcagc tgcagcgtgatgcacgaggcctgcacaaccactacacccagaagagcctgagcctgagccccggcaag
```

Example 2

Murine Anti-Canine IL-4 Receptor Alpha Chain Antibodies

Generation of Anti-Canine 11-4 Receptor α Chain Monoclonal Antibodies:

A total of three Balb/c mice were immunized multiple times (with 10 μg each time) over a 17 day period. The immunizing antigen was the canine IL-4 R alpha chain extracellular domain (ECD)-human Fc fusion protein. Following immunization, serum was collected from each mouse and tested for reactivity with canine IL-4 receptor alpha chain ECD HIS-tagged protein. The spleen cells of the mouse with the highest serum anti-IL-4 receptor alpha chain ECD titer were fused to the myeloma P3X63Ag8.653 cell line. Approximately 2 weeks following fusion, supernatant from putative hybridoma cells were tested by ELISA for their reactivity to the IL-4 receptor alpha chain ECD HIS-tagged protein. Hybridomas producing strong positive signals in the ELISA were subcloned by limiting dilution and tested again for reactivity to canine IL-4 receptor alpha chain ECD HIS-tagged protein.

Confirmation of Monoclonal Antibodies Reactivity Against Canine IL-4 Receptor α Chain:

The reactivity of antibodies secreted by hybridomas to ECD of canine IL-4 receptor alpha chain was confirmed by ELISA. Hybridoma cells were cultured using CELLine bioreactors (Integra-biosciences) for 10-30 days. Cells were initially maintained in DMEM supplemented with 4 mM L-glutamine and 10% Ultra Low IgG fetal bovine serum (FBS) from Gibco. Hybridoma cells were seeded in CELLine bioreactor cell chambers at a cell density of approximately 2×10⁶ cells/mL in 15 mL of the same medium with the FBS concentration increased to 20%. The outer chamber was filled with 1 L of nutrient medium (DMEM with 4 mM L-glutamine and 2% standard FBS). Hybridoma cells in the cell chamber were expanded to approximately 2.5×10⁷ cells/mL over 3-7 days. Then, 10 mL of cell suspension was harvested from the cell chamber and replaced with fresh media to allow for re-expansion of cells and subsequent harvests. This procedure was repeated as necessary to obtain adequate amounts of mAb from each hybridoma clone. Harvested cell suspensions were centrifuged and the supernatants were filtered through 0.2 micron filter membranes. For antibody purification, each clone's supernatant was purified using a Protein G Sepharose 4 Fast flow 5 mL column (GE Healthcare) by gravity flow. After washing with Tris-EDTA (TE) buffer pH 8.0, bound antibodies were eluted using 0.1 M glycine buffer, pH 2.7, followed by pH neutralization using 1 M Tris, pH 8.0. Antibodies were concentrated and buffer exchanged into phosphate-buffered saline (PBS) using Centriprep YM-10 kDa NMWL centrifugal filter units (Millipore). Antibody concentrations were quantified using spectrophotometry. Purified anti-canine IL-4 receptor α chain mAbs were tested for reactivity with the HIS-tagged ECD domain of canine IL-4 receptor alpha chain by ELISA as follows: HIS-tagged canine IL-4 receptor alpha chain protein is diluted to 10 μg/mL in coating buffer (Carbonate/Bicarbonate pH 9.0) and dispensed at 100 μL/well in 96-well flat bottomed ELISA plates (NUNC). The plates are incubated at 4° C. overnight. The plates are then washed three times with phosphate buffered saline containing 0.05% Tween-20 (PBST). Next, 200 μl of blocking buffer (5% skim milk in PBST) is added to each well and the plates are incubated at 37° C. for 60 minutes. The plates are then washed three times with PBST. Next, 100 μl of test mAbs diluted in blocking buffer is added to the first wells of the appropriate columns. Test mAbs are then diluted threefold to the appropriate plate position. Following incubation of the plates at 37° C. for 60 minutes, the plates are washed three times with PBST. Next, 100 μl per well of a 1:2,000 dilution of a horseradish peroxidase conjugated goat anti-mouse IgG (KPL) is added to the plates, which are then incubated at 37° C. for 60 minutes. Then the plates are washed three times with PBST, and 100 μL/well of 3,3',5,5' tetramethyl benzidine, (TMB) substrate (from KPL) is added to the plates. The color reaction is allowed to develop for 5-20 minutes at 37° C. prior to measuring absorbance at 650 nm.

Various mouse anti-canine IL-4R$_\alpha$ monoclonal antibodies (mAbs) were assayed by ELISA for their ability to bind the extracellular domain of canine IL-4R$_\alpha$. As depicted in FIG. 1, a majority of these mAbs exhibit positive dosage-dependent binding.

Example 3

Identification of the DNA and Predicted Protein Sequences of the Heavy and Light Chains Variable Domains of Anti-Canine IL-4 Receptor Alpha Chain Monoclonal Antibodies The DNA sequence of mouse VH and VL chains are identified following isolation of mRNA from each hybridoma using standard molecular biology methods. The SEQ ID NOs. of the DNA and predicted amino acid sequences of the VH and VL from these hybridomas are listed below. The DNA encoding the signal sequence and the amino acids corresponding to predicted signal sequence are underlined, those corresponding to the CDRs are in bold, and the FRs are neither underlined nor in bold (i.e., signal sequence-FR1-CDR1-FR2-CDR2-FR3-CDR3-FR4).

```
mAb 1A3
Heavy chain: DNA sequence (SEQ ID NO: 11):
ATGGACTCCAGGCTCAATTTAGTTTTCCTTGTCCTTATTTTAAAAGGTGTCCGGTGTGAGGTGCAGCTGGTGGAGTCT

GGGGGAGACTTAGTGAAGCCTGGAGGGTCCCTGAAACTCTCCTGTGCAGCCTCTGGATTCACTTTCAGTGACTTTGGA

ATGCACTGGGTTCGTCAGGCTCCAGAGAAGGGGCTGGGGTGGGTTGCATACATTAGTAGTGGCAGTGGTACCATCTAC

TATGCAGACACAGTGAGGGGCCGATTCACCATCTCCAGAGACAATGTCAAGAACACCCTGTTCCTGCAAATGACCAGT

CTGAGGTCTGAGGACACGGCCATGTATTACTGTGTAAGGGGGGACCTTTACTACGGTAGTAGTTTCGATGCTTATTGG

GGCCGAGGGACTCTGGTCACTGTCTCTGCA

Heavy chain: Amino acid sequence (SEQ ID NO: 12):
MDSRLNLVFLVLILKGVRCEVQLVESGGDLVKPGGSLKLSCAASGFTFSDFGMHWVRQAPEKGLGWVAYISSGSGTIY

YADTVRGRFTISRDNVKNTLFLQMTSLRSEDTAMYYCVRGDLYYGSSFDAYWGRGTLVTVSA

Light chain: DNA sequence (SEQ ID NO: 13):
ATGGATTTTCAAGTGCAGATTTTCAGCTTCCTGCTAATCAGTGCTTCAGTCATAATGTCCAGAGGACAAATTGTTCTC

TCCCAGTCTCCAGCAATCCTGTCTGCATCTCCAGGGGAGAAGGTCACAATGACTTGCAGGGCCAGCTCAAGTGTAAGT

TTCATGTTCTGGTACCAGCAGAAGCCAGGATCCTCCCCCAAACCCTGGATTTATGACACATCCAACCTGGCTTCTGGA

GTCCCTGCTCGCTTCAGTGGCAGTGGGTCTGGGACCTCTTACTCTCTCACAATCAGCAGAGTGGAGGCTGAAGATGCT

GCCACTTATTACTGCCAGCAGTGGAGTAGTAACCCACTCACGTTCGGTGCTGGGACCAAGCTGGAGCTGAAA

Light chain: Amino acid sequence (SEQ ID NO: 14):
MDFQVQIFSFLLISASVIMSRGQIVLSQSPAILSASPGEKVTMTCRASSSVSFMFWYQQKPGSSPKPWIYDTSNLASG

VPARFSGSGSGTSYSLTISRVEAEDAATYYCQQWSSNPLTFGAGTKLELK mAb 1A9
Heavy chain: DNA sequence (SEQ ID NO: 15):
ATGGAATGGCCTTGTATCTTTCTCTTCCTCCTGTCAGTAACTGAAGGTGTCCACTCCCAGGTTCCGCTGCAGCAGTCT

GGACCTGAGCTGGTGAAGCCTGGGGCCTCAGTGAAGATTTCCTGCAAGGCTTCTGGCTACGCATTCAGTAGCTCCTGG

ATGAACTGGGTGAAGCAGAGGCCTGGAAAGGGTCTTGAGTGGATTGGACGGATTTATCCTGGAGATGGAGATACTAAG

TACAATGGGAAGTTCAAGGGCAAGGCCACACTGACTGCAGACAAATCCTCCAGCACAGCCTACATGCAACTCAGCAGC

CTGACATCGGAGGACTCTGCGGTTTACTTCTGTGCAAGAGATGATTACGACGAGGCTTCCTGGGGCCAAGGGACTCTG

GTCACTGTCTCTGCA

Heavy chain: Amino acid sequence (SEQ ID NO: 16):
MEWPCIFLFLLSVTEGVHSQVPLQQSGPELVKPGASVKISCKASGYAFSSSWMNWVKQRPGKGLEWIGRIYPGDGDTK

YNGKFKGKATLTADKSSSTAYMQLSSLTSEDSAVYFCARDDYDEASWGQGTLVTVSA
```

-continued

```
Light chain: DNA sequence (SEQ ID NO: 17):
ATGGGCATCAAGATGGAGTTTCAGACCCAGGTCTTTGTATTCGTGTTGCTCTGGTTGTCTGGTGTTGATGGAGACATT
GTGATGACCCAGTCTCAAAAATTCATGTCCACATCAGTAGGAGACAGGGTCAGCATCACCTGCAAGGCCAGTCAGAAT
GTTCGTTCTGCTGTAGCCTGGTATCAACAGAAACCAGGGCAGTCTCCTAAATCACTGATTTACTTGGCATCCAACCGG
CACACTGGAGTCCCTGATCGCTTCACAGGCAGTGGATCTGGGACAGATTTCACTCTCACCATTAGCAATGTGCAATCT
GAAGACCTGGCAGATTATTTCTGTCTGCAACATTGGAATTATCCATTCACGTTCGGCTCGGGGACAAAGTTGGAAATA
AAA Light chain: Amino acid sequence (SEQ ID NO: 18):
MGIKMEFQTQVFVFVLLWLSGVDGDIVMTQSQKFMSTSVGDRVSITCKASQNVRSAVAWYQQKPGQSPKSLIYLASNR
HTGVPDRFTGSGSGTDFTLTISNVQSEDLADYFCLQHWNYPFTFGSGTKLEIK mAb 1B12
Heavy chain: DNA sequence (SEQ ID NO: 19):
ATGGGATGGAGCTGGATCTTTCTCTTTCTCCTGTCAGGAACTGCAGGTGTCCTCTCTGAGGTCCAGCTGCAACAATCT
GGACCTGAGCTGGTGAAGCCTGGGGCTTCAGTGAAGATATCCTGTAAGGCTTCTGGATACACGTTCACTGACTATTAC
ATGAACTGGGTGAAGCAGAGCCATGGAAAGAGCCTTGAGTGGATTGGAGACATTATTCCTAGCAATGGTGGTACTAGC
TACAACCAGAAGTTCAAGGGCAAGGCCACATTGACTGTAGACAAGTCCTCCAGCGCAGCCTACATGGAGCTCCGCAGC
CTGACATCTGAGGACTCTGCAGTCTATTACTGTGCAAGAGGGATCAGCTACTATGGTAACGATATTACTTTACTATG
GACTATTGGGGTCAAGGAACCTCAGTCACCGTCTCCTCA Heavy chain: Amino acid sequence (SEQ ID NO: 20):
MGWSWIFLFLLSGTAGVLSEVQLQQSGPELVKPGASVKISCKASGYTFTDYYMNWVKQSHGKSLEWIGDIIPSNGGTS
YNQKFKGKATLTVDKSSSAAYMELRSLTSEDSAVYYCARGISYYGNRYYFTMDYWGQGTSVTVSS Light chain: DNA sequence (SEQ ID NO: 21):
ATGAGGTGCCTAGCTGAGTTCCTGGGGCTGCTTGTGCTCTGGATCCCTGGAGCCATTGGGGATATTGTGATGACTCAG
GCTGCACCCTCTGTACCTGTCACTCCTGGAGAGTCAGTATCCATCTCCTGCAGGTCTAGTAAGAGTCTCCTGCATAGT
AATGGCAACACTTACTTGTTTTGGTTCGTGCAGAGGCCAGGCCAGTCTCCTCAGCTCCTGATATATCGGATGTCCAAC
CTTGCCTCAGGAGTCCCAGACAGGTTCAGTGGCAGTGGGTCAGGAACTGCTTTCACACTGAGAATCAGTAGAGTGGAG
GCTGAGGATGTGGGTGTTTATTACTGTATGCAACATCTAGAATATCCATTCACGTTCGGCTCGGGGACAAAGTTGGAC
ATAAAA Light chain: Amino acid sequence (SEQ ID NO: 22):
MRCLAEFLGLLVLWIPGAIGDIVMTQAAPSVPVTPGESVSISCRSSKSLLHSNGNTYLFWFVQRPGQSPQLLIYRMSN
LASGVPDRFSGSGSGTAFTLRISRVEAEDVGVYYCMQHLEYPFTFGSGTKLDIK mAb 10C12
Heavy chain: DNA sequence (SEQ ID NO: 23):
ATGGAATGGAGCTGGATCTTTCTCTTCCTCCTGTCAGTAACTGCAGGTGTCCAATCCCAGGTTCAACTGCAGCAGTCT
GGGGCTGAGCTGGTGAGGCCTGGGGCTTCAGTGAAGCTGTCCTGCAAGGCTTCGGGCTACACATTTACTGACTATGAA
ATGCACTGTGTGAAGCAGACACCTGTGCACGGCCTGGAATGGATTGGAGCTATTGATCCTGAAACTTGTGGTACTGCC
TACAATCAGAAGTTCAAGGGCAAGGCCACACTGACTGCAGACAAATCCTCCAGCACAGCCTACATGGAGCTCCGCAGC
CTGACATCTGAGGACTCTGCCGTCTATTACTGTACAAGATCGAAACTGGGACGAGGGTGGTACTTCGATGTCTGGGGC
ACAGGGACCACGGTCACCGTCTCCTCA Heavy chain: Amino acid sequence (SEQ ID NO: 24):
MEWSWIFLFLLSVTAGVQSQVQLQQSGAELVRPGASVKLSCKASGYTFTDYEMHCVKQTPVHGLEWIGAIDPETCGTA
YNQKFKGKATLTADKSSSTAYMELRSLTSEDSAVYYCTRSKLGRGWYFDVWGTGTTVTVSS Light chain: DNA sequence (SEQ ID NO: 25):
ATGGAATCACAGACCCAGGTCCTCATGTTTCTTCTGCTCTGGGTATCTGGTGCCTGTGCAGACATTGTGATGACACAG
TCTCCATCCTCCCTGGCTATGTCAGTAGGACAGAAGGTCACTATGAGCTGCAAGTCCAGTCAGAGCCTTTTAAATAGT
AGCAATCAAAAGAACTATTTGGCCTGGTACCAGCAGAAACCAGGACAGTCTCCTAAACTTCTGGTATACTTTGCATCC
```

```
ACTAGGGAATCTGGGGTCCCTGATCGCTTCATAGGCAGTGGATCTGGGACAGATTTCACTCTTACCATCAGCAGTGTG

CAGGCTGAAGACCTGGCAGATTACTTCTGTCAGCAACATTATAGCACTCCGTACACGTTCGGAGGGGGGACCAAGCTG

GAAATAAAA
```

Light chain: Amino acid sequence (SEQ ID NO: 26):
MESQTQVLMFLLLWVSGACADIVMTQSPSSLAMSVGQKVTMSCKSSQSLLNSSNQKNYLAWYQQKPGQSPKLLVYFAS

TRESGVPDRFIGSGSGTDFTLTISSVQAEDLADYFCQQHYSTPYTFGGGTKLEIK mAb 10F2
Heavy chain: DNA sequence (SEQ ID NO: 27):
```
ATGGCTGTCCTGGCACTGCTCCTCTGCCTGGTGACATTCCCAAACTGTGTCCTGTCCCAGGTGCACCTGAAGGAGTCA

GGACCTGGCCTGGTGGCGCCCTCACAGAGCCTGTCCATCACATGCACTGTCTCAGGGTTCTCTTTAACCAGCTATGGT

GTAAGCTGGGTTCGCCAGCCTCCAGGAGAGGGTCTGGAGTGGCTGGGAGTAATATGGGGTGACGGGAGCACATATTTT

CATTCAGCTCTCATATCCAGACTGAGCATCAGCAAGGATGACTCCAAGAGCCAAGTTTTCTTAAAATTGAACAGTCTA

CAAACTGATGACACAGCCACGTACTACTGTGCCAAACAAGGGACGATCTATGATGGTTACTACAACTATGCTATGGAC

TACTGGGGTCAAGGAACCTCAGTCACCGTCTCCTCA
```

Heavy chain: Amino acid sequence (SEQ ID NO: 28):
MAVLALLLCLVTFPNCVLSQVHLKESGPGLVAPSQSLSITCTVSGFSLTSYGVSWVRQPPGEGLEWLGVIWGDGSTYF

HSALISRLSISKDDSKSQVFLKLNSLQTDDTATYYCAKQGTIYDGYYNYAMDYWGQGTSVTSS

Light chain: DNA sequence (SEQ ID NO: 29):
```
ATGGATTCACAGGCCCAGGTTCTTATGTTACTGCTGCTATGGGTATCTGGTACCTGTGGGGACATTGTGATGTCACAG

TCTCCATCCTCCCTAACTGTGTCAGTTGGAGAGAAGGTTACTATGAGCTGCAAGTCCAGTCAGAACCTTTTATATGGT

GGCAATCAAAAGAACTACTTGGCCTGGTACCAGCAGAAACCAGGGCAGTCTCCTAAACTGCTGATTTACTGGGCATCC

ACTAGGGAATCTGGGGTCCCTGATCGCTTCACAGGCAGTGGATCTGGGACAGATTTCACTCTCACCATCAGCAGTGTG

AGGGCTGAAGACCTGGCAGTTTATTACTGTCAGCAATATTATGACTATCCGTACACGTTCGGAGGGGGGACCAAGCTG

GAAATAAAA
```

Light chain: Amino acid sequence (SEQ ID NO: 30):
MDSQAQVLMLLLLWVSGTCGDIVMSQSPSSLTVSVGEKVTMSCKSSQNLLYGGNQKNYLAWYQQKPGQSPKLLIYWAS

TRESGVPDRFTGSGSGTDFTLTISSVRAEDLAVYYCQQYYDYPYTFGGGTKLEIK mAb 10E10
Heavy chain: DNA sequence (SEQ ID NO: 31):
```
ATGGGATGGAGCTGGATCTTTCTCTTCCTCCTGTCAGGAACTGCAGGTGTCCACTCCCAGGTTCAGCTGCAGCAGTCT

GGACCTGAGCTGGTGAAGCCTGGGGCTTCAGTGAAGTTGTCCTGCAAGGCTTCTGGCTACACCTTCACAACCTACGAT

ATACACTGGGTGAAGCAGAGGCCTGGGCAGGGCCTTGAGTGGATTGGATGGATTTATCCTAGAGATGGTCGTACTACT

TACAATGAGAAGTTCAAGGCCAAGGCCACATTGACTGTAGACACATCCTCCACCACAGCGTACATGGAGCTCCACAGC

CTGACATCTGAGGACTCTGCGGTCTATTTCTGTGCGAGAAGTAGCCCCTTTGGCTACTGGGGCCAAGGCACCACTCTC

ACAGTCTCCTCA
```

Heavy chain: Amino acid sequence (SEQ ID NO: 32):
MGWSWIFLFLLSGTAGVHSQVQLQQSGPELVKPGASVKLSCKASGYTFTTYDIHWVKQRPGQGLEWIGWIYPRDGRTT

YNEKFKAKATLTVDTSSTTAYMELHSLTSEDSAVYFCARSSPFGYWGQGTTLTVSS

Light chain: DNA sequence (SEQ ID NO: 33):
```
ATGAAGTTTCCTTCTCAACTTCTGCTCTTCCTGCTGTTCAGAATCACAGGCATAATATGTGACATCCAGATGACACAA

TCTTCATCCTACTTGTCTGTATCTCTAGGAGGCAGAGTCACCATTACTTGCAAGGCAAGTGACCACATTAATAATTGG

TTAGCCTGGTATCAGCAGAAACCAGGAAATGCTCCTAGGCTCTTAATATCTGGTGCAACCAGTTTGGAAACTGGGGTT

CCTTCAAGATTCAGTGGCAGTGGATCTGGAAAGGATTACACTCTCAGCATTACCAGTCTTCAGACTGAAGATGCTGCT

ACTTATCACTGTCACCAGTATTGGAGTATTCCGTACACGTTCGGAGGGGGGACCAAGGTGGAAATAAAA
```

Light chain: Amino acid sequence (SEQ ID NO: 34):
MKFPSQLLLFLLFRITGIICDIQMTQSSSYLSVSLGGRVTITCKASDHINNWLAWYQQKPGNAPRLLISGATSLETGV

PSRFSGSGSGKDYTLSITSLQTEDAATYHCHQYWSIPYTFGGGTKVEIK mAb 10G8
Heavy chain: DNA sequence (SEQ ID NO: 35):
ATGGAATGGAGCTGGGTCTTTCTCTTCCTCCTGTCAGTAATTGCAGGTGTCCAATCCCAGGTTCAACTGCAGCAGTCT GGGGCTGAGCTGGTGGGGCCTGGGGCTTCAGTGACGCTGTCCTGCAAGGCTTCGGGCTACACATTTACTGACTATGAA

ATGCACTGGGTGAAGCAGACACCTGTGCATGGCCTGGAATGCATTGGAGCTATTGATCCTGAAACTGGTGGTACTGCC

TACAATCAGAAGTTCAAGGGCAAGGCCATACTGACTGCAGACAAATCCTCTAGCACAGCCTACATGGAGCTCCGCAGC

CTGACATCTGAGGACTCTGCCGTCTATTACTGTCTAACTGGGTTTGACTACTGGGGCCAAGGCACCACTCTCACAGTC

TCCTCA

Heavy chain: Amino acid sequence (SEQ ID NO: 36):
MEWSWVFLFLLSVIAGVQSQVQLQQSGAELVGPGASVTLSCKASGYTFTDYEMHWVKQTPVHGLECIGAIDPETGTA

YNQKFKGKAILTADKSSSTAYMELRSLTSEDSAVYYCLTGFDYWGQGTTLTVSS

Light chain: DNA sequence (SEQ ID NO: 37):
ATGGATTTTCAGGTGCAGATTTTCAGCTTCCTGCTAATCAGTGTCTCAGTCATAATGTCCAGAGGACAAATTGTTCTC ACCCAGTCTCCAGCAATCATGTCTGCATCTCCTGGGGAGAAGGTCACCTTGACCTGCAGTGCCAGCTCAAGTGTGAAT

TCCAGCTACTTGTACTGGTACCAGCAGAAGCCAGGATCCTCCCCCAAACTCTGGATTTATAGCACATCCAACCTGGCT

TCTGGAGTCCCTGCTCGCTTCAGTGGCAGTGGGTCTGGGACCTCTTACTCTCTCACAATCAGCAGCATGGAGGCTGAA

GATGCTGCCTCTTATTTCTGCATCAGTGGAGTAGTTACCCGTACACGTTCGGAGGGGGGACCAAGCTGGAAATAAAA

Light chain: Amino acid sequence (SEQ ID NO: 38):
MDFQVQIFSFLLISVSVIMSRGQIVLTQSPAIMSASPGEKVTLTCSASSSVNSSYLYWYQQKPGSSPKLWIYSTSNLA

SGVPARFSGSGSGTSYSLTISSMEAEDAASYFCHQWSSYPYTFGGGTKLEIK mAb 11B6
Heavy chain: DNA sequence (SEQ ID NO: 39):
ATGATGGTGTTAAGTCTTCTGTACCTGTTGACAGCCCTTCCGGGTATCCTGTCAGAGGTGCAGCTTCAGGAGTCAGGA CCTGGCCTGGCAAAACCTTCTCAGACTCTGTCCCTCACCTGTTCTGTCACTGGCTACTCCATCACCAGTGATTACTGG

AACTGGATCCGGAAATTCCCAGGGAATAAACTTGAATACATGGGGTACATAAACTACAGTGGTAACACTTACTACAAT

CCATCTCTCAAAAGTCGAATCTCCATAACTCGAGACACATCCAAGAACCAGTATTACCTGCAATTGAATTCTGTGACT

ACTGAGGACACAGCCACGTATTACTGTGCAAGATATGGGGATTACGACAGGGTTCCTGGCACTTCGATGTCTGGGGC

CCAGGGACCACGGTCACCGTCTCCTCA

Heavy chain: Amino acid sequence (SEQ ID NO: 40):
MMVLSLLYLLTALPGILSEVQLQESGPGLAKPSQTLSLTCSVTGYSITSDYWNWIRKFPGNKLEYMGYINYSGNTYYN

PSLKSRISITRDTSKNQYYLQLNSVTTEDTATYYCARYGGLRQGSWHFDVWGPGTTVTSS

Light chain: DNA sequence (SEQ ID NO: 41):
ATGGATTTTCAGGTGCAGATTTTCAGCTTCCTGCTAATCAGTGCCTCAGTCATAATGTCCAGAGGACAAATTGTTCTC ACCCAGTCTCCAGCAATCATGTCTGCATCTCCAGGGGAGAAGGTCACCATATCCTGCAGTGCCAGCTCAAGTGTAAGT

TACATGTACTGGTACCAGCAGAAGCCAGGATCCTCCCCCAAACCCTGGATTTATCGCACATCCAACCTGGCTTCTGGA

GTCCCTGCGCGCTTCAGTGGCAGTGGGTCTGGGACCTCTTACTCTCTCACAATCAGCAGCATGGAGGCTGAAGATGCT

GCCACTTATTACTGCCAGCAGTATCATAGTTACCCAGCGACGTTCGGTGGAGGCACCAAGCTGGAAATCAAA

Light chain: Amino acid sequence (SEQ ID NO: 42):
MDFQVQIFSFLLISASVIMSRGQIVLTQSPAIMSASPGEKVTISCSASSSVSYMYWYQQKPGSSPKPWIYRTSNLASG

VPARFSGSGSGTSYSLTISSMEAEDAATYYCQQYHSYPATFGGGTKLEIK mAb 11D3
Heavy chain: DNA sequence (SEQ ID NO: 43):
ATGGGTTGGCTGTGGAACTTGCTATTCCTGATGGCAGCTGCCCAAAGTGCCCAAGCACAGATCCAGTTGGTACAGTCT GGACCTGAGCTGAAGAAGCCTGGAGAGACAGTCAAGATCCTCCTGCAAGGCTTCTGGGTATATCTTCACAACCTATGGA

```
ATGTACTGGGTGAAACAGGCTCCAGGAAAGGGTTTAAAGTGGATGGGCTGGATAAACACCTACTCTGGAGTGCCAACA

TATGTTGATGACTTCAAGGGACGGTTTGCCTTCTCTTTGGAAACATCTGCCAGCACTGCCTATTTGCAGATCAACAAC

CTCAAAAATGAGGACACGGCTACATATTTCTGTGTAGTTGCCGGGTGGTTTGCTTACTGGGGCCAAGGGACTCTGGTC

ACTGTCTCTGCA

Heavy chain: Amino acid sequence (SEQ ID NO: 44):
MGWLWNLLFLMAAAQSAQAQIQLVQSGPELKKPGETVKISCKASGYIFTTYGMYWVKQAPGKGLKWMGWINTYSGVPT

YVDDFKGRFAFSLETSASTAYLQINNLKNEDTATYFCVVAGWFAYWGQGTLVTVSA

Light chain: DNA sequence (SEQ ID NO: 45):
ATGGACATGAGGACCCCTGCTCAGTTTCTTGGAATCTTGTTGCTCTGGTTTCCAGGTATCAAATGTGACATCAAGATG

ACCCAGTCTCCATCTTCCATGTATGCATCTCTAGGAGAGAGAGTCACTATCACTTGCAAGGCGAGTCAGGACATTAAG

AGCTATTTAAGCTGGTTCCAGCAGAAACCAGGGAAATCTCCTAAGACCCTGATCTATCGTGCAAATATATTGATAGAT

GGGGTCCCATCAAGGTTCAGTGGCAGTGGATCTGGGCAAGATTATTCTCTCACCATCAGCAGCCTGGAGTATGAAGAT

ATGGGAATTTATTATTGTCTACAATATGATGAGTTTCCGTACACGTTCGGAGGGGGGACCAAGCTGGAAATAAAA

Light chain: Amino acid sequence (SEQ ID NO: 46):
MDMRTPAQFLGILLLWFPGIKCDIKMTQSPSSMYASLGERVTITCKASQDIKSYLSWFQQKPGKSPKTLIYRANILID

GVPSRFSGSGSGQDYSLTISSLEYEDMGIYYCLQYDEFPYTFGGGTKLEIK mAb 11H2
Heavy chain: DNA sequence (SEQ ID NO: 105)
ATGAACTTGGGGCTCAGCTTGATTTTCCTTGTCCTTGTTTTAAAAGGTGTCCAGTGTGACGTGAAGCTGGTGGAGTCT

GGGGGAGGCTTAGTGCAGCCTGGAGGGTCCCTGAAACTCTCCTGTGCAGCCTCTGG

ATTCACTTTCAGTGACTATTACATGTATTGGGTTCGCCAGACTCCAGAGAAGAGACTGGAGTGGGTCGCATATGTTAG

TAGTGGTGGTGGTAGTATCTATTATCCAGACACTGTAAAGGGCCGATTCACCATCT

CCAGAGACAATGCCAAGAACACCCTGTATTTGCAAATGAGCCGTCTGAAGTCTGAGGACACAGCCATGTATTACTGTG

CAAGGCATGGGTCCCCCTTCGGTAGTAGCCGAGGGGCCTGGTTTGCTTACTGGGGC

CAGGGGACTCTGGTCACTGTCTCTGCA

Heavy chain: Amino acid sequence (SEQ ID NO: 106)
MNLGLSLIFLVLVLKGVQCDVKLVESGGGLVQPGGSLKLSCAASGFTFSDYYMYWVRQTPEKRLEWVAYVSSGGGSIY

YPDTVKGRFTISRDNAKNTLYLQMSRLKSEDTAMYYCARHGSPFGSSRGAWFAYWG

QGTLVTVSA

Light chain: DNA sequence (SEQ ID NO: 107)
ATGAGTGTGCCCACTCAGGTCCTGGGGTTGCTGCTGCTGTGGCTTACAGGTGCCAGATGTGACATCCAGATGACTCAG

TCTCCAGCCTCCCTGTCTGCATCTGTGGGAGAAACTGTCACCATCACATGTCGAGC

AAGTGAGAATATTTACAGTTATTTAGCATGGTATCAGCAGAAACAGGGAAAATCTCCTCAGCTCCTGGTCTATAATGC

AAAAACCTTAGCAGAGGGTGTGCCATCAAGGTTCAGTGGCAGTGGATCAGGCACAC

AGTTTTCTCTGAAGATCAACAGCCTGCAGCCTGAAGATTTTGGGAATTATTACTGTCAACATTATGATGGTTTTCCGT

TCACGTTCGGTGGTGGGACCAAGCTGGAGCTGAAA

Light chain: Amino acid sequence (SEQ ID NO: 108)
MSVPTQVLGLLLLWLTGARCDIQMTQSPASLSASVGETVTITCRASENIYSYLAWYQQKQGKSPQLLVYNAKTLAEGV

PSRFSGSGSGTQFSLKINSLQPEDFGNYYCQHYDGFPFTFGGGTKLELK mAb 6C12
Heavy chain: DNA sequence (SEQ ID NO: 109)
ATGGGTTGGCTGTGGAACTTGCTATTCCTGATGGCAGCTGCCCAAAGTGCCCAAGCACAGATCCAGTTGATACAGTCT

GGACCTGAGCTGAAGAAGCCTGGAGAGACAGTCAAGATCTCCTGCAAGGCTTCTGGGTATACCTTCACAACCTTTGGA

ATGAGCTGGGTGAAACAGGCTCCAGGAAAGGGTTTAAAGTGGATGGGCTGGATAAGCACCTACTCTGGAGTGCCAACA

TATGCTGATGACTTCAAGGGACGGTTTGCCTTCTCTTTGGAAACCTCTGCCAGCACTGCCTATTTGCAGATCAACAAC
```

-continued

CTCAAAAATGAGGACACGGCTTCATATTTCTGTGCAAGACACACCTTCCAAAGTCGCGGGTTGGCTTACTGGGCCAA

GGGACTCTGGTCACTGTCTCTGCA

Heavy chain: Amino acid sequence (SEQ ID NO: 110)
<u>MGWLWNLLFLMAAAQSAQA</u>QIQLIQSGPELKKPGETVKISCKASGYTFTTFGMSWVKQAPGKGLKWMGWISTYSGVPT

YADDFKGRFAFSLETSASTAYLQINNLKNEDTASYFCARHTFQSRGLAYWGQGTLVTVSA

Light chain: DNA sequence (SEQ ID NO: 111)
<u>ATGGGCATCAAAATGGAGTCACAGATTCAGGTCTTTGTATTCGTGTTTCTCTGGTTGTCTGGTGTTGACGGAGACATT</u>

GTGATGACCCAGTCTCACAAATTCATGTCCACATCAGTAGGAGACAGGGTCAGCATCACCTGCAAGGCCAGTCAGGAT

GTGATTACTACTGTAGCCTGGTATCAACAGAAACCAGGACAATCTCCTAAACTACTGATTTACTCGGCATCCTACCGG

TACACTGGAGTCCCTGATCGCTTCACTGGCAGTGGATCTGGGACGGATTTCACTTTCACCATCACCAGTGTGCAGACT

GAAGACCTGGCAGTTTATTACTGTCAGCAACATTATAGTACTCCGTGGACGTTCGGTGGAGGCACCAAGCTGGAAATC

AAA

Light chain: Amino acid sequence (SEQ ID NO: 112)
<u>MGIKMESQIQVFVFVFLWLSGVDGD</u>IVMTQSHKFMSTSVGDRVSITCKASQDVITTVAWYQQKPGQS

PKLLIYSASYRYTGVPDRFTGSGSGTDFTFTITSVQTEDLAVYYCQQHYSTPWTFGGGTKLEIK mAb 4H3
Heavy chain: DNA sequence (SEQ ID NO: 113)
<u>ATGGGATGGAGCTGTATCATGCTCTTCTTGGCAGCAACAGCTACAGGTGTCCACTCC</u>CAGGTCCAACTGCAGCAGCCT GGGGCTGAGCTTGTGAAGCCTGGGGCTTCAGTGAAGCTGTCCTGCAAGGCTTCTGGCTACACCTTCACCAACTACTGG

ATACACTGGATGAAGCAGAGGCCTGGACGAGGCCTTGAGTGGATTGGAAGGATTGATCCTAATAGTGGTGGTACTAAG

TACAATGAGAAGTTCAAGAGCAAGGCCACACTGACTGTCGACAAACCCTCCATCACAGCCTACATGCAGCTCAGCAGC

CTGACATCTGAGGACTCTGCGGTCTATTATTGTGCAGCATTCGGTAGTACCTACGGGTTTGCTTACTGGGGCCAAGGG

ACTCTGGTCACTGTCTCTGCA

Heavy chain: Amino acid sequence (SEQ ID NO: 114)
<u>MGWSCIMLFLAATATGVHS</u>QVQLQQPGAELVKPGASVKLSCKASGYTFTNYWIHWMKQRPGRGLEWIGRIDPNSGGTK

YNEKFKSKATLTVDKPSITAYMQLSSLTSEDSAVYYCAAFGSTYGFAYWGQGTLVTVSA

Light chain: DNA sequence (SEQ ID NO: 115)
<u>ATGGATTCACAGGCCCAGGTTCTTATATTGCTGCTGCTATGGGTATCTGGTACCTGTGGGGACATTGTGATGTCACAG</u>

TCTCCATCCTCCCTGGCTGTGTCAGCAGGAGAGAAGGTCACTATGAGTTGCAAATCCAGTCAGAGTCTGCTCAACAGT

AGAACCCGAAAGAACTACTTGGCTTGGTACCAGCAGAAACCAGGGCAGTCTCCTAAACTGCTGATCTACTGGGCATCC

ACTAGGGAATCTGGGGTCCCTGATCGCTTCACAGGCAGTGGATCTGGGACAGATTTCACTCTCACCATCAGCAGTGTG

CAGGCTGAAGACCTGGCAGTTTATTACTGCAAGCAATCTTATAATCTGTACACGTTCGGAGGGGGGACCAAGCTGGAA

ATAAAA

Light chain: Amino acid sequence (SEQ ID NO: 116)
<u>MDSQAQVLILLLLWVSGTCGD</u>IVMSQSPSSLAVSAGEKVTMSCKSSQSLLNSRTRKNYLAWYQQKPGQSPKLLIYWAS

TRESGVPDRFTGSGSGTDFTLTISSVQAEDLAVYYCKQSYNLYTFGGGTKLEIK mAb 4D8
Heavy chain: DNA sequence (SEQ ID NO: 117)
<u>ATGAACTTGGGGCTCAGCTTGATTTTCCTTGTCCTTGTTTTAAAAGGTGTCCAGTGTGAAGTGACGCTGGTGGAGTCT</u>

GGGGGAGGCTTAGTGCAGCCTGGAGGGTCCCTGAAACTCTCCTGTGCAGCCTCTGGATTCACTTTCAGTGACTATTAC

ATGTATTGGGTTCGCCAGACTCCAGAGAAGAGGCTGGAGTGGGTCGCATACATTAGTCCTGGTGGTGGTAGCACCTAT

TATCCGGACACTATAAAGGGCCGATTCACCATCTCCAGAGACAATGCCAAGAACACCCTGTACCTGCAAATGAGCCGT

CTGAAGTCTGAGGACACAGCCATGTATTACTGTACAAGACATGGGTCCCCCTACGGTAGTAGTCGAGGGGCCTGGTTT

GCTTACTGGGGCCAAGGGACTCTGGTCACTGTCTCTGCA

Heavy chain: Amino acid sequence (SEQ ID NO: 118)
MNLGLSLIFLVLVLKGVQCEVTLVESGGGLVQPGGSLKLSCAASGFTFSDYYMYWVRQTPEKRLEWVAYISPGGGSTY

YPDTIKGRFTISRDNAKNTLYLQMSRLKSEDTAMYYCTRHGSPYGSSRGAWFAYWGQGTLVTVSA

Light chain: DNA sequence (SEQ ID NO: 119)
ATGAGTGTGCCCACTCAGGTCCTGGGGTTGCTGCTGCTGTGGCTTACAGGTGCCAGATGTGACATCCAGATGACTCAG TCTCCAGCCTCCCTATCTGCATCTGTGGGAGAAACTGTCACCATCACATGTCGAGCAAGTGAGAATATTTACAGTTAT

TTAGCATGGTATCAGCAGAAACAGGGAAAATCTCCTCAGCTCCTGGTCTATAATGGAAAAACCTTAGCAGAAGGTGTG

CCAGCAAGGTTCAGTGGCAGTGGATCAGGCACACAGTTTTCTCTGAAGATCAACAGCCTACAGCCTGAAGATTTTGGG

AGTTATTACTGTCAACATCATGATGGTATTCCGGTCACGTTCGGTGCTGGGACCAAGCTGGAGCTGAAA

Light chain: Amino acid sequence (SEQ ID NO: 120)
MSVPTQVLGLLLLWLTGARCDIQMTQSPASLSASVGETVTITCRASENIYSYLAWYQQKQGKSPQLLVYNGKTLAEGV

PARFSGSGSGTQFSLKINSLQPEDFGSYYCQHHDGIPVTFGAGTKLELK mAb 2E2
Heavy chain: DNA sequence (SEQ ID NO: 121)
ATGAACTTGGGGCTCAGCTTGATTTTCCTTGTCCTTGTTTTAAAAGGTGTCCAGTGTGAAGTGAAGC

TGGTGGAGTCGGGGGGAGGCTTAGTGCAGCCTGGAGGGTCCCTGAAACTCTCCTGTGTAGCCTCTGG

ATTCACTTTCAGTGACTATCACATGCATTGGGTTCGCCAGACTCCAGAGAAGAGGCTGGAGTGGGTC

GCATACATTAGTAAAGGTGGTGGTAGCACCTATTATCCAGACACTGAAAAGGGCCGATTCACCATCT

CCAGAGACAATGCCAAGAATACCCTGTACCTGCAAATGAGCCGTCTGAAGTCTGAGGACACAGCCAT

GTATTACTGTGCAAGATCCCCCGGCCCTAGTAGCTTCTACTGGTACTTCGATGTCTGGGCACAGGG

ACCACGGTCACCGTCTCCTCA

Heavy chain: Amino acid sequence (SEQ ID NO: 122)
MNLGLSLIFLVLVLKGVQCEVKLVESGGGLVQPGGSLKLSCVASGFTFSDYHMHWVRQTPEKRLEWV

AYISKGGGSTYYPDTEKGRFTISRDNAKNTLYLQMSRLKSEDTAMYYCARSPGPSSFYWYFDVWGTG

TTVTVSS

Light chain: DNA sequence (SEQ ID NO: 123)
ATGAGTGTGCCCACTCAGGTCCTGGGGTTGCTGCTGCTGTGGCTTACAGGTGCCAGATGTGACATCC

AGATGACTCAGTCTCCAGCCTCCCTATCTGCATCTGTGGGAGAAACTGTCACCATCACATGTCGAGC

AAGTGAGAATATTTACAGTTATTTAGCATGGTATCAGCAGAAACAGGGAAAATCTCCTCAGCTCCTG

GTCTATAATGCAAAAACCTTAGCAGAAGGTGTGCCATCAAGGTTCAGTGGCAGTGGATCAGGCACAC

AGTTTTCTCTGAAGATCAACAGCCTGCAGCCTGAAGATTTTGGGAGTTATTACTGTCAACATCATTA

TGGTATTCCGGTCACGGTCGGTGTAGGGACCAAGCTGGAGCTGAAA

Light chain: Amino acid sequence (SEQ ID NO: 124)
MSVPTQVLGLLLLWLTGARCDIQMTQSPASLSASVGETVTITCRASENIYSYLAWYQQKQGKSPQLL

VYNAKTLAEGVPSRFSGSGSGTQFSLKINSLQPEDFGSYYCQHHYGIPVTVGVGTKLELK

Example 4

Construction of CHO Cell Line Expressing Canine IL-4 Receptor Alpha Chain and Use in Ligand Blockade Assays The gene encoding full length canine IL-4 receptor alpha chain (cIL-4R$_\alpha$; SEQ ID NO: 4) was synthesized and sub-cloned into a mammalian expression vectors. The resulting plasmid was transfected into CHO DG44 cells. At 48 hours post-transfection, the cells were diluted into 96-well plates to generate single cell clones. About 130 clones were obtained after a 4-week incubation. All of the clones were screened for expression of cIL-4R$_\alpha$ by FACS using the anti-cIL-4R$_\alpha$ monoclonal antibody 6B2. Three clones were selected for stability evaluation. Stability was monitored for 20 passages by FACS.

In order to assess the ability of monoclonal antibodies specific to canine IL-4 receptor alpha to block the binding of canine IL-4 to canine IL-4 R alpha expressed on the surface of CHO cells, a ligand blockade assay was set as follows:

Reagent and Equipments:
Cell growth medium: CD OptiCHO medium+8 mM L-Glutamine+0.018% F-68
FACS Buffer: BD Pharmingen Stain Buffer (BD cat #: 554657)
R-phycoerythrin conjugated Streptavidin (Life Technologies: SB66)
Canine IL-4 (R&D system, cat #754-CL/CF)
Lightning-Link Biotin Conjugation Kit Type A (Novus: 704-0010) used to biotinylate canine IL-4 as per manufacturer's recommendation Flow cytometer: BD Accuri-C6

Procedure:
1. CHO-DH44-canIL-4Rα cell grown to 2-4×10⁶ cells/mL with more than 96% viability.
2. The cells were spun down, the supernatant discarded, and the cells were suspended in FACS buffer to 2×10⁷ cells/mL.
3. The cells were distributed into a U-shape 96-well plate, 50 μl each well.
4. The anti-canine IL-4Rα mAbs in FACS buffer was diluted three-fold on a 96-well plate from top down to bottom well, starting at 50 μg/mL.
5. 50 μl of each diluted Ab was transferred into the cell plate and then incubated on ice for 30 min.
6. The cells were washed twice with FACS buffer.
7. The cells were resuspended into 100 μl of biotinylated canine IL-4 at 0.32 μg/mL in FACS buffer and incubated on ice for 30 min.
8. The cells were washed twice with FACS buffer.
9. The cells were responded into 100 μl of R-phycoerythrin conjugated Streptavidin (1:1000 dilution) in FACS buffer and incubated on ice for 30 min.
10. The cells were washed twice with FACS buffer.
11. The cells were brought up to 300 μl in FACS buffer.
12. 10,000 cells were read for each sample by BD Accuri-C6.
13. The resulting readout were analyzed by FlowJo to get the mean fluorescent intensity (MFI).

Figure 2B:
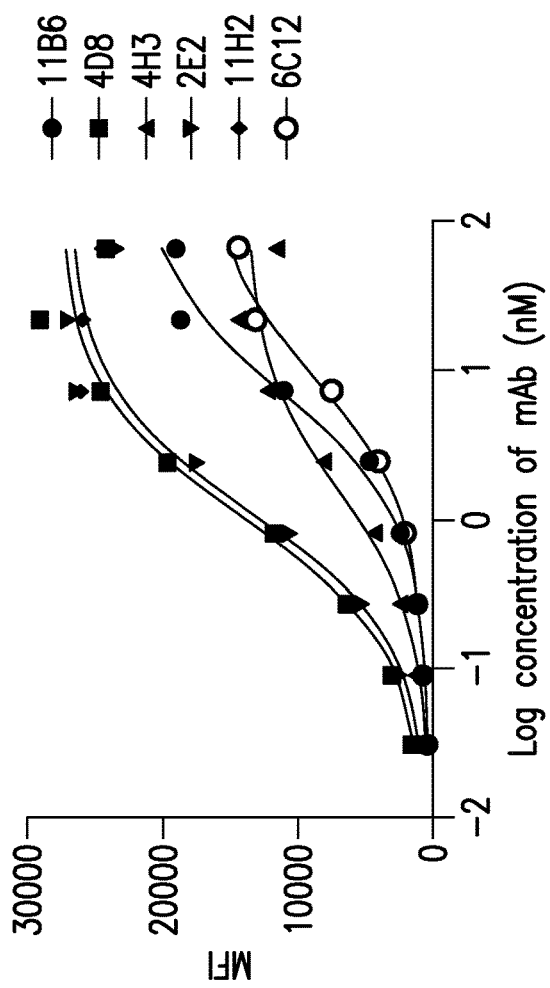
FIG. 2B depicts the dose response curves for CHO-cIL-4R$_\alpha$ by the mouse anti-canine IL-4R$_\alpha$ monoclonal antibodies (mAbs): 11B6(●), 4D8(■), 4H3(▲), 2E2(▼), 11H2(♦), and 6C12(○). The abscissa depicts the log concentration of the mAb (nM) being added, the ordinate depicts the mean fluorescence intensity (MFI) employing FACS. The half maximal effective concentrations (EC50) for each of the antibodies is provided in Table 2 below.
Figure 2A:
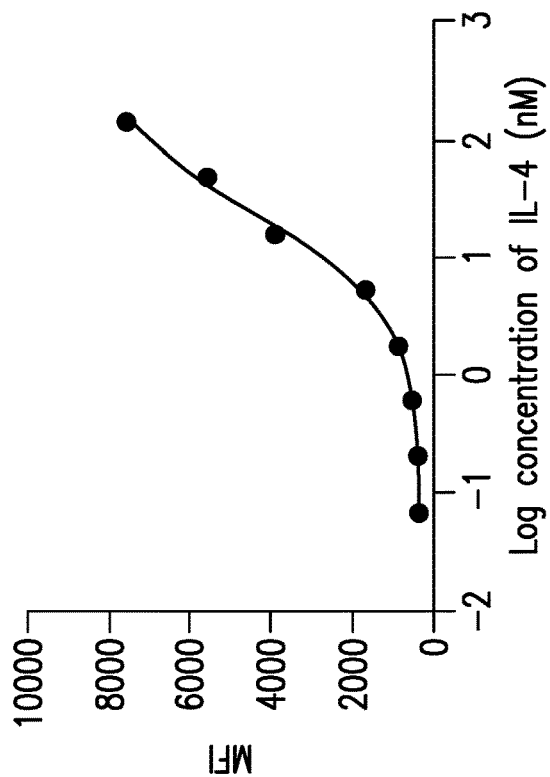
FIG. 2A shows the dose response curve for the binding of canine IL-4 to canine IL-4R$_\alpha$ expressed on the surface of CHO cells, using a cell-based CHO-cIL-4R$_\alpha$ binding assay. The abscissa depicts the log concentration of IL-4 being added, the ordinate depicts the mean fluorescence intensity (MFI) employing FACS.

A dose response curve for the binding of canine IL-4 to canine IL-4R$_\alpha$ expressed on the surface of CHO cells was obtained using the cell-based CHO-cIL-4R$_\alpha$ binding assay (see, FIG. 2A). A half maximal effective concentration (EC50) of 25 nM was determined from this curve. Next, dose response curves for the binding of CHO-cIL-4R$_\alpha$ by the mouse anti-canine IL-4R$_\alpha$ monoclonal antibodies (mAbs): 11B6, 4D8, 4H3, 2E2, 11H2, and 6C12 were obtained (see, FIG. 2B). The half maximal effective concentrations (EC50) for each of the antibodies is provided in Table 2 below.

TABLE 2

| mABs | Binding/Blocking of Various mABs | |
|---|---|---|
| | EC50 (nM) | IC50 (nM) |
| 11B6 | 7.5 | 53.2 |
| 4D8 | 1.1 | 4.2 |
| 4H3 | 1.6 | 3.9 |
| 2E2 | 1.2 | 2.1 |
| 11H2 | 1.2 | 1.7/1.0* |
| 6C12 | 8.6 | 19.3 |

*Determinations from two separate studies

Figure 3A:
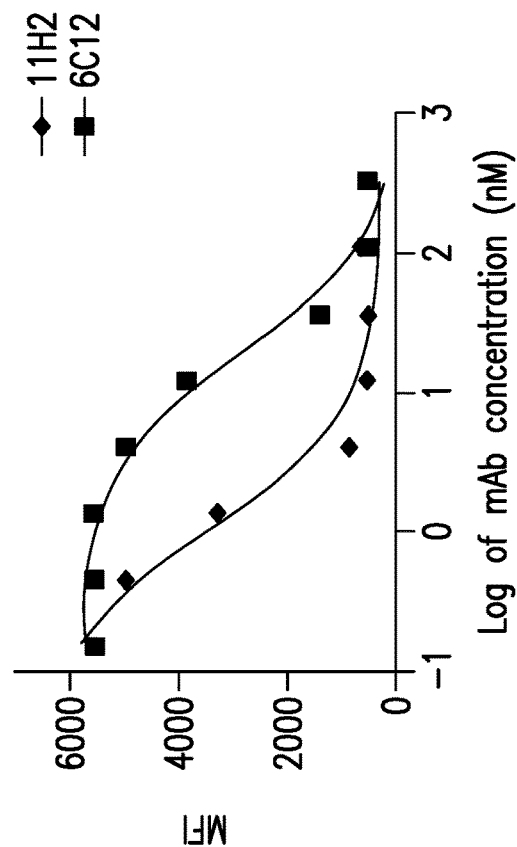
FIGS. 3A and 3B show the results of the addition of successively diluted individual mouse anti-canine IL-4R$_\alpha$ monoclonal antibodies (mAbs) on the binding of IL-4 with the cell-based CHO-cIL-4R$_\alpha$.
Figure 3B:
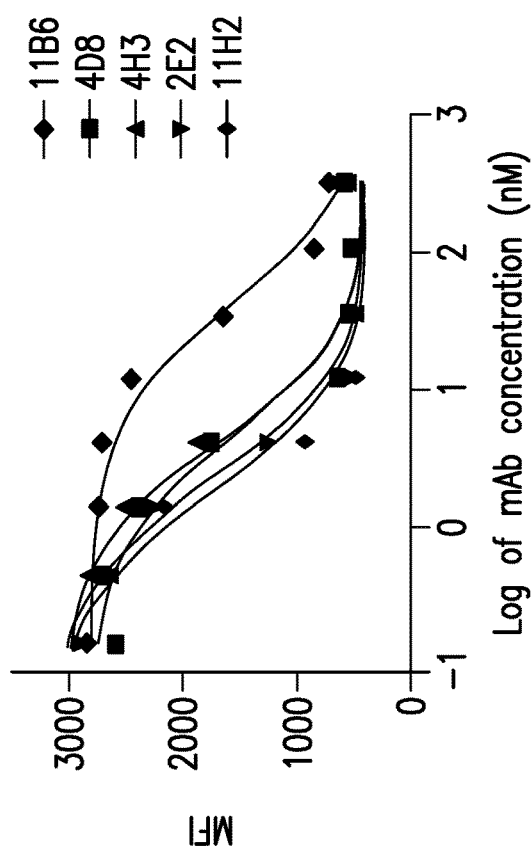

The mouse anti-canine IL-4R$_\alpha$ monoclonal antibodies (mAbs) were then assayed for their ability to block the binding of canine IL-4 to the cell-based CHO-cIL-4R$_\alpha$. As depicted in FIG. 3A the five mAbs, 11B6, 4D8, 4H3, 2E2, and 11H2 displayed significant blocking ability. In a complementary study a sixth mAbs was tested (6C12), and compared with one of the five mAbs tested (11H2) in FIG. 3A. As is apparent from FIG. 3B and Table 2, 6C12 mAbs has a significantly higher half maximal inhibitory concentration (IC50) than the 11H2 mAbs. Four of anti-cIL-4Rα monoclonal antibodies, 4D8, 2E2, 4D8, and 11H2 showed superior blocking ability, as can be seen in FIGS. 3A and 3B, as well as in Table 2.

Example 5

Amino Acid Sequences of the Mouse CDRS

CDRs from mouse anti-canine IL-4 receptor α chain monoclonal antibodies:

| | | SEQ ID NO: |
|---|---|---|
| VL CDR-1 | | |
| 1A3 | Arg Ala Ser Ser Ser Val Ser Phe Met Phe | 47 |
| 1A9 | Lys Ala Ser Gln Asn Val Arg Ser Ala Val Ala | 48 |
| 1B12 | Arg Ser Ser Lys Ser Leu Leu His Ser Asn Gly Asn Thr Tyr Leu Phe | 49 |
| 10C12 | Lys Ser Ser Gln Ser Leu Leu Asn Ser Ser Asn Gln Lys Asn Tyr Leu Ala | 50 |
| 10F2 | Lys Ser Ser Gln Asn Leu Leu Tyr Gly Gly Asn Gln Lys Asn Tyr Leu Ala | 51 |
| 10E10 | Lys Ala Ser Asp His Ile Asn Asn Trp Leu Ala | 52 |
| 10G8 | Ser Ala Ser Ser Ser Val Asn Ser Ser Tyr Leu Tyr | 53 |
| 11B6 | Ser Ala Ser Ser Ser Val Ser Tyr Met Tyr | 54 |
| 11D3 | Lys Ala Ser Gln Asp Ile Lys Ser Tyr Leu Ser | 55 |
| 11H2 | Arg Ala Ser Glu Asn Ile Tyr Ser Tyr Leu Ala | 129 |
| 6C12 | Lys Ala Ser Gln Asp Val Ile Thr Thr Val Ala | 130 |
| 4D8 | Arg Ala Ser Glu Asn Ile Tyr Ser Tyr Leu Ala | 129 |
| 4H3 | Lys Ser Ser Gln Ser Leu Leu Asn Ser Arg Thr Arg Lys Asn Tyr Leu Ala | 131 |
| 2E2 | Arg Ala Ser Glu Asn Ile Tyr Ser Tyr Leu Ala | 129 |

-continued

| | | SEQ ID NO: |
|---|---|---|
| VL CDR-2 | | |
| 1A3 | Asp Thr Ser Asn Leu Ala Ser | 56 |
| 1A9 | Leu Ala Ser Asn Arg His Thr | 57 |
| 1B12 | Arg Met Ser Asn Leu Ala Ser | 58 |
| 10C12 | Phe Ala Ser Thr Arg Glu Ser | 59 |
| 10F2 | Trp Ala Ser Thr Arg Glu Ser | 60 |
| 10E10 | Gly Ala Thr Ser Leu Glu Thr | 61 |
| 10G8 | Ser Thr Ser Asn Leu Ala Ser | 62 |
| 11B6 | Arg Thr Ser Asn Leu Ala Ser | 63 |
| 11D3 | Arg Ala Asn Ile Leu Ile Asp | 64 |
| 11H2 | Asn Ala Lys Thr Leu Ala Glu | 132 |
| 6C12 | Ser Ala Ser Tyr Arg Tyr Thr | 133 |
| 4D8 | Asn Gly Lys Thr Leu Ala Glu | 134 |
| 4H3 | Trp Ala Ser Thr Arg Glu Ser | 60 |
| 2E2 | Asn Ala Lys Thr Leu Ala Glu | 132 |
| VL CDR-3 | | |
| 1A3 | Gln Gln Trp Ser Ser Asn Pro Leu Thr | 65 |
| 1A9 | Leu Gln His Trp Asn Tyr Pro Phe Thr | 66 |
| 1B12 | Met Gln His Leu Glu Tyr Pro Phe Thr | 67 |
| 10C12 | Gln Gln His Tyr Ser Thr Pro Tyr Thr | 68 |
| 10F2 | Gln Gln Tyr Tyr Asp Tyr Pro Tyr Thr | 69 |
| 10E10 | His Gln Tyr Trp Ser Ile Pro Tyr Thr | 70 |
| 10G8 | His Gln Trp Ser Ser Tyr Pro Tyr Thr | 71 |
| 11B6 | Gln Gln Tyr His Ser Tyr Pro Ala Thr | 72 |
| 11D3 | Leu Gln Tyr Asp Glu Phe Pro Tyr Thr | 73 |
| 11H2 | Gln His Tyr Asp Gly Phe Pro Phe Thr | 135 |
| 6C12 | Gln Gln His Tyr Ser Thr Pro Trp Thr | 136 |
| 4D8 | Gln His His Asp Gly Ile Pro Val Thr | 137 |
| 4H3 | Lys Gln Ser Tyr Asn Leu Tyr Thr | 138 |
| 2E2 | Gln His His Tyr Gly Ile Pro Val Thr | 139 |
| VH CDR-1 | | |
| 1A3 | Asp Phe Gly Met His | 74 |
| 1A9 | Ser Ser Trp Met Asn | 75 |
| 1B12 | Asp Tyr Tyr Met Asn | 76 |
| 10C12 | Asp Tyr Glu Met His | 77 |
| 10F2 | Ser Tyr Gly Val Ser | 78 |
| 10E10 | Thr Tyr Asp Ile His | 79 |
| 10G8 | Asp Tyr Glu Met His | 80 |

|  |  | SEQ ID NO: |
|---|---|---|
| 11B6 | Ser Asp Tyr Trp Asn | 81 |
| 11D3 | Thr Tyr Gly Met Tyr | 82 |
| 11H2 | Asp Tyr Tyr Met Tyr | 140 |
| 6C12 | Thr Phe Gly Met Ser | 141 |
| 4D8 | Asp Tyr Tyr Met Tyr | 140 |
| 4H3 | Asn Tyr Trp Ile His | 142 |
| 2E2 | Asp Tyr His Met His | 143 |
| VH CDR-2 | | |
| 1A3 | Tyr Ile Ser Ser Gly Ser Gly Thr Ile Tyr Tyr Ala Asp Thr Val Arg Gly | 83 |
| 1A9 | Arg Ile Tyr Pro Gly Asp Gly Asp Thr Lys Tyr Asn Gly Lys Phe Lys Gly | 84 |
| 1B12 | Asp Ile Ile Pro Ser Asn Gly Gly Thr Ser Tyr Asn Gln Lys Phe Lys Gly | 85 |
| 10C12 | Ala Ile Asp Pro Glu Thr Cys Gly Thr Ala Tyr Asn Gln Lys Phe Lys Gly | 86 |
| 10F2 | Val Ile Trp Gly Asp Gly Ser Thr Tyr Phe His Ser Ala Leu Ile Ser | 87 |
| 10E10 | Trp Ile Tyr Pro Arg Asp Gly Arg Thr Thr Tyr Asn Glu Lys Phe Lys Ala | 88 |
| 10G8 | Ala Ile Asp Pro Glu Thr Gly Gly Thr Ala Tyr Asn Gln Lys Phe Lys Gly | 89 |
| 11B6 | Tyr Ile Asn Tyr Ser Gly Asn Thr Tyr Tyr Asn Pro Ser Leu Lys Ser | 90 |
| 11D3 | Trp Ile Asn Thr Tyr Ser Gly Val Pro Thr Tyr Val Asp Asp Phe Lys Gly | 91 |
| 11H2 | Tyr Val Ser Ser Gly Gly Gly Ser Ile Tyr Tyr Pro Asp Thr Val Lys Gly | 144 |
| 6C12 | Trp Ile Ser Thr Tyr Ser Gly Val Pro Thr Tyr Ala Asp Asp Phe Lys Gly | 145 |
| 4D8 | Tyr Ile Ser Pro Gly Gly Gly Ser Thr Tyr Tyr Pro Asp Thr Ile Lys Gly | 146 |
| 4H3 | Arg Ile Asp Pro Asn Ser Gly Gly Thr Lys Tyr Asn Glu Lys Phe Lys Ser | 147 |
| 2E2 | Tyr Ile Ser Lys Gly Gly Gly Ser Thr Tyr Tyr Pro Asp Thr Glu Lys Gly | 148 |
| VH CDR-3 | | |
| 1A3 | Gly Asp Leu Tyr Tyr Gly Ser Ser Phe Asp Ala Tyr | 92 |
| 1A9 | Asp Asp Tyr Asp Trp Ala Ser | 93 |
| 1B12 | Gly Ile Ser Tyr Tyr Gly Asn Arg Tyr Tyr Phe Thr Met Asp Tyr | 94 |
| 10C12 | Ser Lys Leu Gly Arg Gly Trp Tyr Phe Asp Val | 95 |
| 10F2 | Gln Gly Thr Ile Tyr Asp Gly Tyr Tyr Asn Tyr Ala Met Asp Tyr | 96 |
| 10E10 | Ser Ser Pro Phe Gly Tyr | 97 |
| 10G8 | Gly Phe Asp Tyr | 98 |
| 11B6 | Tyr Gly Gly Leu Arg Gln Gly Ser Trp His Phe Asp Val | 99 |
| 11D3 | Ala Gly Trp Phe Ala Tyr | 100 |
| 11H2 | His Gly Ser Pro Phe Gly Ser Ser Arg Gly Ala Trp Phe Ala Tyr | 149 |
| 6C12 | His Thr Phe Gln Ser Arg Gly Leu Ala Tyr | 150 |
| 4D8 | His Gly Ser Pro Tyr Gly Ser Ser Arg Gly Ala Trp Phe Ala Tyr | 151 |
| 4H3 | Phe Gly Ser Thr Tyr Gly Phe Ala Tyr | 152 |
| 2E2 | Ser Pro Gly Pro Ser Ser Phe Tyr Trp Tyr Phe Asp Val | 153 |

TABLE 3

CANONICAL STRUCTURES

|  | L1 | L2 | L3 | H1 | H2 | H3 |
|---|---|---|---|---|---|---|
| 1A3 | L1-1 | L2-1 | L3-1 | H1-1 | H2-3A | H3-12 |
| 1A9 | L1-2A | L2-1 | L3-1 | H1-1 | H2-2A | H3-7 |
| 1B12 | L1-4 | L2-1 | L3-1 | H1-1 | H2-2B | H3-15 |
| 10C12 | L1-3 | L2-1 | L3-1 | H1-1 | * | H3-11 |
| 10F2 | L1-3 | L2-1 | L3-1 | H1-1 | H2-1 | H3-15 |
| 10E10 | L1-2A | L2-1 | L3-1 | H1-1 | H2-2B | H3-6 |
| 10G8 | L1-6 | L2-1 | L3-1 | H1-1 | H2-2B | H3-4 |
| 11B6 | L1-1 | L2-1 | L3-1 | H1-1 | H2-1 | H3-13 |
| 11D3 | L1-2A | L2-1 | L3-1 | H1-1 | H2-2A** | H3-6 |
| 11H2 | L1-6 | L2-1 | L3-1 | H1-1 | H2-3A | H3-15 |
| 6C12 | L1-6 | L2-1 | L3-1 | H1-1 | H2-2A | H3-10 |
| 4D8 | L1-6 | L2-1 | L3-1 | H1-1 | H2-3A | H3-15 |
| 4H3 | L1-3 | L2-1 | L3-3 | H1-1 | H2-3A | H3-9 |
| 2E2 | L1-6 | L2-1 | L3-1 | H1-1 | H2-3A | H3-13 |

* Cysteine in the CDR
** The best assignment that could be made in view of the particular pattern.

Example 6

Epitope Mapping of Murine Anti-Canine IL-4 Receptor Alpha Antibodies

The interaction of antibodies with their cognate protein antigens is mediated through the binding of specific amino acids of the antibodies (paratopes) with specific amino acids (epitopes) of target antigens. An epitope is an antigenic determinant that causes a specific reaction by an immunoglobulin. An epitope consists of a group of amino acids on the surface of the antigen. A protein of interest may contain several epitopes that are recognized by different antibodies. The epitopes recognized by antibodies are classified as linear or conformational epitopes. Linear epitopes are formed by a stretch of a continuous sequence of amino acids in a protein, while conformational epitopes are composed of amino acids that are discontinuous (e.g., far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information on IL-4 receptor alpha can also elucidate unique epitopes, and define the protective or pathogenic effects of vaccines. Epitope identification also can lead to development of subunit vaccines based on chemical or genetic coupling of the identified peptide epitope to a carrier protein or other immunostimulating agents.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively, easier to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of a discontinuous epitope is more technically challenging and requires more specialized techniques such as x-ray co-crystallography of a monoclonal antibody together with its target protein, Hydrogen-Deuterium (H/D) exchange, Mass Spectrometry coupled with enzymatic digestion as well as several other methods known to those skilled in the art.

Mapping of Canine IL-4 Receptor Alpha Epitopes Using Mass Spectroscopy:

A method based on chemical crosslinking and mass spectrometry detection was employed to identify epitopes recognized by anti-canine IL-4 receptor alpha mAbs [CovalX Instrument Incorporated]. The application of this technology to epitope mapping of canine IL-4 receptor alpha chain resulted in identification of epitopes recognized by the mAbs listed in Table 4.

The results from the epitope mapping of canine IL-4 receptor alpha with the six antibodies included in Table 4, indicates that the mAbs recognize specific peptide epitopes that are present within the extracellular domain of canine IL-4 receptor alpha. Notably, two to three epitopes were identified for each of the six monoclonal antibodies (mAbs) tested. Interestingly, one of the epitopes identified for mAbs 2E2 was found to have the exact same amino acid sequence as that for mAbs 11B6 (i.e., SEQ ID NO: 158). As depicted in Table 4 below, mAbs: 4D8, 11H2, and 11B6 all recognize an epitope, labeled with a "1" that is a portion of the same linear amino acid sequence; mAbs: 11E2, 4H3, and 2E2 all recognize an epitope labeled with a "2" that is a portion of another linear amino acid sequence; and mAbs 4H3 and 2H2 recognize an epitope labeled with a "3" that is a portion of a third linear amino acid sequence. This relative consistency in the identification of the relevant epitopes indicates that these six monoclonal antibodies recognize a limited number of portions of canine IL-4 receptor alpha, within its extracellular domain.

TABLE 4

IL-4 RECEPTOR ALPHA EPITOPES RECOGNIZED BY ANTI-CANINE IL-4 RECEPTOR ALPHA MONOCLONAL ANTIBODIES

| ANTIBODY | SEQ ID NO: | EPITOPE SEQUENCE |
|---|---|---|
| 4D8 | 125 | SAELRLSYQLD |
|  | 126 | FQPSKHVKPRT[1] |
| 11H2 | 127 | AGQQLLWSGSFQPSKHVKPRT[1] |
|  | 128 | TLKSGASYS[2] |
| 4H3 | 154 | EDSVCVCSMPI[3] |
|  | 155 | MWTNPYPTENHL |
|  | 156 | ASTLKSG[2] |
| 11B6 | 157 | WSGSFQPSKHVKPR[1] |
|  | 158 | VYNVTYMGPTLR |
| 2E2 | 159 | VLHEPSCFSDYISTSVCQ |
|  | 160 | ENREDSVCVCSMPI[3] |
|  | 161 | KSGASYSARVRAW[2] |
| 6C12 | 158 | VYNVTYMGPTLR |
|  | 162 | YYEPWEQHLP |

[1,2,3] identify three individual groups of epitopes arising from three portions of the antigen.

Together with the CDRs provided in Example 5 for the six antibodies listed in Table 4 above, a one to one relationship is defined between each set of CDRs and their corresponding epitopes in Table 4. This relationship allows a defined linkage between the set of 6 CDRs in Example 5 for each of the six antibodies in Table 4 and the corresponding epitopes that they bind. Accordingly, antibodies (e.g., caninized antibodies) with the defined set of 6 CDRs provided in Example 5 that bind corresponding epitopes in Table 4 are also part of the present invention.

Example 7

Construction of Caninized Anti-Canine IL-4 Receptor Alpha Monoclonal Antibodies

In order to execute the process of caninization, the DNA sequence that encodes the heavy and light chains of canine IgG were determined. The DNA and protein sequence of the canine heavy and light chains are known in the art and can be obtained by searching of the NCBI gene and protein databases. As indicated above, for canine antibodies there are four known IgG subtypes: IgG-A, IgG-B, IgG-C, and IgG-D, and two types of light chains, i.e., kappa and lambda. Without being bound by any specific approach, the overall process of producing caninized heavy and light chains that can be mixed in different combinations to produce caninized anti-canine IL-4 receptor alpha mAbs involves the following scheme:
  i) Identify the DNA sequence of VH and VL domains comprising the CDRs of desired anti-IL-4 receptor alpha mAbs
  ii) Identify the H and L chain CDRs of desired anti-IL-4 receptor mAbs
  iii) Identify a suitable sequence for H and L chain of canine IgG
  iv) Identify the DNA sequence encoding the endogenous CDRs of canine IgG H and L chains of the above sequence.
  v) Replace the DNA sequence encoding endogenous canine H and L chain CDRs with DNA sequences encoding the desired anti-IL-4 receptor alpha CDRs. In addition, optionally replace some canine framework residues with selected residues from the desired anti-IL-4 receptor mAb framework regions.
  vi) Synthesize the DNA from step (v), clone it into a suitable expression plasmid, and transfect the plasmids containing desired caninized H and L chains into HEK 293 cells.
  vii) Purify expressed caninized antibody from HEK 293 supernatant.
  viii) Test purified caninized antibody for binding to canine IL-4 receptor alpha chain.

The application of the above outlined steps resulted in a set of caninized H and L chain sequences for which the SEQ ID NOs. are listed in Table 5 below.

TABLE 5

CANINIZED FULL-LENGTH HEAVY AND LIGHT CHAIN SEQUENCES

| H chain or L chain | Nucleic Acid | Amino Acid |
| --- | --- | --- |
| vH1 | SEQ ID NO: 163 | SEQ ID NO: 164 |
| vH2 | SEQ ID NO: 165 | SEQ ID NO: 166 |
| vH3 | SEQ ID NO: 167 | SEQ ID NO: 168 |
| vL1 | SEQ ID NO: 169 | SEQ ID NO: 170 |
| vL2 | SEQ ID NO: 171 | SEQ ID NO: 172 |
| vL3 | SEQ ID NO: 173 | SEQ ID NO: 174 |

Figure 4:
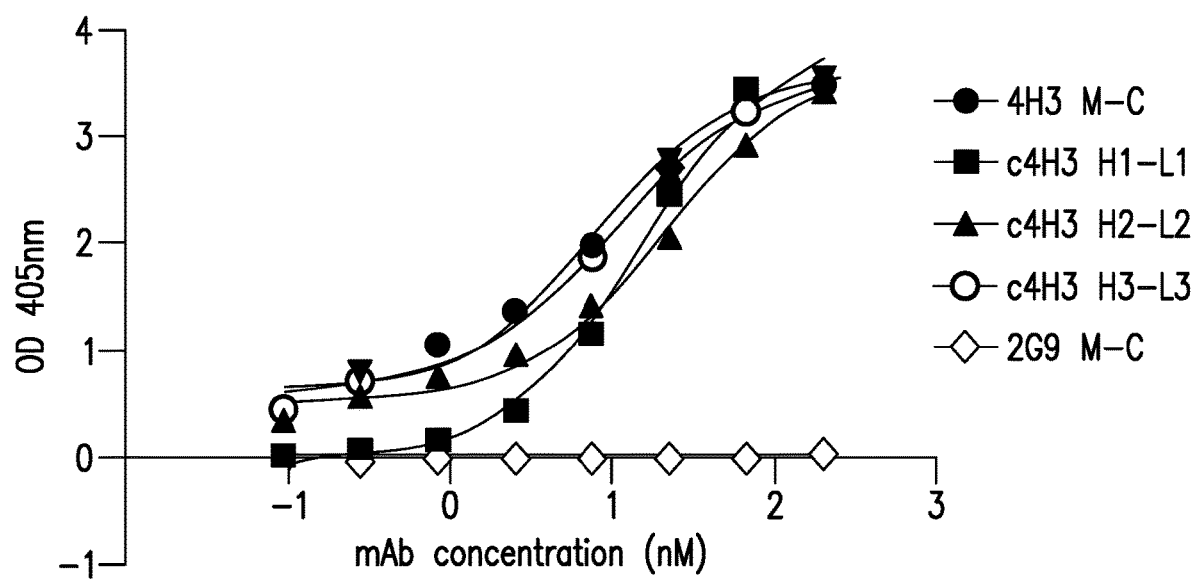
FIG. 4 depicts the binding of chimeric and caninized monoclonal antibodies to canine IL-4R$_\alpha$ as evaluated by ELISA. The dose-dependent reactivity of caninized monoclonal antibodies against canine IL-4 receptor alpha chain is as follows: 4H3 M-C (●); 2G9 M-C (◇); c4H3 H1-L1 (■); c4H3 H2-L2(▲); c4H3 H3-L3 (○).

The present invention provides caninized antibodies formed by the combination of various caninized heavy and light chains listed in the Table 5 above; such antibodies have particularly tight binding with canine IL-4 receptor alpha. In a particular embodiment the heavy chain comprises the amino acid sequence of SEQ ID NO: 164 and the light chain comprises the amino acid sequence of SEQ ID NO: 170. In a more particular embodiment of this type, the heavy chain is encoded by the nucleotide sequence of SEQ ID NO: 163 and the light chain is encoded by the nucleotide sequence of SEQ ID NO: 169. In another embodiment the heavy chain comprises the amino acid sequence of SEQ ID NO: 166 and the light chain comprises the amino acid sequence of SEQ ID NO: 172. In a more particular embodiment of this type, the heavy chain is encoded by the nucleotide sequence of SEQ ID NO: 165 and the light chain is encoded by the nucleotide sequence of SEQ ID NO: 171. In still another embodiment the heavy chain comprises the amino acid sequence of SEQ ID NO: 168 and the light chain comprises the amino acid sequence of SEQ ID NO: 174. In a more particular embodiment of this type, the heavy chain is encoded by the nucleotide sequence of SEQ ID NO: 167 and the light chain is encoded by the nucleotide sequence of SEQ ID NO: 173. Binding studies to IL-4 receptor alpha by these caninized antibodies are depicted in FIG. 4, as described in Example 8, below.

As indicated above, the Fc portion of the caninized antibodies is based on modified sequences of canine IgG-B in order to remove ADCC and CDC effector functions. The Fc regions of these antibodies may be replaced with a modified Fc from other canine IgG isotypes and/or can be combined with substitute hinge regions as discussed above, and exemplified and disclosed in U.S. provisional application 62/030,812 filed Jul. 30, 2014; U.S. provisional application 62/057,541 filed Sep. 30, 2014; U.S. provisional application 62/092,496 filed Dec. 16, 2014; U.S. provisional application 62/172,511, filed Jun. 8, 2015; and WO 2015/091910, the contents of all of which are hereby incorporated by reference in their entireties.

```
CANINZED 4H3 (vH1)
                                                                  SEQ ID NO: 163
GAGGTGCAGCTGGTGGAGAGCGGAGGCGACCTGGTGAAACCCGGAGGCAGCCTGAGACTGAGCTGTGTGGCCAGCGGCT

ACACCTTCACCAACTACTGGATTCATTGGGTGAGGCAGGCTCCCGGCAAAGGACTGCAGTGGGTGGCCAGGATTGATCC

CAACAGCGGCGGCACCAAGTACAACGAGAAGTTCAAGAGCAGGTTCACCATCAGCAGGGACAACGCCAAGAACACCCTC

TACCTGCAGATGAACAGCCTGAGGGCCGAGGACACCGCCGTGTACTACTGCACCAGGTTCGGCAGCACCTACGGCTTCG

CCTACTGGGGCCAAGGCACCCTGGTGACCGTGAGCAGCGCTTCCACAACCGCGCCATCAGTCTTTCCGTTGGCCCCATC

ATGCGGGTCGACGAGCGGATCGACTGTGGCCCTGGCGTGCTTGGTGTCGGGATACTTTCCCGAACCCGTCACGGTCAGC

TGGAACTCCGGATCGCTTACGAGCGGTGTGCATACGTTCCCCTCGGTCTTGCAATCATCAGGGCTCTACTCGCTGTCGA
```

-continued

```
GCATGGTAACGGTGCCCTCATCGAGGTGGCCCTCCGAAACGTTCACATGTAACGTAGCACATCCAGCCTCCAAAACCAA
GGTGGATAAACCCGTGCCGAAAAGAGAGAATGGGCGGGTGCCTCGACCCCCTGATTGCCCCAAGTGTCCGGCTCCGGAA
ATGCTCGGTGGACCCTCAGTGTTTATCTTCCCTCCGAAGCCCAAGGACACTCTGCTGATCGCGCGCACTCCAGAAGTAA
CATGTGTAGTGGTGGCACTTGATCCCGAGGACCCCGAAGTCCAGATCTCCTGGTTTGTAGATGGGAAACAGATGCAGAC
CGCAAAAACTCAACCCAGAGAGGAGCAGTTCGCAGGAACATACCGAGTGGTATCCGTCCTTCCGATTGGCCACCAGGAC
TGGTTGAAAGGGAAGCAGTTTACGTGTAAAGTCAACAATAAGGCGTTGCCTAGCCCTATTGAGCGGACGATTTCGAAAG
CTAGGGACAGGCCCACCAGCCATCGGTCTATGTCCTTCCGCCTTCCCGCGAGGAGCTCTCGAAGAATACAGTGAGCCT
TACATGCCTCATTAAGGATTTCTTCCCGCCTGATATCGACGTAGAGTGGCAATCAAACGGTCAACAGGAGCCGGAATCC
AAGTATAGAACCACTCCGCCCCAGCTTGACGAGGACGGATCATACTTTTTGTATTCAAAACTGTCGGTGGATAAGAGCC
GGTGGCAGAGAGGTGACACCTTCATCTGTGCGGTGATGCACGAAGCACTCCATAATCACTACACCCAAGAGAGCCTCTC
GCATTCCCCCGGAAAG
```

SEQ ID NO: 164

```
EVQLVESGGDLVKPGGSLRLSCVASGYTFTNYWIHWVRQAPGKGLQWVARIDPNSGGTKYNEKFKSRFTISRDNAKNTL
YLQMNSLRAEDTAVYYCTRFGSTYGFAYWGQTLVTVSSASTTAPSVFPLAPSCGSTSGSTVALACLVSGYFPEPVTVS
WNSGSLTSGVHTFPSVLQSSGLYSLSSMVTVPSSRWPSETFTCNVAHPASKTKVDKPVPKRENGRVPRPPDCPKCPAPE
MLGGPSVFIFPPKPKDTLLIARTPEVTCVVVALDPEDPEVQISWFVDGKQMQTAKTQPREEQFAGTYRVVSVLPIGHQD
WLKGKQFTCKVNNKALPSPIERTISKARGQAHQPSVYVLPPSREELSKNTVSLTCLIKDFFPPDIDVEWQSNGQQEPES
KYRTTPPQLDEDGSYFLYSKLSVDKSRWQRGDTFICAVMHEALHNHYTQESLSHSPGK
```

CANINZED 4H3 (vH2)

SEQ ID NO: 165

```
GAGGTGCAGCTGGTGGAGAGCGGCGGAGATCTGGTGAAGCCCGGCGGAAGCCTGAGACTGAGCTGTGTGGCCAGCGGCT
ACACCTTCACCAACTACTGGATTCATTGGGTGAGACAGGCCCCTGGCAAGGGCCTGCAGTGGATCGGCAGGATCGACCC
CAACAGCGGCGGCACCAAGTACAACGAGAAGTTCAAGAGCAAGGCCACCCTGAGCGTGGACAAGGCCAAGAACACCCTG
TACCTGCAGATGAACTCCCTGAGGGCCGAGGACACCGCCGTGTACTACTGCGCCGCCTTTGGCAGCACCTACGGCTTCG
CCTACTGGGGCCAGGGAACCCTGGTGACCGTGAGCAGCGCTTCCACAACGCGCCATCAGTCTTTCCGTTGGCCCCATC
ATGCGGGTCGACGAGCGGATCGACTGTGGCCCTGGCGTGCTTGGTGTCGGGATACTTTCCCGAACCCGTCACGGTCAGC
TGGAACTCCGGATCGCTTACGAGCGGTGTGCATACGTTCCCCTCGGTCTTGCAATCATCAGGGCTCTACTCGCTGTCGA
GCATGGTAACGGTGCCCTCATCGAGGTGGCCCTCCGAAACGTTCACATGTAACGTAGCACATCCAGCCTCCAAAACCAA
GGTGGATAAACCCGTGCCGAAAAGAGAGAATGGGCGGGTGCCTCGACCCCCTGATTGCCCCAAGTGTCCGGCTCCGGAA
ATGCTCGGTGGACCCTCAGTGTTTATCTTCCCTCCGAAGCCCAAGGACACTCTGCTGATCGCGCGCACTCCAGAAGTAA
CATGTGTAGTGGTGGCACTTGATCCCGAGGACCCCGAAGTCCAGATCTCCTGGTTTGTAGATGGGAAACAGATGCAGAC
CGCAAAAACTCAACCCAGAGAGGAGCAGTTCGCAGGAACATACCGAGTGGTATCCGTCCTTCCGATTGGCCACCAGGAC
TGGTTGAAAGGGAAGCAGTTTACGTGTAAAGTCAACAATAAGGCGTTGCCTAGCCCTATTGAGCGGACGATTTCGAAAG
CTAGGGACAGGCCCACCAGCCATCGGTCTATGTCCTTCCGCCTTCCCGCGAGGAGCTCTCGAAGAATACAGTGAGCCT
TACATGCCTCATTAAGGATTTCTTCCCGCCTGATATCGACGTAGAGTGGCAATCAAACGGTCAACAGGAGCCGGAATCC
AAGTATAGAACCACTCCGCCCCAGCTTGACGAGGACGGATCATACTTTTTGTATTCAAAACTGTCGGTGGATAAGAGCC
GGTGGCAGAGAGGTGACACCTTCATCTGTGCGGTGATGCACGAAGCACTCCATAATCACTACACCCAAGAGAGCCTCTC
GCATTCCCCCGGAAAG
```

SEQ ID NO: 166

```
EVQLVESGGDLVKPGGSLRLSCVASGYTFTNYWIHWVRQAPGKGLQWIGRIDPNSGGTKYNEKFKSKATLSVDKAKNTL
YLQMNSLRAEDTAVYYCAAFGSTYGFAYWGQTLVTVSSASTTAPSVFPLAPSCGSTSGSTVALACLVSGYFPEPVTVS
WNSGSLTSGVHTFPSVLQSSGLYSLSSMVTVPSSRWPSETFTCNVAHPASKTKVDKPVPKRENGRVPRPPDCPKCPAPE
MLGGPSVFIFPPKPKDTLLIARTPEVTCVVVALDPEDPEVQISWFVDGKQMQTAKTQPREEQFAGTYRVVSVLPIGHQD
```

WLKGKQFTCKVNNKALPSPIERTISKARGQAHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQESLSHSPGK

CANINZED 4H3 (vH3):

SEQ ID NO: 167

GAGGTGCAGCTGGTGGAGAGCGGCGGCGATCTGGTGAAGCCTGGCGAAGCCTGAGACTGAGCTGCGTGGCCAGCGGCT

ACACCTTCACCAACTACTGGATTCATTGGATGAGGCAGGCCCCTGGCAAGGGACTGCAGTGGATCGGCAGAATCGACCC

CAACAGCGGCGGCACCAAGTACAACGAGAAGTTCAAGAGCAAGGCCACCCTGAGCGTGGACAAGGCCAAGAACACCGCC

TACATGCAGCTGAACAGCCTGAGGGCCGAGGACACCGCCGTGTACTACTGCGCCGCCTTTGGCAGCACCTACGGCTTCG

CCTATTGGGGCCAGGGCACCCTGGTGACCGTGAGCAGCGCTTCCACAACCGCGCCATCAGTCTTTCCGTTGGCCCCATC

ATGCGGGTCGACGAGCGGATCGACTGTGGCCCTGGCGTGCTTGGTGTCGGGATACTTTCCCGAACCCGTCACGGTCAGC

TGGAACTCCGGATCGCTTACGAGCGGTGTGCATACGTTCCCCTCGGTCTTGCAATCATCAGGGCTCTACTCGCTGTCGA

GCATGGTAACGGTGCCCTCATCGAGGTGGCCCTCCGAAACGTTCACATGTAACGTAGCACATCCAGCCTCCAAAACCAA

GGTGGATAAACCCGTGCCGAAAAGAGAGAATGGGCGGGTGCCTCGACCCCCTGATTGCCCCAAGTGTCCGGCTCCGGAA

ATGCTCGGTGGACCCTCAGTGTTTATCTTCCCTCCGAAGCCCAAGGACACTCTGCTGATCGCGCGCACTCCAGAAGTAA

CATGTGTAGTGGTGGCACTTGATCCCGAGGACCCCGAAGTCCAGATCTCCTGGTTTGTAGATGGGAAACAGATGCAGAC

CGCAAAAACTCAACCCAGAGAGGAGCAGTTCGCAGGAACATACCGAGTGGTATCCGTCCTTCCGATTGGCCACCAGGAC

TGGTTGAAAGGGAAGCAGTTTACGTGTAAAGTCAACAATAAGGCGTTGCCTAGCCCTATTGAGCGGACGATTTCGAAAG

CTAGGGGACAGGCCCACCAGCCATCGGTCTATGTCCTTCCGCCTTCCCGCGAGGAGCTCTCGAAGAATACAGTGAGCCT

TACATGCCTCATTAAGGATTTCTTCCCGCCTGATATCGACGTAGAGTGGCAATCAAACGGTCAACAGGAGCCGGAATCC

AAGTATAGAACCACTCCGCCCCAGCTTGACGAGGACGGATCATACTTTTTGTATTCAAAACTGTCGGTGGATAAGAGCC

GGTGGCAGAGAGGTGACACCTTCATCTGTGCGGTGATGCACGAAGCACTCCATAATCACTACACCCAAGAGAGCCTCTC

GCATTCCCCCGGAAAG

SEQ ID NO: 168

EVQLVESGGDLVKPGGSLRLSCVASGYTFTNYWIHWMRQAPGKGLQWIGRIDPNSGGTKYNEKFKSKATLSVDKAKNTA

YMQLNSLRAEDTAVYYCAAFGSTYGFAYWGQGTLVTVSSASTTAPSVFPLAPSCGSTSGSTVALACLVSGYFPEPVTVS

WNSGSLTSGVHTFPSVLQSSGLYSLSSMVTVPSSRWPSETFTCNVAHPASKTKVDKPVPKRENGRVPRPPDCPKCPAPE

MLGGPSVFIFPPKPKDTLLIARTPEVTCVVVALDPEDPEVQISWFVDGKQMQTAKTQPREEQFAGTYRVVSVLPIGHQD

WLKGKQFTCKVNNKALPSPIERTISKARGQAHQPSVYVLPPSREELSKNTVSLTCLIKDFFPPDIDVEWQSNGQQEPES

KYRTTPPQLDEDGSYFLYSKLSVDKSRWQRGDTFICAVMHEALHNHYTQESLSHSPGK

CANINZED 4H3 (vL1)

SEQ ID NO: 169

GACATCGTGATGACCCAGACCCCTCTGAGCCTGTCCGTGAGCCCTGGCGAACCTGCCAGCATCAGCTGCAAGAGCAGCC

AGAGCCTGCTGAACAGCAGGACCAGGAAGAACTACCTGGCCTGGTTCAGACAGAAGCCCGGCCAGAGCCCCCAGAGACT

GATCTACTGGGCCAGCACCAGAGAGAGCGGCGTGCCTGACAGATTTAGCGGCAGCGGCAGCGGCACAGACTTCACCCTG

AGGATCAGCAGAGTGGAGGCCGACGATGCCGGCGTGTACTACTGCAAGCAGAGCTACAACCTGTACACCTTCGGCCAGG

GCACCAAGGTGGAGATCAAGAGGAACGACGCTCAGCCAGCCGTGTACCTCTTCCAGCCTTCGCCGGACCAGCTTCATAC

GGGGTCAGCGTCGGTGGTGTGCCTGTTGAACTCGTTTTACCCCAAGGACATTAACGTGAAGTGGAAGGTAGACGGGGTA

ATTCAAGACACTGGCATTCAAGAGTCCGTCACGGAACAAGACTCAAAAGACTCAACGTATTCACTGTCGTCAACCTTGA

CGATGTCAAGCACCGAGTATCTTAGCCATGAGCTGTATTCGTGCGAGATCACCCACAAGTCCCTCCCCTCCACTCTTAT

CAAATCCTTTCAGCGGTCGGAATGTCAGCGGGTCGAT

SEQ ID NO: 170
DIVMTQTPLSLSVSPGEPASISCKSSQSLLNSRTRKNYLAWFRQKPGQSPQRLIYWASTRESGVPDRFSGSGSGTDFTL

RISRVEADDAGVYYCKQSYNLYTFGQGTKVEIKRNDAQPAVYLFQPSPDQLHTGSASVVCLLNSFYPKDINVKWKVDGV

IQDTGIQESVTEQDSKDSTYSLSSTLTMSSTEYLSHELYSCEITHKSLPSTLIKSFQRSECQRVD

CANINZED 4H3 (vL2)
SEQ ID NO: 171
GACATCGTGATGACCCAGACCCCTCTGAGCCTGAGCGTGAGCCCTGGAGAGCCTGCCAGCATCAGCTGCAAGAGCAGCC

AGAGCCTGCTGAACAGCAGGACCAGGAAGAACTACCTGGCCTGGTACAGGCAGAAGCCTGGCCAGAGCCCCCAGCTGCT

GATCTACTGGGCCAGCACCAGAGAGAGCGGAGTGCCTGACAGGTTCAGCGGAAGCGGCAGCGGCACCGACTTCACCCTG

AGGATCAGCAGAGTGGAGGCCGATGACGCCGGCGTGTACTACTGCAAGCAGAGCTACAACCTGTACACCTTCGGCCAGG

GCACCAAGGTGGAGATCAAGAGGAACGACGCTCAGCCAGCCGTGTACCTCTTCCAGCCTTCGCCGGACCAGCTTCATAC

GGGGTCAGCGTCGGTGGTGTGCCTGTTGAACTCGTTTTACCCCAAGGACATTAACGTGAAGTGGAAGGTAGACGGGGTA

ATTCAAGACACTGGCATTCAAGAGTCCGTCACGGAACAAGACTCAAAAGACTCAACGTATTCACTGTCGTCAACCTTGA

CGATGTCAAGCACCGAGTATCTTAGCCATGAGCTGTATTCGTGCGAGATCACCCACAAGTCCCTCCCCTCCACTCTTAT

CAAATCCTTTCAGCGGTCGGAATGTCAGCGGGTCGAT

SEQ ID NO: 172
DIVMTQTPLSLSVSPGEPASISCKSSQSLLNSRTRKNYLAWYRQKPGQSPQLLIYWASTRESGVPDRFSGSGSGTDFTL

RISRVEADDAGVYYCKQSYNLYTFGQGTKVEIKRNDAQPAVYLFQPSPDQLHTGSASVVCLLNSFYPKDINVKWKVDGV

IQDTGIQESVTEQDSKDSTYSLSSTLTMSSTEYLSHELYSCEITHKSLPSTLIKSFQRSECQRVD

CANINZED 4H3 (vL3)
SEQ ID NO: 173
GACATCGTGATGACCCAGACCCCTCTGAGCCTGAGCGTGAGCCCTGGAGAGCCTGCCAGCATCAGCTGCAAGAGCAGCC

AGAGCCTGCTGAACAGCAGGACCAGGAAGAACTACCTGGCCTGGTACCAGCAGAAGCCTGGCCAGAGCCCCCAGCTGCT

GATCTACTGGGCCAGCACCAGAGAGAGCGGAGTGCCTGACAGGTTCAGCGGAAGCGGCAGCGGCACCGACTTCACCCTG

AGGATCAGCAGAGTGGAGGCCGATGACGCCGGCGTGTACTACTGCAAGCAGAGCTACAACCTGTACACCTTCGGCCAGG

GCACCAAGGTGGAGATCAAGAGGAACGACGCTCAGCCAGCCGTGTACCTCTTCCAGCCTTCGCCGGACCAGCTTCATAC

GGGGTCAGCGTCGGTGGTGTGCCTGTTGAACTCGTTTTACCCCAAGGACATTAACGTGAAGTGGAAGGTAGACGGGGTA

ATTCAAGACACTGGCATTCAAGAGTCCGTCACGGAACAAGACTCAAAAGACTCAACGTATTCACTGTCGTCAACCTTGA

CGATGTCAAGCACCGAGTATCTTAGCCATGAGCTGTATTCGTGCGAGATCACCCACAAGTCCCTCCCCTCCACTCTTAT

CAAATCCTTTCAGCGGTCGGAATGTCAGCGGGTCGAT

SEQ ID NO: 174
DIVMTQTPLSLSVSPGEPASISCKSSQSLLNSRTRKNYLAWYQQKPGQSPQLLIYWASTRESGVPDRFSGSGSGTDFTL

RISRVEADDAGVYYCKQSYNLYTFGQGTKVEIKRNDAQPAVYLFQPSPDQLHTGSASVVCLLNSFYPKDINVKWKVDGV

IQDTGIQESVTEQDSKDSTYSLSSTLTMSSTEYLSHELYSCEITHKSLPSTLIKSFQRSECQRVD

Example 8

Reactivity of Caninized Antibodies Against Canine IL-4 Receptor Alpha

The caninized antibodies were tested for reactivity with canine IL-4 receptor alpha as follows:

1. Coat 200 ng/well of IL-4 receptor alpha on an immunoplate and incubate the plate at 4° C. overnight.
2. Wash the plate 3 times with phosphate buffered saline (PBS) containing 0.05% Tween 20 (PBST).
3. Block the plate with 0.5% bovine serum albumin (BSA) in PBS for 45-60 min at room temperature.
4. Wash the plate 3 times with PBST.
5. Three-fold dilute the caninized antibody in each column or row of dilution plate starting at 0.3 µg/mL.
6. Transfer the diluted caninized antibody into each column or row of the immunoplate, and incubate the plate for 45-60 min at room temperature.
7. Wash the plate 3 times with PBST.
8. Add 1:4000 diluted horseradish peroxidase labeled anti-canine IgG Fc into each well of the plate, and then incubate the plate for 45-60 min at room temperature.
9. Wash the plate 3 times with PBST.
10. Add 3,3',5,5'-tetramethylbenzidine (TMB) Substrate into each well of the plate, and incubate the plate for 10 to 15 min at room temperature to develop the color.
11. Add 100 µL 1.5 M phosphoric acid into each well to stop the reaction. Read plate at 450 nm with 540 nm reference wavelength.

As depicted in FIG. 4, the binding of five (5) antibodies to the IL-4 receptor alpha was studied: 4H3 M-C, c4H3

H1-L1, c4H3 H2-L2, c4H3 H3-L3, and 2G9 M-C. 2G9 M-C was used as a negative control antibody. 4H3 M-C is a chimeric antibody consisting of the mouse variable heavy regions of the presently disclosed 4H3 antibody together with canine constant regions, and the light chain from the mouse 4H3 antibody. c4H3 H1-L1, c4H3 H2-L2, c4H3 H3-L3 are three caninized variants of the mouse 4H3 antibody, and include specific heavy chains and light chains as depicted in Table 5 above. 2G9 M-C is a chimeric antibody consisting of the mouse variable heavy regions of a mouse antibody to an antigen that is completely unrelated to the IL-4 receptor alpha together with canine constant regions, and the light chain from the mouse antibody to that unrelated antigen. Consistently, 2G9 M-C did not bind to the IL-4 receptor alpha, whereas the remaining four antibodies studied, i.e., 4H3 M-C, c4H3 H1-L1, c4H3 H2-L2, and c4H3 H3-L3, all bound relatively tightly (see, FIG. 4).

We claim:

1. An antibody or antigen binding fragment thereof that binds to canine interleukin-4 receptor α (IL-4R$_\alpha$), wherein the antibody or antigen binding fragment thereof comprises:
   (i) a light chain variable region (VL) comprising a VL complementarity determining region (CDR) 1, a VL CDR2, and a VL CDR3 having an amino acid sequence of a VL CDR1, a VL CDR2, and a VL CDR3, respectively, of a VL having the amino acid sequence of SEQ ID NO:120; and
   (ii) a VH comprising a VH CDR1, a VH CDR2, and a VH CDR3 having an amino acid sequence of a VH CDR1, a VH CDR2, and a VH CDR3, respectively, of a VH having the amino acid sequence of SEQ ID NO:118.

2. The antibody or antigen binding fragment thereof of claim 1, wherein the antibody or the antigen-binding fragment thereof comprises:
   (a) a VL comprising: a VL CDR1 comprising the amino acid sequence of SEQ ID NO: 129, a VL CDR2 comprising the amino acid sequence of SEQ ID NO:134, and a VL CDR3 comprising the amino acid sequence of SEQ ID NO:137; and
   (b) a VH comprising: a VH CDR1 comprising the amino acid sequence of SEQ ID NO: 140, a VH CDR2 comprising the amino acid sequence of SEQ ID NO:146, and a VH CDR3 comprising the amino acid sequence of SEQ ID NO:151.

3. The antibody or antigen binding fragment thereof of claim 1, wherein the antibody or the antigen-binding fragment thereof comprises a VL comprising an amino acid sequence having at least 95% identity to the amino acid sequence of SEQ ID NO: 120.

4. The antibody or antigen binding fragment thereof of claim 1, wherein the antibody or the antigen-binding fragment thereof comprises a VL comprising the amino acid sequence of SEQ ID NO:120.

5. The antibody or antigen binding fragment thereof of claim 1, wherein the antibody or the antigen-binding fragment thereof comprises a VH comprising an amino acid sequence having at least 95% identity to the amino acid sequence of SEQ ID NO: 118.

6. The antibody or antigen binding fragment thereof of claim 1, wherein the antibody or the antigen-binding fragment thereof comprises a VH comprising the amino acid sequence of SEQ ID NO:118.

7. The antibody or antigen binding fragment thereof of claim 1, wherein the antibody or the antigen-binding fragment thereof comprises a VL comprising an amino acid sequence having at least 95% identity to the amino acid sequence of SEQ ID NO: 120; and a VH comprising an amino acid sequence having at least 95% identity to the amino acid sequence of SEQ ID NO:118.

8. The antibody or antigen binding fragment thereof of claim 1, wherein the antibody or the antigen-binding fragment thereof comprises a VL comprising the amino acid sequence of SEQ ID NO:120; and a VH comprising the amino acid sequence of SEQ ID NO: 118.

9. The antibody or antigen binding fragment thereof of claim 1, wherein the antibody or antigen binding fragment is a caninized antibody or a caninized antigen binding fragment.

10. The antibody or antigen binding fragment thereof of claim 9, wherein the antibody or antigen binding fragment thereof comprises a hinge region selected from a canine IgGA hinge region, a canine IgGB hinge region, a canine IgGC hinge region, and a canine IgGD hinge region.

11. The antibody or antigen binding fragment thereof of claim 9, wherein the antibody or antigen binding fragment thereof comprises a hinge region comprising the amino acid sequence of SEQ ID NO:101, SEQ ID NO:102, SEQ ID NO:103, and SEQ ID NO: 104.

12. The antibody or antigen binding fragment thereof of claim 9, wherein the antibody or antigen binding fragment thereof comprises a canine fragment crystallizable (cFc) region selected from a canine IgGA Fc region, a canine IgGB Fc region, a canine IgGC Fc region, and a canine IgGD Fc region.

13. The antibody or antigen binding fragment thereof of claim 12, wherein the cFc region is selected from a genetically modified canine IgGA Fc region, a genetically modified canine IgGB Fc region, a genetically modified canine IgGC Fc region, and a genetically modified canine IgGD Fc region.

14. The antibody or antigen binding fragment thereof of claim 13, wherein the cFc region is a genetically modified canine IgGB Fc region comprising one or more of the amino acid substitution selected from P4A, D31A, N63A, G64P, T65A, A93G, and P95A in the native canine IgGB Fc region.

15. The antibody or antigen binding fragment thereof of claim 1, wherein when bound to canine IL-4R$_\alpha$, binds to at least one amino acid residue within the amino acid sequence of SEQ ID NO:125, or at least one amino acid residue within the amino acid sequence of SEQ ID NO:126, or any combination thereof.

16. The antibody or antigen binding fragment thereof of claim 1, wherein when bound to canine IL-4R$_\alpha$, blocks the binding of canine IL-4R$_\alpha$ to one or more of canine interleukin-4 and canine interleukin-13.

17. A pharmaceutical composition comprising the antibody or antigen binding fragment thereof of claim 1 and a pharmaceutically acceptable carrier or diluent.

* * * * *

SEQUENCE LISTING

<160> NUMBER OF SEQ ID NOS: 174

<210> SEQ ID NO 1
<211> LENGTH: 2469
<212> TYPE: DNA
<213> ORGANISM: Canis familiaris

<400> SEQUENCE: 1

```
atgggcagac tgtgcagcgg cctgaccttc cccgtgagct gcctggtgct ggtgtgggtg      60
gccagcagcg gcagcgtgaa ggtgctgcac gagcccagct gcttcagcga ctacatcagc     120
accagcgtgt gccagtggaa gatggaccac cccaccaact gcagcgccga gctgagactg     180
agctaccagc tggacttcat gggcagcgag aaccacacct gcgtgcccga gaacagagag     240
gacagcgtgt gcgtgtgcag catgcccatc gacgacgccg tggaggccga cgtgtaccag     300
ctggacctgt gggccggcca gcagctgctg tggagcggca gcttccagcc cagcaagcac     360
gtgaagccca gaacccccgg caacctgacc gtgcacccca acatcagcca cctggctg      420 ctgatgtgga ccaaccccta ccccaccgag aaccacctgc acagcgagct gacctacatg     480
gtgaacgtga gcaacgacaa cgaccccgag gacttcaagg tgtacaacgt gacctacatg     540
ggccccaccc tgagactggc cgccagcacc ctgaagagcg cgccagcta cagcgccaga     600 gtgagagcct gggcccagac ctacaacagc acctggagcg actggagccc cagcaccacc     660
tggctgaact actacgagcc ctgggagcag cacctgcccc tgggcgtgag catcagctgc     720
ctggtgatcc tggccatctg cctgagctgc tacttcagca tcatcaagat caagaagggc     780
tggtgggacc agatccccaa ccccgcccac agccccctgg tggccatcgt gatccaggac     840
agccaggtga gcctgtgggg caagagaagc agaggccagg agcccgccaa gtgccccac      900 tggaagacct gcctgaccaa gctgctgccc tgcctgctgg agcacggcct gggcagagag     960
gaggagagcc ccaagaccgc caagaacggc cccctgcagg ccccggcaa gcccgcctgg    1020 tgccccgtgg aggtgagcaa gaccatcctg tggcccgaga gcatcagcgt ggtgcagtgc    1080
gtggagctga gcgaggcccc cgtggacaac gaggaggagg aggaggtgga ggaggacaag    1140
agaagcctgt gccccagcct ggagggcagc ggcggcagct tccaggaggg cagagagggc    1200
atcgtggcca gactgaccga gagcctgttc ctggacctgc tgggcggcga aacggcggc     1260 ttctgccccc agggcctgga ggagagctgc ctgccccccc cagcggcag cgtgggcgcc    1320 cagatgccct gggcccagtt ccccagagcc ggccccgag ccgcccccga gggccccgag    1380
cagcccagaa gacccgagag cgccctgcag gccagcccca cccagagcgc cggcagcagc    1440
gccttccccg agccccccc cgtggtgacc gacaacccca cctacagaag cttcggcagc    1500
ttcctgggcc agagcagcga ccccgcgac ggcgacagcg acccgagct ggccgacaga    1560 cccgcgagg ccgaccccgg catccccagc gccccccagc ccccgagcc ccgccgcc     1620 ctgcagcccc agcccgagag ctgggagcag atcctgagac agagcgtgct gcagcacaga    1680
gccgcccccg cccccggcc cggccccgc agcggctaca gagagttcac ctgcgccgtg    1740
```

```
aagcagggca gcgcccccga cgccggcggc cccggcttcg gccccagcgg cgaggccggc    1800
tacaaggcct tctgcagcct gctgcccggc ggcgccacct gccccggcac cagcggcggc    1860
gaggccggca gcggcgaggg cggctacaag cccttccaga gcctgacccc cggctgcccc    1920
ggcgccccca ccccgtgcc cgtgcccctg ttcaccttcg gcctggacac cgagcccccc    1980
ggcagccccc aggacagcct gggcgccggc agcagccccg agcacctggg cgtggagccc    2040
gccggcaagg aggaggacag cagaaagacc ctgctggccc ccgagcaggc caccgacccc    2100
ctgagagacg acctggccag cagcatcgtg tacagcgccc tgacctgcca cctgtgcggc    2160
cacctgaagc agtggcacga ccaggaggag agaggcaagg cccacatcgt gcccagcccc    2220
tgctgcggct gctgctgcgg cgacagaagc agcctgctgc tgagccccct gagagccccc    2280
aacgtgctgc ccggcggcgt gctgctggag gccagcctga ccccgccag cctggtgccc    2340 agcggcgtga gcaaggaggg caagagcagc cccttcagcc agcccgccag cagcagcgcc    2400
cagagcagca gccagacccc caagaagctg gccgtgctga gcaccgagcc cacctgcatg    2460
agcgccagc                                                           2469

<210> SEQ ID NO 2
<211> LENGTH: 823
<212> TYPE: PRT
<213> ORGANISM: Canis familiaris

<400> SEQUENCE: 2

Met Gly Arg Leu Cys Ser Gly Leu Thr Phe Pro Val Ser Cys Leu Val
1               5                   10                  15

Leu Val Trp Val Ala Ser Ser Gly Ser Val Lys Val Leu His Glu Pro
            20                  25                  30

Ser Cys Phe Ser Asp Tyr Ile Ser Thr Ser Val Cys Gln Trp Lys Met
        35                  40                  45

Asp His Pro Thr Asn Cys Ser Ala Glu Leu Arg Leu Ser Tyr Gln Leu
    50                  55                  60

Asp Phe Met Gly Ser Glu Asn His Thr Cys Val Pro Glu Asn Arg Glu
65                  70                  75                  80

Asp Ser Val Cys Val Cys Ser Met Pro Ile Asp Asp Ala Val Glu Ala
                85                  90                  95

Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
        115                 120                 125

Leu Thr Val His Pro Asn Ile Ser His Thr Trp Leu Leu Met Trp Thr
    130                 135                 140

Asn Pro Tyr Pro Thr Glu Asn His Leu His Ser Glu Leu Thr Tyr Met
145                 150                 155                 160

Val Asn Val Ser Asn Asp Asn Pro Glu Asp Phe Lys Val Tyr Asn
                165                 170                 175

Val Thr Tyr Met Gly Pro Thr Leu Arg Leu Ala Ala Ser Thr Leu Lys
            180                 185                 190

Ser Gly Ala Ser Tyr Ser Ala Arg Val Arg Ala Trp Ala Gln Thr Tyr
        195                 200                 205

Asn Ser Thr Trp Ser Asp Trp Ser Pro Ser Thr Thr Trp Leu Asn Tyr
    210                 215                 220

Tyr Glu Pro Trp Glu Gln His Leu Pro Leu Gly Val Ser Ile Ser Cys
225                 230                 235                 240
```

-continued

```
Leu Val Ile Leu Ala Ile Cys Leu Ser Cys Tyr Phe Ser Ile Ile Lys
                245                 250                 255

Ile Lys Lys Gly Trp Trp Asp Gln Ile Pro Asn Pro Ala His Ser Pro
            260                 265                 270

Leu Val Ala Ile Val Ile Gln Asp Ser Gln Val Ser Leu Trp Gly Lys
                275                 280                 285

Arg Ser Arg Gly Gln Glu Pro Ala Lys Cys Pro His Trp Lys Thr Cys
            290                 295                 300

Leu Thr Lys Leu Leu Pro Cys Leu Leu Glu His Gly Leu Gly Arg Glu
305                 310                 315                 320

Glu Glu Ser Pro Lys Thr Ala Lys Asn Gly Pro Leu Gln Gly Pro Gly
                325                 330                 335

Lys Pro Ala Trp Cys Pro Val Glu Val Ser Lys Thr Ile Leu Trp Pro
            340                 345                 350

Glu Ser Ile Ser Val Val Gln Cys Val Glu Leu Ser Glu Ala Pro Val
                355                 360                 365

Asp Asn Glu Glu Glu Glu Val Glu Glu Asp Lys Arg Ser Leu Cys
            370                 375                 380

Pro Ser Leu Glu Gly Ser Gly Ser Phe Gln Glu Gly Arg Glu Gly
385                 390                 395                 400

Ile Val Ala Arg Leu Thr Glu Ser Leu Phe Leu Asp Leu Leu Gly Gly
                405                 410                 415

Glu Asn Gly Gly Phe Cys Pro Gln Gly Leu Glu Glu Ser Cys Leu Pro
            420                 425                 430

Pro Pro Ser Gly Ser Val Gly Ala Gln Met Pro Trp Ala Gln Phe Pro
            435                 440                 445

Arg Ala Gly Pro Arg Ala Ala Pro Glu Gly Pro Glu Gln Pro Arg Arg
450                 455                 460

Pro Glu Ser Ala Leu Gln Ala Ser Pro Thr Gln Ser Ala Gly Ser Ser
465                 470                 475                 480

Ala Phe Pro Glu Pro Pro Val Val Thr Asp Asn Pro Ala Tyr Arg
            485                 490                 495

Ser Phe Gly Ser Phe Leu Gly Gln Ser Ser Asp Pro Gly Asp Gly Asp
            500                 505                 510

Ser Asp Pro Glu Leu Ala Asp Arg Pro Gly Glu Ala Asp Pro Gly Ile
            515                 520                 525

Pro Ser Ala Pro Gln Pro Pro Glu Pro Ala Ala Leu Gln Pro Glu
            530                 535                 540

Pro Glu Ser Trp Glu Gln Ile Leu Arg Gln Ser Val Leu Gln His Arg
545                 550                 555                 560

Ala Ala Pro Ala Pro Gly Pro Gly Pro Gly Ser Gly Tyr Arg Glu Phe
                565                 570                 575

Thr Cys Ala Val Lys Gln Gly Ser Ala Pro Asp Ala Gly Pro Gly
            580                 585                 590

Phe Gly Pro Ser Gly Glu Ala Gly Tyr Lys Ala Phe Cys Ser Leu Leu
            595                 600                 605

Pro Gly Gly Ala Thr Cys Pro Gly Thr Ser Gly Gly Glu Ala Gly Ser
            610                 615                 620

Gly Glu Gly Gly Tyr Lys Pro Phe Gln Ser Leu Thr Pro Gly Cys Pro
625                 630                 635                 640

Gly Ala Pro Thr Pro Val Pro Val Pro Leu Phe Thr Phe Gly Leu Asp
                645                 650                 655
```

```
Thr Glu Pro Pro Gly Ser Pro Gln Asp Ser Leu Gly Ala Gly Ser Ser
                660                 665                 670

Pro Glu His Leu Gly Val Glu Pro Ala Gly Lys Glu Glu Asp Ser Arg
            675                 680                 685

Lys Thr Leu Leu Ala Pro Glu Gln Ala Thr Asp Pro Leu Arg Asp Asp
        690                 695                 700

Leu Ala Ser Ser Ile Val Tyr Ser Ala Leu Thr Cys His Leu Cys Gly
705                 710                 715                 720

His Leu Lys Gln Trp His Asp Gln Glu Arg Gly Lys Ala His Ile
                725                 730                 735

Val Pro Ser Pro Cys Gly Cys Cys Gly Asp Arg Ser Ser Leu
            740                 745                 750

Leu Leu Ser Pro Leu Arg Ala Pro Asn Val Leu Pro Gly Gly Val Leu
        755                 760                 765

Leu Glu Ala Ser Leu Ser Pro Ala Ser Leu Val Pro Ser Gly Val Ser
        770                 775                 780

Lys Glu Gly Lys Ser Ser Pro Phe Ser Gln Pro Ala Ser Ser Ser Ala
785                 790                 795                 800

Gln Ser Ser Ser Gln Thr Pro Lys Lys Leu Ala Val Leu Ser Thr Glu
                805                 810                 815

Pro Thr Cys Met Ser Ala Ser
                820
```

<210> SEQ ID NO 3
<211> LENGTH: 2394
<212> TYPE: DNA
<213> ORGANISM: Canis familiaris

<400> SEQUENCE: 3

```
gtgaaggtgc tgcacgagcc cagctgcttc agcgactaca tcagcaccag cgtgtgccag      60
tggaagatgg accaccccac caactgcagc gccgagctga gactgagcta ccagctggac     120
ttcatgggca gcgagaacca cacctgcgtg cccgagaaca gagaggacag cgtgtgcgtg     180
tgcagcatgc ccatcgacga cgccgtggag gccgacgtgt accagctgga cctgtgggcc     240
ggccagcagc tgctgtggag cggcagcttc agcccagca agcacgtgaa gcccagaacc     300
cccggcaacc tgaccgtgca ccccaacatc agccacacct ggctgctgat gtggaccaac     360
ccctacccca ccgagaacca cctgcacagc gagctgacct acatggtgaa cgtgagcaac     420
gacaacgacc ccgaggactt caaggtgtac aacgtgacct acatgggccc caccctgaga     480
ctggccgcca gcccctgaa gagcggcgcc agctacagcg ccagagtgag agcctgggcc     540
cagacctaca cagcacctg gagcgactgg agccccagca ccacctggct gaactactac     600
gagccctggg agcagcacct gccctgggc gtgagcatca gctgcctggt gatcctggcc     660
atctgcctga gctgctactt cagcatcatc aagatcaaga agggctggtg gaccagatc     720 cccaaccccg cccacagccc cctggtggcc atcgtgatcc aggacagcca ggtgagcctg     780
tggggcaaga aagcagagg ccaggagccc gccaagtgcc cccactggaa gacctgcctg     840
accaagctgc tgccctgcct gctggagcac ggcctgggca gagaggagga gagcccaag     900 accgccaaga acggcccct gcagggcccc ggcaagcccg cctggtgccc cgtggaggtg     960
agcaagacca tcctgtggcc cgagagcatc agcgtggtgc agtgcgtgga gctgagcgag    1020
gcccccgtgg acaacgagga ggaggaggag gtggaggagg acaagagaag cctgtgcccc    1080
agcctggagg gcagcggcgg cagcttccag gagggcagag agggcatcgt ggccagactg    1140
```

```
accgagagcc tgttcctgga cctgctgggc ggcgagaacg gcggcttctg ccccagggc    1200 ctggaggaga gctgcctgcc ccccccagc ggcagcgtgg gcgcccagat gccctgggcc    1260
cagttcccca gagccggccc cagagccgcc cccgagggcc ccgagcagcc cagaagaccc    1320
gagagcgccc tgcaggccag ccccacccag agcgccggca gcagcgcctt ccccgagccc    1380 cccccgtgg tgaccgacaa ccccgcctac agaagcttcg gcagcttcct gggccagagc    1440
agcgaccccg cgacggcga cagcgacccc gagctggccg acagaccggg cgaggccgac    1500
cccggcatcc ccagcgcccc ccagccccc gagccccccg ccgccctgca gcccgagccc    1560
gagagctggg agcagatcct gagacagagc gtgctgcagc acagagccgc ccccgccccc    1620
ggccccggcc ccggcagcgg ctacagagag ttcacctgcg ccgtgaagca gggcagcgcc    1680
cccgacgccg gcggcccgg cttcggcccc agcggcgagg ccggctacaa ggccttctgc    1740
agcctgctgc ccggcggcgc cacctgcccc ggcaccagcg gcggcgaggc cggcagcggc    1800
gagggcggct acaagccctt ccagagcctg accccggct gccccggcgc cccacccc    1860 gtgcccgtgc ccctgttcac cttcggcctg acaccgagc ccccggcag cccccaggac     1920 agcctgggcg ccggcagcag ccccgagcac ctgggcgtgg agcccgccgg caaggaggag    1980
gacagcagaa agaccctgct ggccccgag caggccaccg acccctgag agacgacctg     2040 gccagcagca tcgtgtacag cgccctgacc tgccacctgt gcggccacct gaagcagtgg    2100
cacgaccagg aggagagagg caaggccac atcgtgccca gccctgctg cggctgctgc    2160 tgcggcgaca gaagcagcct gctgctgagc cccctgagag ccccaacgt gctgcccggc    2220 ggcgtgctgc tggaggccag cctgagcccc gccagcctgg tgcccagcgg cgtgagcaag    2280
gagggcaaga gcagcccctt cagccagccc gccagcagca gcgcccagag cagcagccag    2340 accccaaga gctggccgt gctgagcacc gagcccacct gcatgagcgc cagc           2394

<210> SEQ ID NO 4
<211> LENGTH: 798
<212> TYPE: PRT
<213> ORGANISM: Canis familiaris

<400> SEQUENCE: 4

Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125

His Ser Glu Leu Thr Tyr Met Val Asn Val Ser Asn Asp Asn Asp Pro
    130                 135                 140

Glu Asp Phe Lys Val Tyr Asn Val Thr Tyr Met Gly Pro Thr Leu Arg
145                 150                 155                 160
```

```
Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Pro
        195                 200                 205

Leu Gly Val Ser Ile Ser Cys Leu Val Ile Leu Ala Ile Cys Leu Ser
    210                 215                 220

Cys Tyr Phe Ser Ile Ile Lys Ile Lys Lys Gly Trp Trp Asp Gln Ile
225                 230                 235                 240

Pro Asn Pro Ala His Ser Pro Leu Val Ala Ile Val Ile Gln Asp Ser
                245                 250                 255

Gln Val Ser Leu Trp Gly Lys Arg Ser Arg Gly Gln Glu Pro Ala Lys
            260                 265                 270

Cys Pro His Trp Lys Thr Cys Leu Thr Lys Leu Leu Pro Cys Leu Leu
        275                 280                 285

Glu His Gly Leu Gly Arg Glu Glu Ser Pro Lys Thr Ala Lys Asn
    290                 295                 300

Gly Pro Leu Gln Gly Pro Gly Lys Pro Ala Trp Cys Pro Val Glu Val
305                 310                 315                 320

Ser Lys Thr Ile Leu Trp Pro Glu Ser Ile Ser Val Val Gln Cys Val
                325                 330                 335

Glu Leu Ser Glu Ala Pro Val Asp Asn Glu Glu Glu Glu Val Glu
            340                 345                 350

Glu Asp Lys Arg Ser Leu Cys Pro Ser Leu Glu Gly Ser Gly Ser
        355                 360                 365

Phe Gln Glu Gly Arg Glu Gly Ile Val Ala Arg Leu Thr Glu Ser Leu
    370                 375                 380

Phe Leu Asp Leu Leu Gly Gly Glu Asn Gly Gly Phe Cys Pro Gln Gly
385                 390                 395                 400

Leu Glu Glu Ser Cys Leu Pro Pro Ser Gly Ser Val Gly Ala Gln
                405                 410                 415

Met Pro Trp Ala Gln Phe Pro Arg Ala Gly Pro Arg Ala Ala Pro Glu
            420                 425                 430

Gly Pro Glu Gln Pro Arg Arg Pro Glu Ser Ala Leu Gln Ala Ser Pro
        435                 440                 445

Thr Gln Ser Ala Gly Ser Ser Ala Phe Pro Glu Pro Pro Val Val
    450                 455                 460

Thr Asp Asn Pro Ala Tyr Arg Ser Phe Gly Ser Phe Leu Gly Gln Ser
465                 470                 475                 480

Ser Asp Pro Gly Asp Gly Asp Ser Asp Pro Glu Leu Ala Asp Arg Pro
                485                 490                 495

Gly Glu Ala Asp Pro Gly Ile Pro Ser Ala Pro Gln Pro Pro Glu Pro
            500                 505                 510

Pro Ala Ala Leu Gln Pro Glu Pro Glu Ser Trp Glu Gln Ile Leu Arg
        515                 520                 525

Gln Ser Val Leu Gln His Arg Ala Ala Pro Ala Pro Gly Pro Gly Pro
    530                 535                 540

Gly Ser Gly Tyr Arg Glu Phe Thr Cys Ala Val Lys Gln Gly Ser Ala
545                 550                 555                 560

Pro Asp Ala Gly Gly Pro Gly Phe Gly Pro Ser Gly Glu Ala Gly Tyr
                565                 570                 575
```

```
Lys Ala Phe Cys Ser Leu Leu Pro Gly Gly Ala Thr Cys Pro Gly Thr
                580                 585                 590

Ser Gly Gly Glu Ala Gly Ser Gly Glu Gly Gly Tyr Lys Pro Phe Gln
            595                 600                 605

Ser Leu Thr Pro Gly Cys Pro Gly Ala Pro Thr Pro Val Pro Val Pro
        610                 615                 620

Leu Phe Thr Phe Gly Leu Asp Thr Glu Pro Pro Gly Ser Pro Gln Asp
625                 630                 635                 640

Ser Leu Gly Ala Gly Ser Ser Pro Glu His Leu Gly Val Glu Pro Ala
                645                 650                 655

Gly Lys Glu Glu Asp Ser Arg Lys Thr Leu Leu Ala Pro Glu Gln Ala
            660                 665                 670

Thr Asp Pro Leu Arg Asp Asp Leu Ala Ser Ser Ile Val Tyr Ser Ala
        675                 680                 685

Leu Thr Cys His Leu Cys Gly His Leu Lys Gln Trp His Asp Gln Glu
690                 695                 700

Glu Arg Gly Lys Ala His Ile Val Pro Ser Pro Cys Cys Gly Cys Cys
705                 710                 715                 720

Cys Gly Asp Arg Ser Ser Leu Leu Ser Pro Leu Arg Ala Pro Asn
                725                 730                 735

Val Leu Pro Gly Gly Val Leu Leu Glu Ala Ser Leu Ser Pro Ala Ser
            740                 745                 750

Leu Val Pro Ser Gly Val Ser Lys Glu Gly Lys Ser Ser Pro Phe Ser
        755                 760                 765

Gln Pro Ala Ser Ser Ser Ala Gln Ser Ser Ser Gln Thr Pro Lys Lys
770                 775                 780

Leu Ala Val Leu Ser Thr Glu Pro Thr Cys Met Ser Ala Ser
785                 790                 795

<210> SEQ ID NO 5
<211> LENGTH: 624
<212> TYPE: DNA
<213> ORGANISM: Canis familiaris

<400> SEQUENCE: 5
gtgaaggtgc tgcacgagcc cagctgcttc agcgactaca tcagcaccag cgtgtgccag      60
tggaagatgg accaccccac caactgcagc gccgagctga gactgagcta ccagctggac     120
ttcatgggca gcgagaacca cacctgcgtg cccgagaaca gagaggacag cgtgtgcgtg     180
tgcagcatgc ccatcgacga cgccgtggag gccgacgtgt accagctgga cctgtgggcc     240
ggccagcagc tgctgtggag cggcagcttc agcccagca agcacgtgaa gcccagaacc     300
cccggcaacc tgaccgtgca ccccaacatc agccacacct ggctgctgat gtggaccaac     360
ccctacccca ccgagaacca cctgcacagc gagctgacct acatggtgaa cgtgagcaac     420
gacaacgacc ccgaggactt caaggtgtac aacgtgacct acatgggccc caccctgaga     480
ctggccgcca gcaccctgaa gagcggcgcc agctacagcg ccagagtgag agcctgggcc     540
cagacctaca acagcacctg gagcgactgg agcccagca ccacctggct gaactactac     600
gagccctggg agcagcacct gccc                                            624

<210> SEQ ID NO 6
<211> LENGTH: 208
<212> TYPE: PRT
<213> ORGANISM: Canis familiaris
```

<400> SEQUENCE: 6

Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125

His Ser Glu Leu Thr Tyr Met Val Asn Val Ser Asn Asp Asn Asp Pro
130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Pro
        195                 200                 205

<210> SEQ ID NO 7
<211> LENGTH: 648
<212> TYPE: DNA
<213> ORGANISM: Artificial Sequence
<220> FEATURE:
<223> OTHER INFORMATION: Canis familiaris with a HIS Tag

<400> SEQUENCE: 7
gtgaaggtgc tgcacgagcc cagctgcttc agcgactaca tcagcaccag cgtgtgccag    60
tggaagatgg accaccccac caactgcagc gccgagctga ctgagcta ccagctggac    120
ttcatgggca gcgagaacca cacctgcgtg cccgagaaca gagaggacag cgtgtgcgtg    180
tgcagcatgc ccatcgacga cgccgtggag gccgacgtgt accagctgga cctgtgggcc    240
ggccagcagc tgctgtggag cggcagcttc cagcccagca agcacgtgaa gcccagaacc    300
cccggcaacc tgaccgtgca ccccaacatc agccacacct ggctgctgat gtggaccaac    360
ccctacccca ccgagaacca cctgcacagc gagctgacct acatggtgaa cgtgagcaac    420
gacaacgacc ccgaggactt caaggtgtac aacgtgacct acatgggccc caccctgaga    480
ctggccgcca gcaccctgaa gagcggcgcc agctacagcg ccagagtgag agcctgggcc    540
cagacctaca acagcacctg gagcgactgg agcccagca ccacctggct gaactactac    600
gagccctggg agcagcacct gccccaccac caccaccac accaccac    648

<210> SEQ ID NO 8
<211> LENGTH: 216
<212> TYPE: PRT
<213> ORGANISM: Artificial Sequence
<220> FEATURE:
<223> OTHER INFORMATION: canis familiaris with a HIS tag

<400> SEQUENCE: 8

```
Val Lys Val Leu His Glu Pro Ser Cys Phe Ser Asp Tyr Ile Ser Thr
1               5                   10                  15
Ser Val Cys Gln Trp Lys Met Asp His Pro Thr Asn Cys Ser Ala Glu
            20                  25                  30
Leu Arg Leu Ser Tyr Gln Leu Asp Phe Met Gly Ser Glu Asn His Thr
        35                  40                  45
Cys Val Pro Glu Asn Arg Glu Asp Ser Val Cys Val Cys Ser Met Pro
    50                  55                  60
Ile Asp Asp Ala Val Glu Ala Asp Val Tyr Gln Leu Asp Leu Trp Ala
65                  70                  75                  80
Gly Gln Gln Leu Leu Trp Ser Gly Ser Phe Gln Pro Ser Lys His Val
                85                  90                  95
Lys Pro Arg Thr Pro Gly Asn Leu Thr Val His Pro Asn Ile Ser His
            100                 105                 110
Thr Trp Leu Leu Met Trp Thr Asn Pro Tyr Pro Thr Glu Asn His Leu
        115                 120                 125
His Ser Glu Leu Thr Tyr Met Val Asn Val Ser Asn Asp Asn Asp Pro
    130                 135                 140
Glu Asp Phe Lys Val Tyr Asn Val Thr Tyr Met Gly Pro Thr Leu Arg
145                 150                 155                 160
Leu Ala Ala Ser Thr Leu Lys Ser Gly Ala Ser Tyr Ser Ala Arg Val
                165                 170                 175
Arg Ala Trp Ala Gln Thr Tyr Asn Ser Thr Trp Ser Asp Trp Ser Pro
            180                 185                 190
Ser Thr Thr Trp Leu Asn Tyr Tyr Glu Pro Trp Glu Gln His Leu Pro
        195                 200                 205
His His His His His His His His
    210                 215
```

<210> SEQ ID NO 9
<211> LENGTH: 1317
<212> TYPE: DNA
<213> ORGANISM: Artificial Sequence
<220> FEATURE:
<223> OTHER INFORMATION: canis familiaris and human

<400> SEQUENCE: 9

```
gtgaaggtgc tgcacgagcc cagctgcttc agcgactaca tcagcaccag cgtgtgccag      60
tggaagatgg accaccccac caactgcagc gccgagctga gactgagcta ccagctggac     120
ttcatgggca gcgagaacca cacctgcgtg cccgagaaca gagaggacag cgtgtgcgtg     180
tgcagcatgc ccatcgacga cgccgtggag gccgacgtgt accagctgga cctgtgggcc     240
ggccagcagc tgctgtggag cggcagcttc cagcccagca gcacgtgaa gcccagaacc     300
cccggcaacc tgaccgtgca ccccaacatc agccacacct ggctgctgat gtggaccaac     360
ccctacccca ccgagaacca cctgcacagc gagctgacct acatggtgaa cgtgagcaac     420
gacaacgacc ccgaggactt caaggtgtac aacgtgacct acatgggccc cacccctgaga    480
ctggccgcca gcaccctgaa gagcggcgcc agctacagcg ccagagtgag agcctgggcc     540
cagacctaca acagcacctg gagcgactgg agcccagca ccacctggct gaactactac      600
gagccctggg agcagcacct ggagcccaag agctgcgaca gacccacac ctgccccccc      660
```

```
tgccccgccc ccgagctgct gggcggcccc agcgtgttcc tgttcccccc caagcccaag    720
gacaccctga tgatcagcag aaccccgag gtgacctgcg tggtggtgga cgtgagccac    780 gaggacccg aggtgaagtt caactggtac gtggacggcg tggaggtgca caacgccaag    840
accaagccca gagaggagca gtacaacagc acctacagag tggtgagcgt gctgaccgtg    900
ctgcaccagg actggctgaa cggcaaggag tacaagtgca aggtgagcaa caaggccctg    960
cccgccccca tcgagaagac catcagcaag gccaagggcc agcccagaga gcccaggtg    1020 tacaccctgc ccccagcag agacgagctg accaagaacc aggtgagcct gacctgcctg    1080
gtgaagggct ctaccccag cgacatcgcc gtggagtggg agagcaacgg ccagcccgag    1140
aacaactaca agaccacccc ccccgtgctg gacagcgacg gcagcttctt cctgtacagc    1200
aagctgaccg tggacaagag cagatggcag caggcaacg tgttcagctg cagcgtgatg    1260
cacgaggccc tgcacaacca ctacacccag aagagcctga gcctgagccc cggcaag    1317
```

<210> SEQ ID NO 10
<211> LENGTH: 439
<212> TYPE: PRT
<213> ORGANISM: Artificial Sequence
<220> FEATURE:
<223> OTHER INFORMATION: canis familiaris and human

<400> SEQUENCE: 10

```
Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125

His Ser Glu Leu Thr Tyr Met Val Asn Val Ser Asn Asp Asn Asp Pro
    130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Glu
        195                 200                 205

Pro Lys Ser Cys Asp Lys Thr His Thr Cys Pro Cys Pro Ala Pro
    210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255
```

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
            275                 280                 285

Asn Ser Thr Tyr Arg Val Ser Val Leu Thr Val Leu His Gln Asp
        290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Asp Glu Leu Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly Lys
            435

<210> SEQ ID NO 11
<211> LENGTH: 420
<212> TYPE: DNA
<213> ORGANISM: Mus musculus

<400> SEQUENCE: 11
atggactcca ggctcaattt agttttcctt gtccttattt taaaaggtgt ccggtgtgag      60
gtgcagctgg tggagtctgg gggagactta gtgaagcctg gagggtccct gaaactctcc     120
tgtgcagcct ctggattcac tttcagtgac tttggaatgc actgggttcg tcaggctcca     180
gagaaggggc tggggtgggt tgcatacatt agtagtggca gtggtaccat ctactatgca     240
gacacagtga ggggccgatt caccatctcc agagacaatg tcaagaacac cctgttcctg     300
caaatgacca gtctgaggtc tgaggacacg gccatgtatt actgtgtaag gggggacctt     360
tactacggta gtagtttcga tgcttattgg ggccgaggga ctctggtcac tgtctctgca     420

<210> SEQ ID NO 12
<211> LENGTH: 140
<212> TYPE: PRT
<213> ORGANISM: Mus musculus

<400> SEQUENCE: 12

Met Asp Ser Arg Leu Asn Leu Val Phe Leu Val Leu Ile Leu Lys Gly
1               5                   10                  15

Val Arg Cys Glu Val Gln Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Asp Phe Gly Met His Trp Val Arg Gln Ala Pro Glu Lys Gly Leu
        50                  55                  60

```
Gly Trp Val Ala Tyr Ile Ser Ser Gly Ser Thr Ile Tyr Tyr Ala
 65                  70                  75                  80

Asp Thr Val Arg Gly Arg Phe Thr Ile Ser Arg Asp Asn Val Lys Asn
                 85                  90                  95

Thr Leu Phe Leu Gln Met Thr Ser Leu Arg Ser Glu Asp Thr Ala Met
            100                 105                 110

Tyr Tyr Cys Val Arg Gly Asp Leu Tyr Tyr Gly Ser Ser Phe Asp Ala
        115                 120                 125

Tyr Trp Gly Arg Gly Thr Leu Val Thr Val Ser Ala
130                 135                 140

<210> SEQ ID NO 13
<211> LENGTH: 384
<212> TYPE: DNA
<213> ORGANISM: Mus musculus

<400> SEQUENCE: 13
atggattttc aagtgcagat tttcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagtttca tgttctggta ccagcagaag     180
ccaggatcct cccccaaacc ctggatttat gacacatcca acctggcttc tggagtccct     240
gctcgcttca gtggcagtgg gtctgggacc tcttactctc tcacaatcag cagagtggag     300
gctgaagatg ctgccactta ttactgccag cagtggagta gtaacccact cacgttcggt     360
gctgggacca agctggagct gaaa                                            384

<210> SEQ ID NO 14
<211> LENGTH: 128
<212> TYPE: PRT
<213> ORGANISM: Mus musculus

<400> SEQUENCE: 14

Met Asp Phe Gln Val Gln Ile Phe Ser Phe Leu Leu Ile Ser Ala Ser
  1               5                  10                  15

Val Ile Met Ser Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Phe Met Phe Trp Tyr Gln Gln Lys Pro Gly Ser Ser
     50                  55                  60

Pro Lys Pro Trp Ile Tyr Asp Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

<210> SEQ ID NO 15
<211> LENGTH: 405
<212> TYPE: DNA
<213> ORGANISM: Mus musculus
```

<400> SEQUENCE: 15

```
atggaatggc cttgtatctt tctcttcctc ctgtcagtaa ctgaaggtgt ccactcccag    60
gttccgctgc agcagtctgg acctgagctg gtgaagcctg ggcctcagt gaagatttcc    120
tgcaaggctt ctggctacgc attcagtagc tcctggatga actgggtgaa gcagaggcct    180
ggaaagggtc ttgagtggat tggacggatt tatcctggag atggagatac taagtacaat    240
gggaagttca aggcaaggc cacactgact gcagacaaat cctccagcac agcctacatg    300
caactcagca gcctgacatc ggaggactct gcggtttact tctgtgcaag agatgattac    360
gacgaggctt cctggggcca aggactctg gtcactgtct ctgca              405
```

<210> SEQ ID NO 16
<211> LENGTH: 135
<212> TYPE: PRT
<213> ORGANISM: Mus musculus

<400> SEQUENCE: 16

```
Met Glu Trp Pro Cys Ile Phe Leu Phe Leu Leu Ser Val Thr Glu Gly
1               5                   10                  15
Val His Ser Gln Val Pro Leu Gln Gln Ser Gly Pro Glu Leu Val Lys
            20                  25                  30
Pro Gly Ala Ser Val Lys Ile Ser Cys Lys Ala Ser Gly Tyr Ala Phe
        35                  40                  45
Ser Ser Ser Trp Met Asn Trp Val Lys Gln Arg Pro Gly Lys Gly Leu
    50                  55                  60
Glu Trp Ile Gly Arg Ile Tyr Pro Gly Asp Gly Asp Thr Lys Tyr Asn
65                  70                  75                  80
Gly Lys Phe Lys Gly Lys Ala Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Phe Cys Ala Arg Asp Asp Tyr Asp Glu Ala Ser Trp Gly Gln Gly
        115                 120                 125
Thr Leu Val Thr Val Ser Ala
    130                 135
```

<210> SEQ ID NO 17
<211> LENGTH: 393
<212> TYPE: DNA
<213> ORGANISM: Mus musculus

<400> SEQUENCE: 17

```
atgggcatca agatggagtt tcagacccag gtctttgtat tcgtgttgct ctggttgtct    60
ggtgttgatg gagacattgt gatgacccag tctcaaaaat tcatgtccac atcagtagga    120
gacagggtca gcatcacctg caaggccagt cagaatgttc gttctgctgt agcctggtat    180
caacagaaac cagggcagtc tcctaaatca ctgatttact tggcatccaa ccggcacact    240
ggagtccctg atcgcttcac aggcagtgga tctgggacag atttcactct caccattagc    300
aatgtgcaat ctgaagacct ggcagattat ttctgtctgc aacattggaa ttatccattc    360
acgttcggct cggggacaaa gttggaaata aaa              393
```

<210> SEQ ID NO 18
<211> LENGTH: 131
<212> TYPE: PRT
<213> ORGANISM: Mus musculus

<400> SEQUENCE: 18

| Met | Gly | Ile | Lys | Met | Glu | Phe | Gln | Thr | Gln | Val | Phe | Val | Phe | Val | Leu |
|---|---|---|---|---|---|---|---|---|---|---|---|---|---|---|---|
| 1 | | | | 5 | | | | | 10 | | | | | 15 | |

| Leu | Trp | Leu | Ser | Gly | Val | Asp | Gly | Asp | Ile | Val | Met | Thr | Gln | Ser | Gln |
|---|---|---|---|---|---|---|---|---|---|---|---|---|---|---|---|
| | | | 20 | | | | | 25 | | | | | 30 | | |

| Lys | Phe | Met | Ser | Thr | Ser | Val | Gly | Asp | Arg | Val | Ser | Ile | Thr | Cys | Lys |
|---|---|---|---|---|---|---|---|---|---|---|---|---|---|---|---|
| | | 35 | | | | | 40 | | | | | 45 | | | |

| Ala | Ser | Gln | Asn | Val | Arg | Ser | Ala | Val | Ala | Trp | Tyr | Gln | Gln | Lys | Pro |
|---|---|---|---|---|---|---|---|---|---|---|---|---|---|---|---|
| | 50 | | | | | 55 | | | | | 60 | | | | |

| Gly | Gln | Ser | Pro | Lys | Ser | Leu | Ile | Tyr | Leu | Ala | Ser | Asn | Arg | His | Thr |
|---|---|---|---|---|---|---|---|---|---|---|---|---|---|---|---|
| 65 | | | | | 70 | | | | | 75 | | | | | 80 |

| Gly | Val | Pro | Asp | Arg | Phe | Thr | Gly | Ser | Gly | Ser | Gly | Thr | Asp | Phe | Thr |
|---|---|---|---|---|---|---|---|---|---|---|---|---|---|---|---|
| | | | | 85 | | | | | 90 | | | | | 95 | |

| Leu | Thr | Ile | Ser | Asn | Val | Gln | Ser | Glu | Asp | Leu | Ala | Asp | Tyr | Phe | Cys |
|---|---|---|---|---|---|---|---|---|---|---|---|---|---|---|---|
| | | | 100 | | | | | 105 | | | | | 110 | | |

| Leu | Gln | His | Trp | Asn | Tyr | Pro | Phe | Thr | Phe | Gly | Ser | Gly | Thr | Lys | Leu |
|---|---|---|---|---|---|---|---|---|---|---|---|---|---|---|---|
| | | 115 | | | | | 120 | | | | | 125 | | | |

| Glu | Ile | Lys |
|---|---|---|
| 130 | | |

<210> SEQ ID NO 19
<211> LENGTH: 429
<212> TYPE: DNA
<213> ORGANISM: Mus musculus

<400> SEQUENCE: 19

```
atgggatgga gctggatctt tctctttctc ctgtcaggaa ctgcaggtgt cctctctgag      60
gtccagctgc aacaatctgg acctgagctg gtgaagcctg ggcttcagt gaagatatcc     120
tgtaaggctt ctggatacac gttcactgac tattacatga actgggtgaa gcagagccat     180
ggaaagagcc ttgagtggat tggagacatt attcctagca atggtggtac tagctacaac     240
cagaagttca agggcaaggc cacattgact gtagacaagt cctccagcgc agcctacatg     300
gagctccgca gcctgacatc tgaggactct gcagtctatt actgtgcaag agggatcagc     360
tactatggta accgatatta ctttactatg gactattggg gtcaaggaac ctcagtcacc     420
gtctcctca                                                              429
```

<210> SEQ ID NO 20
<211> LENGTH: 143
<212> TYPE: PRT
<213> ORGANISM: Mus musculus

<400> SEQUENCE: 20

| Met | Gly | Trp | Ser | Trp | Ile | Phe | Leu | Phe | Leu | Leu | Ser | Gly | Thr | Ala | Gly |
|---|---|---|---|---|---|---|---|---|---|---|---|---|---|---|---|
| 1 | | | | 5 | | | | | 10 | | | | | 15 | |

| Val | Leu | Ser | Glu | Val | Gln | Leu | Gln | Gln | Ser | Gly | Pro | Glu | Leu | Val | Lys |
|---|---|---|---|---|---|---|---|---|---|---|---|---|---|---|---|
| | | | 20 | | | | | 25 | | | | | 30 | | |

| Pro | Gly | Ala | Ser | Val | Lys | Ile | Ser | Cys | Lys | Ala | Ser | Gly | Tyr | Thr | Phe |
|---|---|---|---|---|---|---|---|---|---|---|---|---|---|---|---|
| | | 35 | | | | | 40 | | | | | 45 | | | |

| Thr | Asp | Tyr | Tyr | Met | Asn | Trp | Val | Lys | Gln | Ser | His | Gly | Lys | Ser | Leu |
|---|---|---|---|---|---|---|---|---|---|---|---|---|---|---|---|
| | 50 | | | | | 55 | | | | | 60 | | | | |

| Glu | Trp | Ile | Gly | Asp | Ile | Ile | Pro | Ser | Asn | Gly | Gly | Thr | Ser | Tyr | Asn |
|---|---|---|---|---|---|---|---|---|---|---|---|---|---|---|---|
| 65 | | | | | 70 | | | | | 75 | | | | | 80 |

| Gln | Lys | Phe | Lys | Gly | Lys | Ala | Thr | Leu | Thr | Val | Asp | Lys | Ser | Ser | Ser |
|---|---|---|---|---|---|---|---|---|---|---|---|---|---|---|---|
| | | | | 85 | | | | | 90 | | | | | 95 | |

```
Ala Ala Tyr Met Glu Leu Arg Ser Leu Thr Ser Glu Asp Ser Ala Val
                100                 105                 110

Tyr Tyr Cys Ala Arg Gly Ile Ser Tyr Tyr Gly Asn Arg Tyr Tyr Phe
            115                 120                 125

Thr Met Asp Tyr Trp Gly Gln Gly Thr Ser Val Thr Val Ser Ser
130                 135                 140
```

<210> SEQ ID NO 21
<211> LENGTH: 396
<212> TYPE: DNA
<213> ORGANISM: Mus musculus

<400> SEQUENCE: 21

```
atgaggtgcc tagctgagtt cctggggctg cttgtgctct ggatccctgg agccattggg    60
gatattgtga tgactcaggc tgcaccctct gtacctgtca ctcctggaga gtcagtatcc   120
atctcctgca ggtctagtaa gagtctcctg catagtaatg caacacttta cttgttttgg   180
ttcgtgcaga ggccaggcca gtctcctcag ctcctgatat atcggatgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacatct agaatatcca   360
ttcacgttcg gctcggggac aaagttggac ataaaa                             396
```

<210> SEQ ID NO 22
<211> LENGTH: 132
<212> TYPE: PRT
<213> ORGANISM: Mus musculus

<400> SEQUENCE: 22

```
Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Phe Trp Phe Val Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ser Gly Thr Lys
        115                 120                 125

Leu Asp Ile Lys
    130
```

<210> SEQ ID NO 23
<211> LENGTH: 417
<212> TYPE: DNA
<213> ORGANISM: Mus musculus

<400> SEQUENCE: 23

```
atggaatgga gctggatctt tctcttcctc ctgtcagtaa ctgcaggtgt ccaatcccag    60
gttcaactgc agcagtctgg ggctgagctg gtgaggcctg ggcttcagt gaagctgtcc   120
```

-continued

```
tgcaaggctt cgggctacac atttactgac tatgaaatgc actgtgtgaa gcagacacct    180
gtgcacggcc tggaatggat tggagctatt gatcctgaaa cttgtggtac tgcctacaat    240
cagaagttca agggcaaggc cacactgact gcagacaaat cctccagcac agcctacatg    300
gagctccgca gcctgacatc tgaggactct gccgtctatt actgtacaag atcgaaactg    360
ggacgagggt ggtacttcga tgtctgggc acagggacca cggtcaccgt ctcctca        417
```

<210> SEQ ID NO 24
<211> LENGTH: 139
<212> TYPE: PRT
<213> ORGANISM: Mus musculus

<400> SEQUENCE: 24

```
Met Glu Trp Ser Trp Ile Phe Leu Phe Leu Leu Ser Val Thr Ala Gly
1               5                   10                  15

Val Gln Ser Gln Val Gln Leu Gln Gln Ser Gly Ala Glu Leu Val Arg
            20                  25                  30

Pro Gly Ala Ser Val Lys Leu Ser Cys Lys Ala Ser Gly Tyr Thr Phe
        35                  40                  45

Thr Asp Tyr Glu Met His Cys Val Lys Gln Thr Pro Val His Gly Leu
    50                  55                  60

Glu Trp Ile Gly Ala Ile Asp Pro Glu Thr Cys Gly Thr Ala Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Arg Ser Lys Leu Gly Arg Gly Trp Tyr Phe Asp Val
        115                 120                 125

Trp Gly Thr Gly Thr Thr Val Thr Val Ser Ser
    130                 135
```

<210> SEQ ID NO 25
<211> LENGTH: 399
<212> TYPE: DNA
<213> ORGANISM: Mus musculus

<400> SEQUENCE: 25

```
atggaatcac agacccaggt cctcatgttt cttctgctct ggtatctggt gcctgtgca     60 gacattgtga tgacacagtc tccatcctcc ctggctatgt cagtaggaca gaaggtcact    120
atgagctgca gtccagtca gagccttta aatagtagca atcaaaagaa ctatttggcc     180
tggtaccagc agaaaccagg acagtctcct aaacttctgg tatactttgc atccactagg    240
gaatctgggg tccctgatcg cttcataggc agtggatctg ggacagattt cactcttacc    300
atcagcagtg tgcaggctga agacctggca gattacttct gtcagcaaca ttatagcact    360
ccgtacacgt tcggaggggg gaccaagctg gaaataaaa                           399
```

<210> SEQ ID NO 26
<211> LENGTH: 133
<212> TYPE: PRT
<213> ORGANISM: Mus musculus

<400> SEQUENCE: 26

```
Met Glu Ser Gln Thr Gln Val Leu Met Phe Leu Leu Leu Trp Val Ser
1               5                   10                  15
```

Gly Ala Cys Ala Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Tyr Thr Phe Gly Gly Gly Thr
        115                 120                 125

Lys Leu Glu Ile Lys
    130

<210> SEQ ID NO 27
<211> LENGTH: 426
<212> TYPE: DNA
<213> ORGANISM: Mus musculus

<400> SEQUENCE: 27
atggctgtcc tggcactgct cctctgcctg gtgacattcc caaactgtgt cctgtcccag      60
gtgcacctga aggagtcagg acctggcctg gtggcgccct cacagagcct gtccatcaca     120
tgcactgtct cagggttctc tttaaccagc tatggtgtaa ctgggttcg ccagcctcca     180 ggagagggtc tggagtggct gggagtaata tggggtgacg ggagcacata ttttcattca     240
gctctcatat ccagactgag catcagcaag gatgactcca agagccaagt tttcttaaaa     300
ttgaacagtc tacaaactga tgacacagcc acgtactact gtgccaaaca agggacgatc     360
tatgatggtt actacaacta tgctatggac tactggggtc aaggaacctc agtcaccgtc     420
tcctca                                                               426

<210> SEQ ID NO 28
<211> LENGTH: 142
<212> TYPE: PRT
<213> ORGANISM: Mus musculus

<400> SEQUENCE: 28

Met Ala Val Leu Ala Leu Leu Cys Leu Val Thr Phe Pro Asn Cys
1               5                   10                  15

Val Leu Ser Gln Val His Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Gly Val Ser Trp Val Arg Gln Pro Pro Gly Glu Gly Leu
50                  55                  60

Glu Trp Leu Gly Val Ile Trp Gly Asp Gly Ser Thr Tyr Phe His Ser
65                  70                  75                  80

Ala Leu Ile Ser Arg Leu Ser Ile Ser Lys Asp Asp Ser Lys Ser Gln
                85                  90                  95

Val Phe Leu Lys Leu Asn Ser Leu Gln Thr Asp Asp Thr Ala Thr Tyr
            100                 105                 110

Tyr Cys Ala Lys Gln Gly Thr Ile Tyr Asp Gly Tyr Tyr Asn Tyr Ala
            115                 120                 125

Met Asp Tyr Trp Gly Gln Gly Thr Ser Val Thr Val Ser Ser
            130                 135                 140

<210> SEQ ID NO 29
<211> LENGTH: 399
<212> TYPE: DNA
<213> ORGANISM: Mus musculus

<400> SEQUENCE: 29
atggattcac aggcccaggt tcttatgtta ctgctgctat gggtatctgg tacctgtggg    60
gacattgtga tgtcacagtc tccatcctcc ctaactgtgt cagttggaga aaggttact    120 atgagctgca gtccagtca gaacctttta tatggtggca atcaaaagaa ctacttggcc    180
tggtaccagc agaaaccagg gcagtctcct aaactgctga tttactgggc atccactagg    240
gaatctgggg tccctgatcg cttcacaggc agtggatctg gacagatttt cactctcacc    300
atcagcagtg tgagggctga agacctggca gtttattact gtcagcaata ttatgactat    360
ccgtacacgt tcggagggg gaccaagctg gaaataaaa                           399

<210> SEQ ID NO 30
<211> LENGTH: 133
<212> TYPE: PRT
<213> ORGANISM: Mus musculus

<400> SEQUENCE: 30

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Thr
            20                  25                  30

Val Ser Val Gly Glu Lys Val Thr Met Ser Cys Lys Ser Ser Gln Asn
        35                  40                  45

Leu Leu Tyr Gly Gly Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Arg Ala Glu Asp Leu Ala Val Tyr
            100                 105                 110

Tyr Cys Gln Gln Tyr Tyr Asp Tyr Pro Tyr Thr Phe Gly Gly Gly Thr
        115                 120                 125

Lys Leu Glu Ile Lys
    130

<210> SEQ ID NO 31
<211> LENGTH: 402
<212> TYPE: DNA
<213> ORGANISM: Mus musculus

<400> SEQUENCE: 31
atgggatgga gctggatctt tctcttcctc ctgtcaggaa ctgcaggtgt ccactcccag    60
gttcagctgc agcagtctgg acctgagctg gtgaagcctg ggcttcagt gaagttgtcc    120 tgcaaggctt ctggctacac cttcacaacc tacgatatac actgggtgaa gcagaggcct    180
gggcagggcc ttgagtggat tggatggatt tatcctagag atggtcgtac tacttacaat    240

```
gagaagttca aggccaaggc cacattgact gtagacacat cctccaccac agcgtacatg    300
gagctccaca gcctgacatc tgaggactct gcggtctatt tctgtgcgag aagtagcccc    360
tttggctact ggggccaagg caccactctc acagtctcct ca                       402
```

<210> SEQ ID NO 32
<211> LENGTH: 134
<212> TYPE: PRT
<213> ORGANISM: Mus musculus

<400> SEQUENCE: 32

```
Met Gly Trp Ser Trp Ile Phe Leu Phe Leu Leu Ser Gly Thr Ala Gly
1               5                   10                  15

Val His Ser Gln Val Gln Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Thr Tyr Asp Ile His Trp Val Lys Gln Arg Pro Gly Gln Gly Leu
    50                  55                  60

Glu Trp Ile Gly Trp Ile Tyr Pro Arg Asp Gly Arg Thr Thr Tyr Asn
65                  70                  75                  80

Glu Lys Phe Lys Ala Lys Ala Thr Leu Thr Val Asp Thr Ser Ser Thr
                85                  90                  95

Thr Ala Tyr Met Glu Leu His Ser Leu Thr Ser Glu Asp Ser Ala Val
            100                 105                 110

Tyr Phe Cys Ala Arg Ser Ser Pro Phe Gly Tyr Trp Gly Gln Gly Thr
        115                 120                 125

Thr Leu Thr Val Ser Ser
    130
```

<210> SEQ ID NO 33
<211> LENGTH: 381
<212> TYPE: DNA
<213> ORGANISM: Mus musculus

<400> SEQUENCE: 33

```
atgaagtttc cttctcaact tctgctcttc ctgctgttca gaatcacagg cataatatgt    60
gacatccaga tgacacaatc ttcatcctac ttgtctgtat ctctaggagg cagagtcacc    120
attacttgca aggcaagtga ccacattaat aattggttag cctggtatca gcagaaacca    180
ggaaatgctc ctaggctctt aatatctggt gcaaccagtt tggaaactgg ggttccttca    240
agattcagtg gcagtggatc tggaaaggat tacactctca gcattaccag tcttcagact    300
gaagatgctg ctacttatca ctgtcaccag tattggagta ttccgtacac gttcggaggg    360
gggaccaagg tggaaataaa a                                               381
```

<210> SEQ ID NO 34
<211> LENGTH: 127
<212> TYPE: PRT
<213> ORGANISM: Mus musculus

<400> SEQUENCE: 34

```
Met Lys Phe Pro Ser Gln Leu Leu Leu Phe Leu Leu Phe Arg Ile Thr
1               5                   10                  15

Gly Ile Ile Cys Asp Ile Gln Met Thr Gln Ser Ser Ser Tyr Leu Ser
            20                  25                  30
```

Val Ser Leu Gly Gly Arg Val Thr Ile Thr Cys Lys Ala Ser Asp His
            35                  40                  45

Ile Asn Asn Trp Leu Ala Trp Tyr Gln Gln Lys Pro Gly Asn Ala Pro
    50                  55                  60

Arg Leu Leu Ile Ser Gly Ala Thr Ser Leu Glu Thr Gly Val Pro Ser
65                  70                  75                  80

Arg Phe Ser Gly Ser Gly Ser Gly Lys Asp Tyr Thr Leu Ser Ile Thr
                85                  90                  95

Ser Leu Gln Thr Glu Asp Ala Ala Thr Tyr His Cys His Gln Tyr Trp
            100                 105                 110

Ser Ile Pro Tyr Thr Phe Gly Gly Gly Thr Lys Val Glu Ile Lys
        115                 120                 125

<210> SEQ ID NO 35
<211> LENGTH: 396
<212> TYPE: DNA
<213> ORGANISM: Mus musculus

<400> SEQUENCE: 35
atggaatgga gctgggtctt tctcttcctc ctgtcagtaa ttgcaggtgt ccaatcccag      60
gttcaactgc agcagtctgg ggctgagctg gtggggcctg ggcttcagt gacgctgtcc     120 tgcaaggctt cgggctacac atttactgac tatgaaatgc actgggtgaa gcagacacct     180
gtgcatggcc tggaatgcat tggagctatt gatcctgaaa ctggtggtac tgcctacaat     240
cagaagttca gggcaaggc catactgact gcagacaaat cctctagcac agcctacatg     300
gagctccgca gcctgacatc tgaggactct gccgtctatt actgtctaac tgggtttgac     360
tactggggcc aaggcaccac tctcacagtc tcctca                              396

<210> SEQ ID NO 36
<211> LENGTH: 132
<212> TYPE: PRT
<213> ORGANISM: Mus musculus

<400> SEQUENCE: 36

Met Glu Trp Ser Trp Val Phe Leu Phe Leu Leu Ser Val Ile Ala Gly
1               5                   10                  15

Val Gln Ser Gln Val Gln Leu Gln Gln Ser Gly Ala Glu Leu Val Gly
            20                  25                  30

Pro Gly Ala Ser Val Thr Leu Ser Cys Lys Ala Ser Gly Tyr Thr Phe
        35                  40                  45

Thr Asp Tyr Glu Met His Trp Val Lys Gln Thr Pro Val His Gly Leu
    50                  55                  60

Glu Cys Ile Gly Ala Ile Asp Pro Glu Thr Gly Gly Thr Ala Tyr Asn
65                  70                  75                  80

Gln Lys Phe Lys Gly Lys Ala Ile Leu Thr Ala Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Leu Thr Gly Phe Asp Tyr Trp Gly Gln Gly Thr Thr Leu
        115                 120                 125

Thr Val Ser Ser
    130

<210> SEQ ID NO 37
<211> LENGTH: 390

```
<212> TYPE: DNA
<213> ORGANISM: Mus musculus

<400> SEQUENCE: 37
atggattttc aggtgcagat tttcagcttc ctgctaatca gtgtctcagt cataatgtcc      60
agaggacaaa ttgttctcac ccagtctcca gcaatcatgt ctgcatctcc tggggagaag     120
gtcaccttga cctgcagtgc cagctcaagt gtgaattcca gctacttgta ctggtaccag     180
cagaagccag atcctcccc caaactctgg atttatagca catccaacct ggcttctgga      240
gtccctgctc gcttcagtgg cagtgggtct ggaacctctt actctctcac aatcagcagc     300
atggaggctg aagatgctgc ctcttatttc tgccatcagt ggagtagtta cccgtacacg     360
ttcggagggg ggaccaagct ggaaataaaa                                      390

<210> SEQ ID NO 38
<211> LENGTH: 130
<212> TYPE: PRT
<213> ORGANISM: Mus musculus

<400> SEQUENCE: 38
```

Met Asp Phe Gln Val Gln Ile Phe Ser Phe Leu Leu Ile Ser Val Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Leu Thr Cys Ser Ala Ser
        35                  40                  45

Ser Ser Val Asn Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Ser Tyr Phe Cys His
            100                 105                 110

Gln Trp Ser Ser Tyr Pro Tyr Thr Phe Gly Gly Gly Thr Lys Leu Glu
        115                 120                 125

Ile Lys
    130

```
<210> SEQ ID NO 39
<211> LENGTH: 417
<212> TYPE: DNA
<213> ORGANISM: Mus musculus

<400> SEQUENCE: 39
atgatggtgt taagtcttct gtacctgttg acagcccttc gggtatcct gtcagaggtg       60 cagcttcagg agtcaggacc tggcctggca aaaccttctc agactctgtc cctcacctgt     120
tctgtcactg gctactccat caccagtgat tactggaact ggatccggaa attcccaggg     180
aataaacttg aatacatggg gtacataaac tacagtggta cacttacta caatccatct      240 ctcaaaagtc gaatctccat aactcgagac acatccaaga accagtatta cctgcaattg     300
aattctgtga ctactgagga cacagccacg tattactgtg caagatatgg gggattacga     360
cagggttcct ggcacttcga tgtctggggc cagggacca cggtcaccgt ctcctca        417

<210> SEQ ID NO 40
<211> LENGTH: 139
```

```
<212> TYPE: PRT
<213> ORGANISM: Mus musculus

<400> SEQUENCE: 40

Met Met Val Leu Ser Leu Leu Tyr Leu Leu Thr Ala Leu Pro Gly Ile
1               5                   10                  15

Leu Ser Glu Val Gln Leu Gln Glu Ser Gly Pro Gly Leu Ala Lys Pro
                20                  25                  30

Ser Gln Thr Leu Ser Leu Thr Cys Ser Val Thr Gly Tyr Ser Ile Thr
            35                  40                  45

Ser Asp Tyr Trp Asn Trp Ile Arg Lys Phe Pro Gly Asn Lys Leu Glu
50                  55                  60

Tyr Met Gly Tyr Ile Asn Tyr Ser Gly Asn Thr Tyr Tyr Asn Pro Ser
65                  70                  75                  80

Leu Lys Ser Arg Ile Ser Ile Thr Arg Asp Thr Ser Lys Asn Gln Tyr
                85                  90                  95

Tyr Leu Gln Leu Asn Ser Val Thr Thr Glu Asp Thr Ala Thr Tyr Tyr
            100                 105                 110

Cys Ala Arg Tyr Gly Gly Leu Arg Gln Gly Ser Trp His Phe Asp Val
        115                 120                 125

Trp Gly Pro Gly Thr Thr Val Thr Val Ser Ser
        130                 135

<210> SEQ ID NO 41
<211> LENGTH: 384
<212> TYPE: DNA
<213> ORGANISM: Mus musculus

<400> SEQUENCE: 41
atggattttc aggtgcagat tttcagcttc ctgctaatca gtgcctcagt cataatgtcc      60
agaggacaaa ttgttctcac ccagtctcca gcaatcatgt ctgcatctcc aggggagaag     120
gtcaccatat cctgcagtgc cagctcaagt gtaagttaca tgtactggta ccagcagaag     180
ccaggatcct cccccaaacc ctggatttat cgcacatcca acctggcttc tggagtccct     240
gcgcgcttca gtggcagtgg gtctgggacc tcttactctc tcacaatcag cagcatggag     300
gctgaagatg ctgccactta ttactgccag cagtatcata gttacccagc gacgttcggt     360
ggaggcacca agctggaaat caaa                                            384

<210> SEQ ID NO 42
<211> LENGTH: 128
<212> TYPE: PRT
<213> ORGANISM: Mus musculus

<400> SEQUENCE: 42

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
                20                  25                  30

Met Ser Ala Ser Pro Gly Glu Lys Val Thr Ile Ser Cys Ser Ala Ser
            35                  40                  45

Ser Ser Val Ser Tyr Met Tyr Trp Tyr Gln Gln Lys Pro Gly Ser Ser
50                  55                  60

Pro Lys Pro Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95
```

```
Ser Ser Met Glu Ala Glu Asp Ala Ala Thr Tyr Tyr Cys Gln Gln Tyr
            100                 105                 110

His Ser Tyr Pro Ala Thr Phe Gly Gly Gly Thr Lys Leu Glu Ile Lys
        115                 120                 125
```

<210> SEQ ID NO 43
<211> LENGTH: 402
<212> TYPE: DNA
<213> ORGANISM: Mus musculus

<400> SEQUENCE: 43

| | | | | | |
|---|---|---|---|---|---|
| atgggttggc | tgtggaactt | gctattcctg | atggcagctg | cccaaagtgc | ccaagcacag | 60 |
| atccagttgg | tacagtctgg | acctgagctg | aagaagcctg | gagagacagt | caagatctcc | 120 |
| tgcaaggctt | ctgggtatat | cttcacaacc | tatggaatgt | actgggtgaa | acaggctcca | 180 |
| ggaaagggtt | taaagtggat | gggctggata | aacacctact | ctggagtgcc | aacatatgtt | 240 |
| gatgacttca | aggacggttt | gccttctct | tggaaacat | ctgccagcac | tgcctatttg | 300 |
| cagatcaaca | acctcaaaaa | tgaggacacg | gctacatatt | tctgtgtagt | tgccgggtgg | 360 |
| tttgcttact | ggggccaagg | gactctggtc | actgtctctg | ca | | 402 |

<210> SEQ ID NO 44
<211> LENGTH: 134
<212> TYPE: PRT
<213> ORGANISM: Mus musculus

<400> SEQUENCE: 44

```
Met Gly Trp Leu Trp Asn Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ile Phe
        35                  40                  45

Thr Thr Tyr Gly Met Tyr Trp Val Lys Gln Ala Pro Gly Lys Gly Leu
    50                  55                  60

Lys Trp Met Gly Trp Ile Asn Thr Tyr Ser Gly Val Pro Thr Tyr Val
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val Val Ala Gly Trp Phe Ala Tyr Trp Gly Gln Gly Thr
        115                 120                 125

Leu Val Thr Val Ser Ala
    130
```

<210> SEQ ID NO 45
<211> LENGTH: 387
<212> TYPE: DNA
<213> ORGANISM: Mus musculus

<400> SEQUENCE: 45

| | | | | | |
|---|---|---|---|---|---|
| atggacatga | ggacccctgc | tcagtttctt | ggaatcttgt | tgctctggtt | tccaggtatc | 60 |
| aaatgtgaca | tcaagatgac | ccagtctcca | tcttccatgt | atgcatctct | aggagagaga | 120 |
| gtcactatca | cttgcaaggc | gagtcaggac | attaagagct | atttaagctg | gttccagcag | 180 |
| aaaccaggga | atctcctaa | gaccctgatc | tatcgtgcaa | atatattgat | agatgggtc | 240 |

```
ccatcaaggt tcagtggcag tggatctggg caagattatt ctctcaccat cagcagcctg    300
gagtatgaag atatgggaat ttattattgt ctacaatatg atgagtttcc gtacacgttc    360 ggaggggga ccaagctgga aataaaa                                          387
```

```
<210> SEQ ID NO 46
<211> LENGTH: 129
<212> TYPE: PRT
<213> ORGANISM: Mus musculus

<400> SEQUENCE: 46
```

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Lys Ser Tyr Leu Ser Trp Phe Gln Lys Pro Gly Lys
    50                  55                  60

Ser Pro Lys Thr Leu Ile Tyr Arg Ala Asn Ile Leu Ile Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Tyr Thr Phe Gly Gly Gly Thr Lys Leu Glu Ile
        115                 120                 125

Lys

```
<210> SEQ ID NO 47
<211> LENGTH: 10
<212> TYPE: PRT
<213> ORGANISM: Mus musculus

<400> SEQUENCE: 47
```

Arg Ala Ser Ser Ser Val Ser Phe Met Phe
1               5                   10

```
<210> SEQ ID NO 48
<211> LENGTH: 11
<212> TYPE: PRT
<213> ORGANISM: Mus musculus

<400> SEQUENCE: 48
```

Lys Ala Ser Gln Asn Val Arg Ser Ala Val Ala
1               5                   10

```
<210> SEQ ID NO 49
<211> LENGTH: 16
<212> TYPE: PRT
<213> ORGANISM: Mus musculus

<400> SEQUENCE: 49
```

Arg Ser Ser Lys Ser Leu Leu His Ser Asn Gly Asn Thr Tyr Leu Phe
1               5                   10                  15

```
<210> SEQ ID NO 50
<211> LENGTH: 17
<212> TYPE: PRT
<213> ORGANISM: Mus musculus
```

```
<400> SEQUENCE: 50

Lys Ser Ser Gln Ser Leu Leu Asn Ser Ser Asn Gln Lys Asn Tyr Leu
1               5                   10                  15
Ala

<210> SEQ ID NO 51
<211> LENGTH: 17
<212> TYPE: PRT
<213> ORGANISM: Mus musculus

<400> SEQUENCE: 51

Lys Ser Ser Gln Asn Leu Leu Tyr Gly Gly Asn Gln Lys Asn Tyr Leu
1               5                   10                  15
Ala

<210> SEQ ID NO 52
<211> LENGTH: 11
<212> TYPE: PRT
<213> ORGANISM: Mus musculus

<400> SEQUENCE: 52

Lys Ala Ser Asp His Ile Asn Asn Trp Leu Ala
1               5                   10

<210> SEQ ID NO 53
<211> LENGTH: 12
<212> TYPE: PRT
<213> ORGANISM: Mus musculus

<400> SEQUENCE: 53

Ser Ala Ser Ser Ser Val Asn Ser Ser Tyr Leu Tyr
1               5                   10

<210> SEQ ID NO 54
<211> LENGTH: 10
<212> TYPE: PRT
<213> ORGANISM: Mus musculus

<400> SEQUENCE: 54

Ser Ala Ser Ser Ser Val Ser Tyr Met Tyr
1               5                   10

<210> SEQ ID NO 55
<211> LENGTH: 11
<212> TYPE: PRT
<213> ORGANISM: Mus musculus

<400> SEQUENCE: 55

Lys Ala Ser Gln Asp Ile Lys Ser Tyr Leu Ser
1               5                   10

<210> SEQ ID NO 56
<211> LENGTH: 7
<212> TYPE: PRT
<213> ORGANISM: Mus musculus

<400> SEQUENCE: 56

Asp Thr Ser Asn Leu Ala Ser
1               5

<210> SEQ ID NO 57
<211> LENGTH: 7
```

```
<212> TYPE: PRT
<213> ORGANISM: Mus musculus

<400> SEQUENCE: 57

Leu Ala Ser Asn Arg His Thr
1               5

<210> SEQ ID NO 58
<211> LENGTH: 7
<212> TYPE: PRT
<213> ORGANISM: Mus musculus

<400> SEQUENCE: 58

Arg Met Ser Asn Leu Ala Ser
1               5

<210> SEQ ID NO 59
<211> LENGTH: 7
<212> TYPE: PRT
<213> ORGANISM: Mus musculus

<400> SEQUENCE: 59

Phe Ala Ser Thr Arg Glu Ser
1               5

<210> SEQ ID NO 60
<211> LENGTH: 7
<212> TYPE: PRT
<213> ORGANISM: Mus musculus

<400> SEQUENCE: 60

Trp Ala Ser Thr Arg Glu Ser
1               5

<210> SEQ ID NO 61
<211> LENGTH: 7
<212> TYPE: PRT
<213> ORGANISM: Mus musculus

<400> SEQUENCE: 61

Gly Ala Thr Ser Leu Glu Thr
1               5

<210> SEQ ID NO 62
<211> LENGTH: 7
<212> TYPE: PRT
<213> ORGANISM: Mus musculus

<400> SEQUENCE: 62

Ser Thr Ser Asn Leu Ala Ser
1               5

<210> SEQ ID NO 63
<211> LENGTH: 7
<212> TYPE: PRT
<213> ORGANISM: Mus musculus

<400> SEQUENCE: 63

Arg Thr Ser Asn Leu Ala Ser
1               5

<210> SEQ ID NO 64
<211> LENGTH: 7
<212> TYPE: PRT
<213> ORGANISM: Mus musculus
```

<400> SEQUENCE: 64

Arg Ala Asn Ile Leu Ile Asp
1               5

<210> SEQ ID NO 65
<211> LENGTH: 9
<212> TYPE: PRT
<213> ORGANISM: Mus musculus

<400> SEQUENCE: 65

Gln Gln Trp Ser Ser Asn Pro Leu Thr
1               5

<210> SEQ ID NO 66
<211> LENGTH: 9
<212> TYPE: PRT
<213> ORGANISM: Mus musculus

<400> SEQUENCE: 66

Leu Gln His Trp Asn Tyr Pro Phe Thr
1               5

<210> SEQ ID NO 67
<211> LENGTH: 9
<212> TYPE: PRT
<213> ORGANISM: Mus musculus

<400> SEQUENCE: 67

Met Gln His Leu Glu Tyr Pro Phe Thr
1               5

<210> SEQ ID NO 68
<211> LENGTH: 9
<212> TYPE: PRT
<213> ORGANISM: Mus musculus

<400> SEQUENCE: 68

Gln Gln His Tyr Ser Thr Pro Tyr Thr
1               5

<210> SEQ ID NO 69
<211> LENGTH: 9
<212> TYPE: PRT
<213> ORGANISM: Mus musculus

<400> SEQUENCE: 69

Gln Gln Tyr Tyr Asp Tyr Pro Tyr Thr
1               5

<210> SEQ ID NO 70
<211> LENGTH: 9
<212> TYPE: PRT
<213> ORGANISM: Mus musculus

<400> SEQUENCE: 70

His Gln Tyr Trp Ser Ile Pro Tyr Thr
1               5

<210> SEQ ID NO 71
<211> LENGTH: 9
<212> TYPE: PRT
<213> ORGANISM: Mus musculus

```
<400> SEQUENCE: 71

His Gln Trp Ser Ser Tyr Pro Tyr Thr
1               5

<210> SEQ ID NO 72
<211> LENGTH: 9
<212> TYPE: PRT
<213> ORGANISM: Mus musculus

<400> SEQUENCE: 72

Gln Gln Tyr His Ser Tyr Pro Ala Thr
1               5

<210> SEQ ID NO 73
<211> LENGTH: 9
<212> TYPE: PRT
<213> ORGANISM: Mus musculus

<400> SEQUENCE: 73

Leu Gln Tyr Asp Glu Phe Pro Tyr Thr
1               5

<210> SEQ ID NO 74
<211> LENGTH: 5
<212> TYPE: PRT
<213> ORGANISM: Mus musculus

<400> SEQUENCE: 74

Asp Phe Gly Met His
1               5

<210> SEQ ID NO 75
<211> LENGTH: 5
<212> TYPE: PRT
<213> ORGANISM: Mus musculus

<400> SEQUENCE: 75

Ser Ser Trp Met Asn
1               5

<210> SEQ ID NO 76
<211> LENGTH: 5
<212> TYPE: PRT
<213> ORGANISM: Mus musculus

<400> SEQUENCE: 76

Asp Tyr Tyr Met Asn
1               5

<210> SEQ ID NO 77
<211> LENGTH: 5
<212> TYPE: PRT
<213> ORGANISM: Mus musculus

<400> SEQUENCE: 77

Asp Tyr Glu Met His
1               5

<210> SEQ ID NO 78
<211> LENGTH: 5
<212> TYPE: PRT
<213> ORGANISM: Mus musculus
```

```
<400> SEQUENCE: 78

Ser Tyr Gly Val Ser
1               5

<210> SEQ ID NO 79
<211> LENGTH: 5
<212> TYPE: PRT
<213> ORGANISM: Mus musculus

<400> SEQUENCE: 79

Thr Tyr Asp Ile His
1               5

<210> SEQ ID NO 80
<211> LENGTH: 5
<212> TYPE: PRT
<213> ORGANISM: Mus musculus

<400> SEQUENCE: 80

Asp Tyr Glu Met His
1               5

<210> SEQ ID NO 81
<211> LENGTH: 5
<212> TYPE: PRT
<213> ORGANISM: Mus musculus

<400> SEQUENCE: 81

Ser Asp Tyr Trp Asn
1               5

<210> SEQ ID NO 82
<211> LENGTH: 5
<212> TYPE: PRT
<213> ORGANISM: Mus musculus

<400> SEQUENCE: 82

Thr Tyr Gly Met Tyr
1               5

<210> SEQ ID NO 83
<211> LENGTH: 17
<212> TYPE: PRT
<213> ORGANISM: Mus musculus

<400> SEQUENCE: 83

Tyr Ile Ser Ser Gly Ser Gly Thr Ile Tyr Tyr Ala Asp Thr Val Arg
1               5                   10                  15

Gly

<210> SEQ ID NO 84
<211> LENGTH: 17
<212> TYPE: PRT
<213> ORGANISM: Mus musculus

<400> SEQUENCE: 84

Arg Ile Tyr Pro Gly Asp Gly Asp Thr Lys Tyr Asn Gly Lys Phe Lys
1               5                   10                  15

Gly

<210> SEQ ID NO 85
<211> LENGTH: 17
```

```
<212> TYPE: PRT
<213> ORGANISM: Mus musculus

<400> SEQUENCE: 85

Asp Ile Ile Pro Ser Asn Gly Gly Thr Ser Tyr Asn Gln Lys Phe Lys
1               5                   10                  15
Gly

<210> SEQ ID NO 86
<211> LENGTH: 17
<212> TYPE: PRT
<213> ORGANISM: Mus musculus

<400> SEQUENCE: 86

Ala Ile Asp Pro Glu Thr Cys Gly Thr Ala Tyr Asn Gln Lys Phe Lys
1               5                   10                  15
Gly

<210> SEQ ID NO 87
<211> LENGTH: 16
<212> TYPE: PRT
<213> ORGANISM: Mus musculus

<400> SEQUENCE: 87

Val Ile Trp Gly Asp Gly Ser Thr Tyr Phe His Ser Ala Leu Ile Ser
1               5                   10                  15

<210> SEQ ID NO 88
<211> LENGTH: 17
<212> TYPE: PRT
<213> ORGANISM: Mus musculus

<400> SEQUENCE: 88

Trp Ile Tyr Pro Arg Asp Gly Arg Thr Thr Tyr Asn Glu Lys Phe Lys
1               5                   10                  15
Ala

<210> SEQ ID NO 89
<211> LENGTH: 17
<212> TYPE: PRT
<213> ORGANISM: Mus musculus

<400> SEQUENCE: 89

Ala Ile Asp Pro Glu Thr Gly Gly Thr Ala Tyr Asn Gln Lys Phe Lys
1               5                   10                  15
Gly

<210> SEQ ID NO 90
<211> LENGTH: 16
<212> TYPE: PRT
<213> ORGANISM: Mus musculus

<400> SEQUENCE: 90

Tyr Ile Asn Tyr Ser Gly Asn Thr Tyr Tyr Asn Pro Ser Leu Lys Ser
1               5                   10                  15

<210> SEQ ID NO 91
<211> LENGTH: 17
<212> TYPE: PRT
<213> ORGANISM: Mus musculus
```

```
<400> SEQUENCE: 91

Trp Ile Asn Thr Tyr Ser Gly Val Pro Thr Tyr Val Asp Asp Phe Lys
1               5                   10                  15

Gly

<210> SEQ ID NO 92
<211> LENGTH: 12
<212> TYPE: PRT
<213> ORGANISM: Mus musculus

<400> SEQUENCE: 92

Gly Asp Leu Tyr Tyr Gly Ser Ser Phe Asp Ala Tyr
1               5                   10

<210> SEQ ID NO 93
<211> LENGTH: 7
<212> TYPE: PRT
<213> ORGANISM: Mus musculus

<400> SEQUENCE: 93

Asp Asp Tyr Asp Trp Ala Ser
1               5

<210> SEQ ID NO 94
<211> LENGTH: 15
<212> TYPE: PRT
<213> ORGANISM: Mus musculus

<400> SEQUENCE: 94

Gly Ile Ser Tyr Tyr Gly Asn Arg Tyr Tyr Phe Thr Met Asp Tyr
1               5                   10                  15

<210> SEQ ID NO 95
<211> LENGTH: 11
<212> TYPE: PRT
<213> ORGANISM: Mus musculus

<400> SEQUENCE: 95

Ser Lys Leu Gly Arg Gly Trp Tyr Phe Asp Val
1               5                   10

<210> SEQ ID NO 96
<211> LENGTH: 15
<212> TYPE: PRT
<213> ORGANISM: Mus musculus

<400> SEQUENCE: 96

Gln Gly Thr Ile Tyr Asp Gly Tyr Tyr Asn Tyr Ala Met Asp Tyr
1               5                   10                  15

<210> SEQ ID NO 97
<211> LENGTH: 6
<212> TYPE: PRT
<213> ORGANISM: Mus musculus

<400> SEQUENCE: 97

Ser Ser Pro Phe Gly Tyr
1               5

<210> SEQ ID NO 98
<211> LENGTH: 4
<212> TYPE: PRT
<213> ORGANISM: Mus musculus
```

-continued

```
<400> SEQUENCE: 98

Gly Phe Asp Tyr
1

<210> SEQ ID NO 99
<211> LENGTH: 13
<212> TYPE: PRT
<213> ORGANISM: Mus musculus

<400> SEQUENCE: 99

Tyr Gly Gly Leu Arg Gln Gly Ser Trp His Phe Asp Val
1               5                   10

<210> SEQ ID NO 100
<211> LENGTH: 6
<212> TYPE: PRT
<213> ORGANISM: Mus musculus

<400> SEQUENCE: 100

Ala Gly Trp Phe Ala Tyr
1               5

<210> SEQ ID NO 101
<211> LENGTH: 17
<212> TYPE: PRT
<213> ORGANISM: Canis familiaris

<400> SEQUENCE: 101

Phe Asn Glu Cys Arg Cys Thr Asp Thr Pro Pro Cys Pro Val Pro Glu
1               5                   10                  15

Pro

<210> SEQ ID NO 102
<211> LENGTH: 22
<212> TYPE: PRT
<213> ORGANISM: Canis familiaris

<400> SEQUENCE: 102

Pro Lys Arg Glu Asn Gly Arg Val Pro Arg Pro Asp Cys Pro Lys
1               5                   10                  15

Cys Pro Ala Pro Glu Met
            20

<210> SEQ ID NO 103
<211> LENGTH: 20
<212> TYPE: PRT
<213> ORGANISM: Canis familiaris

<400> SEQUENCE: 103

Ala Lys Glu Cys Glu Cys Lys Cys Asn Cys Asn Asn Cys Pro Cys Pro
1               5                   10                  15

Gly Cys Gly Leu
            20

<210> SEQ ID NO 104
<211> LENGTH: 17
<212> TYPE: PRT
<213> ORGANISM: Artificial Sequence
<220> FEATURE:
<223> OTHER INFORMATION: modified canis familiaris
```

<400> SEQUENCE: 104

Pro Lys Glu Ser Thr Cys Lys Cys Ile Pro Pro Cys Pro Val Pro Glu
1               5                   10                  15

Ser

<210> SEQ ID NO 105
<211> LENGTH: 429
<212> TYPE: DNA
<213> ORGANISM: Mus musculus

<400> SEQUENCE: 105
atgaacttgg ggctcagctt gattttcctt gtccttgttt taaaaggtgt ccagtgtgac      60
gtgaagctgg tggagtctgg gggaggctta gtgcagcctg agggtccct gaaactctcc     120 tgtgcagcct ctggattcac tttcagtgac tattacatgt attgggttcg ccagactcca    180
gagaagagac tggagtgggt cgcatatgtt agtagtggtg gtggtagtat ctattatcca    240
gacactgtaa agggccgatt caccatctcc agagacaatg ccaagaacac cctgtatttg    300
caaatgagcc gtctgaagtc tgaggacaca gccatgtatt actgtgcaag catgggtcc    360 cccttcggta gtagccgagg ggcctggttt gcttactggg gccaggggac tctggtcact    420
gtctctgca                                                            429

<210> SEQ ID NO 106
<211> LENGTH: 143
<212> TYPE: PRT
<213> ORGANISM: Mus musculus

<400> SEQUENCE: 106

Met Asn Leu Gly Leu Ser Leu Ile Phe Leu Val Leu Val Leu Lys Gly
1               5                   10                  15

Val Gln Cys Asp Val Lys Leu Val Glu Ser Gly Gly Gly Leu Val Gln
                20                  25                  30

Pro Gly Gly Ser Leu Lys Leu Ser Cys Ala Ala Ser Gly Phe Thr Phe
            35                  40                  45

Ser Asp Tyr Tyr Met Tyr Trp Val Arg Gln Thr Pro Glu Lys Arg Leu
        50                  55                  60

Glu Trp Val Ala Tyr Val Ser Ser Gly Gly Gly Ser Ile Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg His Gly Ser Pro Phe Gly Ser Ser Arg Gly Ala
        115                 120                 125

Trp Phe Ala Tyr Trp Gly Gln Gly Thr Leu Val Thr Val Ser Ala
    130                 135                 140

<210> SEQ ID NO 107
<211> LENGTH: 381
<212> TYPE: DNA
<213> ORGANISM: Mus musculus

<400> SEQUENCE: 107
atgagtgtgc ccactcaggt cctggggttg ctgctgctgt ggcttacagg tgccagatgt      60
gacatccaga tgactcagtc tccagcctcc ctgtctgcat ctgtgggaga aactgtcacc    120

```
atcacatgtc gagcaagtga gaatatttac agttatttag catggtatca gcagaaacag    180
ggaaaatctc ctcagctcct ggtctataat gcaaaaacct tagcagaggg tgtgccatca    240
aggttcagtg gcagtggatc aggcacacag ttttctctga agatcaacag cctgcagcct    300
gaagattttg ggaattatta ctgtcaacat tatgatggtt ttccgttcac gttcggtggt    360
gggaccaagc tggagctgaa a                                              381
```

<210> SEQ ID NO 108
<211> LENGTH: 127
<212> TYPE: PRT
<213> ORGANISM: Mus musculus
<400> SEQUENCE: 108

```
Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Asn Tyr Tyr Cys Gln His Tyr Asp
            100                 105                 110

Gly Phe Pro Phe Thr Phe Gly Gly Gly Thr Lys Leu Glu Leu Lys
        115                 120                 125
```

<210> SEQ ID NO 109
<211> LENGTH: 414
<212> TYPE: DNA
<213> ORGANISM: Mus musculus
<400> SEQUENCE: 109

```
atgggttggc tgtggaactt gctattcctg atggcagctg cccaaagtgc ccaagcacag     60
atccagttga tacagtctgg acctgagctg aagaagcctg agagacagt caagatctcc    120 tgcaaggctt ctgggtatac cttcacaacc tttggaatga gctgggtgaa acaggctcca    180
ggaaagggtt taaagtggat gggctggata agcacctact ctggagtgcc aacatatgct    240
gatgacttca aggacggttt tgccttctct ttggaaacct ctgccagcac tgcctatttg    300
cagatcaaca acctcaaaaa tgaggacacg gcttcatatt tctgtgcaag acacaccttc    360
caaagtcgcg ggttggctta ctggggccaa gggactctgg tcactgtctc tgca          414
```

<210> SEQ ID NO 110
<211> LENGTH: 138
<212> TYPE: PRT
<213> ORGANISM: Mus musculus
<400> SEQUENCE: 110

```
Met Gly Trp Leu Trp Asn Leu Leu Phe Leu Met Ala Ala Ala Gln Ser
1               5                   10                  15

Ala Gln Ala Gln Ile Gln Leu Ile Gln Ser Gly Pro Glu Leu Lys Lys
            20                  25                  30
```

```
Pro Gly Glu Thr Val Lys Ile Ser Cys Lys Ala Ser Gly Tyr Thr Phe
        35                  40                  45

Thr Thr Phe Gly Met Ser Trp Val Lys Gln Ala Pro Gly Lys Gly Leu
    50                  55                  60

Lys Trp Met Gly Trp Ile Ser Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Ser
                100                 105                 110

Tyr Phe Cys Ala Arg His Thr Phe Gln Ser Arg Gly Leu Ala Tyr Trp
            115                 120                 125

Gly Gln Gly Thr Leu Val Thr Val Ser Ala
        130                 135
```

<210> SEQ ID NO 111
<211> LENGTH: 393
<212> TYPE: DNA
<213> ORGANISM: Mus musculus

<400> SEQUENCE: 111

```
atgggcatca aaatggagtc acagattcag gtctttgtat tcgtgtttct ctggttgtct    60
ggtgttgacg gagacattgt gatgacccag tctcacaaat tcatgtccac atcagtagga   120
gacagggtca gcatcacctg caaggccagt caggatgtga ttactactgt agcctggtat   180
caacagaaac caggacaatc tcctaaacta ctgatttact cggcatccta ccggtacact   240
ggagtccctg atcgcttcac tggcagtgga tctgggacgg atttcacttt caccatcacc   300
agtgtgcaga ctgaagacct ggcagtttat tactgtcagc aacattatag tactccgtgg   360
acgttcggtg gaggcaccaa gctggaaatc aaa                                393
```

<210> SEQ ID NO 112
<211> LENGTH: 131
<212> TYPE: PRT
<213> ORGANISM: Mus musculus

<400> SEQUENCE: 112

```
Met Gly Ile Lys Met Glu Ser Gln Ile Gln Val Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ile Thr Thr Val Ala Trp Tyr Gln Gln Lys Pro
    50                  55                  60

Gly Gln Ser Pro Lys Leu Leu Ile Tyr Ser Ala Ser Tyr Arg Tyr Thr
65                  70                  75                  80

Gly Val Pro Asp Arg Phe Thr Gly Ser Gly Ser Gly Thr Asp Phe Thr
                85                  90                  95

Phe Thr Ile Thr Ser Val Gln Thr Glu Asp Leu Ala Val Tyr Tyr Cys
                100                 105                 110

Gln Gln His Tyr Ser Thr Pro Trp Thr Phe Gly Gly Gly Thr Lys Leu
            115                 120                 125

Glu Ile Lys
        130
```

<210> SEQ ID NO 113
<211> LENGTH: 411
<212> TYPE: DNA
<213> ORGANISM: Mus musculus

<400> SEQUENCE: 113

| | | |
|---|---|---|
| atgggatgga gctgtatcat gctcttcttg gcagcaacag ctacaggtgt ccactcccag | 60 |
| gtccaactgc agcagcctgg ggctgagctt gtgaagcctg ggcttcagt gaagctgtcc | 120 |
| tgcaaggctt ctggctacac cttcaccaac tactggatac actggatgaa gcagaggcct | 180 |
| ggacgaggcc ttgagtggat tggaaggatt gatcctaata gtggtggtac taagtacaat | 240 |
| gagaagttca agagcaaggc cacactgact gtcgacaaac cctccatcac agcctacatg | 300 |
| cagctcagca gcctgacatc tgaggactct gcggtctatt attgtgcagc attcggtagt | 360 |
| acctacgggt ttgcttactg gggccaaggg actctggtca ctgtctctgc a | 411 |

<210> SEQ ID NO 114
<211> LENGTH: 137
<212> TYPE: PRT
<213> ORGANISM: Mus musculus

<400> SEQUENCE: 114

Met Gly Trp Ser Cys Ile Met Leu Phe Leu Ala Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asn Tyr Trp Ile His Trp Met Lys Gln Arg Pro Gly Arg Gly Leu
    50                  55                  60

Glu Trp Ile Gly Arg Ile Asp Pro Asn Ser Gly Gly Thr Lys Tyr Asn
65                  70                  75                  80

Glu Lys Phe Lys Ser Lys Ala Thr Leu Thr Val Asp Lys Pro Ser Ile
                85                  90                  95

Thr Ala Tyr Met Gln Leu Ser Ser Leu Thr Ser Glu Asp Ser Ala Val
            100                 105                 110

Tyr Tyr Cys Ala Ala Phe Gly Ser Thr Tyr Gly Phe Ala Tyr Trp Gly
        115                 120                 125

Gln Gly Thr Leu Val Thr Val Ser Ala
    130                 135

<210> SEQ ID NO 115
<211> LENGTH: 396
<212> TYPE: DNA
<213> ORGANISM: Mus musculus

<400> SEQUENCE: 115

| | | |
|---|---|---|
| atggattcac aggcccaggt tcttatattg ctgctgctat gggtatctgg tacctgtggg | 60 |
| gacattgtga tgtcacagtc tccatcctcc ctggctgtgt cagcaggaga gaaggtcact | 120 |
| atgagttgca aatccagtca gagtctgctc aacagtagaa cccgaaagaa ctacttggct | 180 |
| tggtaccagc agaaaccagg gcagtctcct aaactgctga tctactgggc atccactagg | 240 |
| gaatctgggg tccctgatcg cttcacaggc agtggatctg ggacagattt cactctcacc | 300 |
| atcagcagtg tgcaggctga agacctggca gtttattact gcaagcaatc ttataatctg | 360 |
| tacacgttcg gagggggac caagctggaa ataaaa | 396 |

<210> SEQ ID NO 116
<211> LENGTH: 132
<212> TYPE: PRT
<213> ORGANISM: Mus musculus

<400> SEQUENCE: 116

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys
    130

<210> SEQ ID NO 117
<211> LENGTH: 429
<212> TYPE: DNA
<213> ORGANISM: Mus musculus

<400> SEQUENCE: 117
atgaacttgg ggctcagctt gattttcctt gtccttgttt taaaaggtgt ccagtgtgaa    60
gtgacgctgg tggagtctgg gggaggctta gtgcagcctg agggtccct gaaactctcc   120 tgtgcagcct ctggattcac tttcagtgac tattacatgt attgggttcg ccagactcca   180
gagaagaggc tggagtgggt cgcatacatt agtcctggtg gtggtagcac ctattatccg   240
gacactataa agggccgatt caccatctcc agagacaatg ccaagaacac cctgtacctg   300
caaatgagcc gtctgaagtc tgaggacaca gccatgtatt actgtacaag acatgggtcc   360
ccctacggta gtagtcgagg ggcctggttt gcttactggg ccaagggac tctggtcact   420 gtctctgca                                                           429

<210> SEQ ID NO 118
<211> LENGTH: 143
<212> TYPE: PRT
<213> ORGANISM: Mus musculus

<400> SEQUENCE: 118

Met Asn Leu Gly Leu Ser Leu Ile Phe Leu Val Leu Val Leu Lys Gly
1               5                   10                  15

Val Gln Cys Glu Val Thr Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

```
Glu Trp Val Ala Tyr Ile Ser Pro Gly Gly Ser Thr Tyr Tyr Pro
 65                  70                  75                  80

Asp Thr Ile Lys Gly Arg Phe Thr Ile Ser Arg Asp Asn Ala Lys Asn
                 85                  90                  95

Thr Leu Tyr Leu Gln Met Ser Arg Leu Lys Ser Glu Asp Thr Ala Met
            100                 105                 110

Tyr Tyr Cys Thr Arg His Gly Ser Pro Tyr Gly Ser Arg Gly Ala
        115                 120                 125

Trp Phe Ala Tyr Trp Gly Gln Gly Thr Leu Val Thr Val Ser Ala
        130                 135                 140

<210> SEQ ID NO 119
<211> LENGTH: 381
<212> TYPE: DNA
<213> ORGANISM: Mus musculus

<400> SEQUENCE: 119
atgagtgtgc ccactcaggt cctggggttg ctgctgctgt ggcttacagg tgccagatgt    60
gacatccaga tgactcagtc tccagcctcc ctatctgcat ctgtgggaga aactgtcacc   120
atcacatgtc gagcaagtga aaatatttac agttatttag catggtatca gcagaaacag   180
ggaaaatctc ctcagctcct ggtctataat ggaaaaacct tagcagaagg tgtgccagca   240
aggttcagtg gcagtggatc aggcacacag ttttctctga agatcaacag cctacagcct   300
gaagattttg ggagttatta ctgtcaacat catgatggta ttccggtcac gttcggtgct   360
gggaccaagc tggagctgaa a                                             381

<210> SEQ ID NO 120
<211> LENGTH: 127
<212> TYPE: PRT
<213> ORGANISM: Mus musculus

<400> SEQUENCE: 120

Met Ser Val Pro Thr Gln Val Leu Gly Leu Leu Leu Leu Trp Leu Thr
  1               5                  10                  15

Gly Ala Arg Cys Asp Ile Gln Met Thr Gln Ser Pro Ala Ser Leu Ser
             20                  25                  30

Ala Ser Val Gly Glu Thr Val Thr Ile Thr Cys Arg Ala Ser Glu Asn
         35                  40                  45

Ile Tyr Ser Tyr Leu Ala Trp Tyr Gln Gln Lys Gln Gly Lys Ser Pro
 50                  55                  60

Gln Leu Leu Val Tyr Asn Gly Lys Thr Leu Ala Glu Gly Val Pro Ala
 65                  70                  75                  80

Arg Phe Ser Gly Ser Gly Ser Gly Thr Gln Phe Ser Leu Lys Ile Asn
                 85                  90                  95

Ser Leu Gln Pro Glu Asp Phe Gly Ser Tyr Tyr Cys Gln His His Asp
            100                 105                 110

Gly Ile Pro Val Thr Phe Gly Ala Gly Thr Lys Leu Glu Leu Lys
        115                 120                 125

<210> SEQ ID NO 121
<211> LENGTH: 423
<212> TYPE: DNA
<213> ORGANISM: Mus musculus
```

<400> SEQUENCE: 121

```
atgaacttgg ggctcagctt gattttcctt gtccttgttt taaaaggtgt ccagtgtgaa      60
gtgaagctgg tggagtcggg gggaggctta gtgcagcctg agggtccct gaaactctcc     120
tgtgtagcct ctggattcac tttcagtgac tatcacatgc attgggttcg ccagactcca     180
gagaagaggc tggagtgggt cgcatacatt agtaaaggtg gtggtagcac ctattatcca     240
gacactgaaa agggccgatt caccatctcc agagacaatg ccaagaatac cctgtacctg     300
caaatgagcc gtctgaagtc tgaggacaca gccatgtatt actgtgcaag atcccccggc     360
cctagtagct ctactggta cttcgatgtc tggggcacag ggaccacggt caccgtctcc     420
tca                                                                   423
```

<210> SEQ ID NO 122
<211> LENGTH: 141
<212> TYPE: PRT
<213> ORGANISM: Mus musculus

<400> SEQUENCE: 122

```
Met Asn Leu Gly Leu Ser Leu Ile Phe Leu Val Leu Val Leu Lys Gly
1               5                   10                  15
Val Gln Cys Glu Val Lys Leu Val Glu Ser Gly Gly Gly Leu Val Gln
            20                  25                  30
Pro Gly Gly Ser Leu Lys Leu Ser Cys Val Ala Ser Gly Phe Thr Phe
        35                  40                  45
Ser Asp Tyr His Met His Trp Val Arg Gln Thr Pro Glu Lys Arg Leu
    50                  55                  60
Glu Trp Val Ala Tyr Ile Ser Lys Gly Gly Gly Ser Thr Tyr Tyr Pro
65                  70                  75                  80
Asp Thr Glu Lys Gly Arg Phe Thr Ile Ser Arg Asp Asn Ala Lys Asn
                85                  90                  95
Thr Leu Tyr Leu Gln Met Ser Arg Leu Lys Ser Glu Asp Thr Ala Met
            100                 105                 110
Tyr Tyr Cys Ala Arg Ser Pro Gly Pro Ser Ser Phe Tyr Trp Tyr Phe
        115                 120                 125
Asp Val Trp Gly Thr Gly Thr Thr Val Thr Val Ser Ser
    130                 135                 140
```

<210> SEQ ID NO 123
<211> LENGTH: 381
<212> TYPE: DNA
<213> ORGANISM: Mus musculus

<400> SEQUENCE: 123

```
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gagcaagtga gaatatttac agttatttag catggtatca gcagaaacag     180
ggaaaatctc ctcagctcct ggtctataat gcaaaaacct agcagaaagg tgtgccatca     240
aggttcagtg gcagtggatc aggcacacag ttttctctga agatcaacag cctgcagcct     300
gaagattttg ggagttatta ctgtcaacat cattatggta ttccggtcac ggtcggtgta     360
gggaccaagc tggagctgaa a                                               381
```

<210> SEQ ID NO 124
<211> LENGTH: 127

<212> TYPE: PRT
<213> ORGANISM: Mus musculus

<400> SEQUENCE: 124

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His His Tyr
            100                 105                 110

Gly Ile Pro Val Thr Val Gly Val Gly Thr Lys Leu Glu Leu Lys
        115                 120                 125

<210> SEQ ID NO 125
<211> LENGTH: 11
<212> TYPE: PRT
<213> ORGANISM: Canis familiaris

<400> SEQUENCE: 125

Ser Ala Glu Leu Arg Leu Ser Tyr Gln Leu Asp
1               5                   10

<210> SEQ ID NO 126
<211> LENGTH: 11
<212> TYPE: PRT
<213> ORGANISM: Canis familiaris

<400> SEQUENCE: 126

Phe Gln Pro Ser Lys His Val Lys Pro Arg Thr
1               5                   10

<210> SEQ ID NO 127
<211> LENGTH: 21
<212> TYPE: PRT
<213> ORGANISM: Canis familiaris

<400> SEQUENCE: 127

Ala Gly Gln Gln Leu Leu Trp Ser Gly Ser Phe Gln Pro Ser Lys His
1               5                   10                  15

Val Lys Pro Arg Thr
            20

<210> SEQ ID NO 128
<211> LENGTH: 9
<212> TYPE: PRT
<213> ORGANISM: Canis familiaris

<400> SEQUENCE: 128

Thr Leu Lys Ser Gly Ala Ser Tyr Ser
1               5

<210> SEQ ID NO 129
<211> LENGTH: 11

<212> TYPE: PRT
<213> ORGANISM: Mus musculus

<400> SEQUENCE: 129

Arg Ala Ser Glu Asn Ile Tyr Ser Tyr Leu Ala
1               5                   10

<210> SEQ ID NO 130
<211> LENGTH: 11
<212> TYPE: PRT
<213> ORGANISM: Mus musculus

<400> SEQUENCE: 130

Lys Ala Ser Gln Asp Val Ile Thr Thr Val Ala
1               5                   10

<210> SEQ ID NO 131
<211> LENGTH: 17
<212> TYPE: PRT
<213> ORGANISM: Mus musculus

<400> SEQUENCE: 131

Lys Ser Ser Gln Ser Leu Leu Asn Ser Arg Thr Arg Lys Asn Tyr Leu
1               5                   10                  15

Ala

<210> SEQ ID NO 132
<211> LENGTH: 7
<212> TYPE: PRT
<213> ORGANISM: Mus musculus

<400> SEQUENCE: 132

Asn Ala Lys Thr Leu Ala Glu
1               5

<210> SEQ ID NO 133
<211> LENGTH: 7
<212> TYPE: PRT
<213> ORGANISM: Mus musculus

<400> SEQUENCE: 133

Ser Ala Ser Tyr Arg Tyr Thr
1               5

<210> SEQ ID NO 134
<211> LENGTH: 7
<212> TYPE: PRT
<213> ORGANISM: Mus musculus

<400> SEQUENCE: 134

Asn Gly Lys Thr Leu Ala Glu
1               5

<210> SEQ ID NO 135
<211> LENGTH: 9
<212> TYPE: PRT
<213> ORGANISM: Mus musculus

<400> SEQUENCE: 135

Gln His Tyr Asp Gly Phe Pro Phe Thr
1               5

<210> SEQ ID NO 136
<211> LENGTH: 9

<212> TYPE: PRT
<213> ORGANISM: Mus musculus

<400> SEQUENCE: 136

Gln Gln His Tyr Ser Thr Pro Trp Thr
1               5

<210> SEQ ID NO 137
<211> LENGTH: 9
<212> TYPE: PRT
<213> ORGANISM: Mus musculus

<400> SEQUENCE: 137

Gln His His Asp Gly Ile Pro Val Thr
1               5

<210> SEQ ID NO 138
<211> LENGTH: 8
<212> TYPE: PRT
<213> ORGANISM: Mus musculus

<400> SEQUENCE: 138

Lys Gln Ser Tyr Asn Leu Tyr Thr
1               5

<210> SEQ ID NO 139
<211> LENGTH: 9
<212> TYPE: PRT
<213> ORGANISM: Mus musculus

<400> SEQUENCE: 139

Gln His His Tyr Gly Ile Pro Val Thr
1               5

<210> SEQ ID NO 140
<211> LENGTH: 5
<212> TYPE: PRT
<213> ORGANISM: Mus musculus

<400> SEQUENCE: 140

Asp Tyr Tyr Met Tyr
1               5

<210> SEQ ID NO 141
<211> LENGTH: 5
<212> TYPE: PRT
<213> ORGANISM: Mus musculus

<400> SEQUENCE: 141

Thr Phe Gly Met Ser
1               5

<210> SEQ ID NO 142
<211> LENGTH: 5
<212> TYPE: PRT
<213> ORGANISM: Mus musculus

<400> SEQUENCE: 142

Asn Tyr Trp Ile His
1               5

<210> SEQ ID NO 143
<211> LENGTH: 5
<212> TYPE: PRT
<213> ORGANISM: Mus musculus

```
<400> SEQUENCE: 143

Asp Tyr His Met His
1               5

<210> SEQ ID NO 144
<211> LENGTH: 17
<212> TYPE: PRT
<213> ORGANISM: Mus musculus

<400> SEQUENCE: 144

Tyr Val Ser Ser Gly Gly Gly Ser Ile Tyr Tyr Pro Asp Thr Val Lys
1               5                   10                  15

Gly

<210> SEQ ID NO 145
<211> LENGTH: 17
<212> TYPE: PRT
<213> ORGANISM: Mus musculus

<400> SEQUENCE: 145

Trp Ile Ser Thr Tyr Ser Gly Val Pro Thr Tyr Ala Asp Asp Phe Lys
1               5                   10                  15

Gly

<210> SEQ ID NO 146
<211> LENGTH: 17
<212> TYPE: PRT
<213> ORGANISM: Mus musculus

<400> SEQUENCE: 146

Tyr Ile Ser Pro Gly Gly Gly Ser Thr Tyr Tyr Pro Asp Thr Ile Lys
1               5                   10                  15

Gly

<210> SEQ ID NO 147
<211> LENGTH: 17
<212> TYPE: PRT
<213> ORGANISM: Mus musculus

<400> SEQUENCE: 147

Arg Ile Asp Pro Asn Ser Gly Gly Thr Lys Tyr Asn Glu Lys Phe Lys
1               5                   10                  15

Ser

<210> SEQ ID NO 148
<211> LENGTH: 17
<212> TYPE: PRT
<213> ORGANISM: Mus musculus

<400> SEQUENCE: 148

Tyr Ile Ser Lys Gly Gly Gly Ser Thr Tyr Tyr Pro Asp Thr Glu Lys
1               5                   10                  15

Gly

<210> SEQ ID NO 149
<211> LENGTH: 15
<212> TYPE: PRT
<213> ORGANISM: Mus musculus
```

```
<400> SEQUENCE: 149

His Gly Ser Pro Phe Gly Ser Ser Arg Gly Ala Trp Phe Ala Tyr
1               5                   10                  15

<210> SEQ ID NO 150
<211> LENGTH: 10
<212> TYPE: PRT
<213> ORGANISM: Mus musculus

<400> SEQUENCE: 150

His Thr Phe Gln Ser Arg Gly Leu Ala Tyr
1               5                   10

<210> SEQ ID NO 151
<211> LENGTH: 15
<212> TYPE: PRT
<213> ORGANISM: Mus musculus

<400> SEQUENCE: 151

His Gly Ser Pro Tyr Gly Ser Ser Arg Gly Ala Trp Phe Ala Tyr
1               5                   10                  15

<210> SEQ ID NO 152
<211> LENGTH: 9
<212> TYPE: PRT
<213> ORGANISM: Mus musculus

<400> SEQUENCE: 152

Phe Gly Ser Thr Tyr Gly Phe Ala Tyr
1               5

<210> SEQ ID NO 153
<211> LENGTH: 13
<212> TYPE: PRT
<213> ORGANISM: Mus musculus

<400> SEQUENCE: 153

Ser Pro Gly Pro Ser Ser Phe Tyr Trp Tyr Phe Asp Val
1               5                   10

<210> SEQ ID NO 154
<211> LENGTH: 11
<212> TYPE: PRT
<213> ORGANISM: Canis familiaris

<400> SEQUENCE: 154

Glu Asp Ser Val Cys Val Cys Ser Met Pro Ile
1               5                   10

<210> SEQ ID NO 155
<211> LENGTH: 12
<212> TYPE: PRT
<213> ORGANISM: Canis familiaris

<400> SEQUENCE: 155

Met Trp Thr Asn Pro Tyr Pro Thr Glu Asn His Leu
1               5                   10

<210> SEQ ID NO 156
<211> LENGTH: 7
<212> TYPE: PRT
<213> ORGANISM: Canis familiaris
```

<400> SEQUENCE: 156

Ala Ser Thr Leu Lys Ser Gly
1               5

<210> SEQ ID NO 157
<211> LENGTH: 14
<212> TYPE: PRT
<213> ORGANISM: Canis familiaris

<400> SEQUENCE: 157

Trp Ser Gly Ser Phe Gln Pro Ser Lys His Val Lys Pro Arg
1               5                   10

<210> SEQ ID NO 158
<211> LENGTH: 12
<212> TYPE: PRT
<213> ORGANISM: Canis familiaris

<400> SEQUENCE: 158

Val Tyr Asn Val Thr Tyr Met Gly Pro Thr Leu Arg
1               5                   10

<210> SEQ ID NO 159
<211> LENGTH: 18
<212> TYPE: PRT
<213> ORGANISM: Canis familiaris

<400> SEQUENCE: 159

Val Leu His Glu Pro Ser Cys Phe Ser Asp Tyr Ile Ser Thr Ser Val
1               5                   10                  15

Cys Gln

<210> SEQ ID NO 160
<211> LENGTH: 14
<212> TYPE: PRT
<213> ORGANISM: Canis familiaris

<400> SEQUENCE: 160

Glu Asn Arg Glu Asp Ser Val Cys Val Cys Ser Met Pro Ile
1               5                   10

<210> SEQ ID NO 161
<211> LENGTH: 13
<212> TYPE: PRT
<213> ORGANISM: Canis familiaris

<400> SEQUENCE: 161

Lys Ser Gly Ala Ser Tyr Ser Ala Arg Val Arg Ala Trp
1               5                   10

<210> SEQ ID NO 162
<211> LENGTH: 10
<212> TYPE: PRT
<213> ORGANISM: Canis familiaris

<400> SEQUENCE: 162

Tyr Tyr Glu Pro Trp Glu Gln His Leu Pro
1               5                   10

<210> SEQ ID NO 163
<211> LENGTH: 1359
<212> TYPE: DNA
<213> ORGANISM: Artificial Sequence

```
<220> FEATURE:
<223> OTHER INFORMATION: Chimeric canine mouse

<400> SEQUENCE: 163
gaggtgcagc tggtggagag cggaggcgac ctggtgaaac ccggaggcag cctgagactg      60
agctgtgtgg ccagcggcta caccttcacc aactactgga ttcattgggt gaggcaggct     120
cccggcaaag gactgcagtg ggtggccagg attgatccca acagcggcgg caccaagtac     180
aacgagaagt tcaagagcag gttcaccatc agcagggaca cgccaagaa cccctctac       240
ctgcagatga acagcctgag ggccgaggac accgccgtgt actactgcac caggttcggc     300
agcacctacg gcttcgccta ctgggggcaa ggcaccctgg tgaccgtgag cagcgcttcc     360
acaaccgcgc catcagtctt tccgttggcc catcatgcg gtcgacgag cggatcgact       420
gtggccctgg cgtgcttggt gtcgggatac tttcccgaac ccgtcacggt cagctggaac     480
tccggatcgc ttacgagcgg tgtgcatacg ttcccctcgg tcttgcaatc atcagggctc     540
tactcgctgt cgagcatggt aacggtgccc tcatcgaggt ggccctccga acgttcaca      600
tgtaacgtag cacatccagc tccaaaacc aaggtggata aacccgtgcc gaaaagagag      660
aatgggcggt gcctcgacc ccctgattgc cccaagtgtc cggctccgga atgctcggt       720
ggaccctcag tgtttatctt ccctccgaag cccaaggaca ctctgctgat cgcgcgcact     780
ccagaagtaa catgtgtagt ggtggcactt gatcccgagg accccgaagt ccagatctcc     840
tggtttgtag atgggaaaca gatgcagacc gcaaaaactc aacccagaga ggagcagttc     900
gcaggaacat accgagtggt atccgtcctt ccgattggcc accaggactg gttgaaaggg     960
aagcagttta cgtgtaaagt caacaataag gcgttgccta gccctattga gcggacgatt    1020
tcgaaagcta ggggacaggc ccaccagcca tcggtctatg tccttccgcc ttcccgcgag    1080
gagctctcga agaatacagt gagccttaca tgcctcatta aggatttctt cccgcctgat    1140
atcgacgtag agtggcaatc aaacggtcaa caggagccgg aatccaagta tagaaccact    1200
ccgccccagc ttgacgagga cggatcatac tttttgtatt caaaactgtc ggtggataag    1260
agccggtggc agagaggtga caccttcatc tgtgcggtga tgcacgaagc actccataat    1320
cactacaccc aagagagcct ctcgcattcc cccggaaag                            1359

<210> SEQ ID NO 164
<211> LENGTH: 453
<212> TYPE: PRT
<213> ORGANISM: Artificial Sequence
<220> FEATURE:
<223> OTHER INFORMATION: Chimeric canine mouse

<400> SEQUENCE: 164

Glu Val Gln Leu Val Glu Ser Gly Gly Asp Leu Val Lys Pro Gly Gly
1               5                  10                   15

Ser Leu Arg Leu Ser Cys Val Ala Ser Gly Tyr Thr Phe Thr Asn Tyr
            20                  25                   30

Trp Ile His Trp Val Arg Gln Ala Pro Gly Lys Gly Leu Gln Trp Val
        35                   40                   45

Ala Arg Ile Asp Pro Asn Ser Gly Gly Thr Lys Tyr Asn Glu Lys Phe
    50                   55                   60

Lys Ser Arg Phe Thr Ile Ser Arg Asp Asn Ala Lys Asn Thr Leu Tyr
65                   70                   75                   80

Leu Gln Met Asn Ser Leu Arg Ala Glu Asp Thr Ala Val Tyr Tyr Cys
                85                   90                   95
```

```
Thr Arg Phe Gly Ser Thr Tyr Gly Phe Ala Tyr Trp Gly Gln Gly Thr
            100                 105                 110

Leu Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
        130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
            195                 200                 205

Lys Thr Lys Val Asp Lys Pro Val Pro Lys Arg Glu Asn Gly Arg Val
        210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Ala Leu Asp Pro
            260                 265                 270

Glu Asp Pro Glu Val Gln Ile Ser Trp Phe Val Asp Gly Lys Gln Met
            275                 280                 285

Gln Thr Ala Lys Thr Gln Pro Arg Glu Glu Gln Phe Ala Gly Thr Tyr
        290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
        370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
        435                 440                 445

His Ser Pro Gly Lys
        450

<210> SEQ ID NO 165
<211> LENGTH: 1359
<212> TYPE: DNA
<213> ORGANISM: Artificial Sequence
<220> FEATURE:
<223> OTHER INFORMATION: Chimeric canine mouse
```

-continued

```
<400> SEQUENCE: 165
gaggtgcagc tggtggagag cggcggagat ctggtgaagc cggcggaag cctgagactg      60
agctgtgtgg ccagcggcta caccttcacc aactactgga ttcattgggt gagacaggcc    120
cctggcaagg gcctgcagtg gatcggcagg atcgacccca cagcggcgg caccaagtac    180
aacgagaagt tcaagagcaa ggccaccctg agcgtggaca aggccaagaa caccctgtac    240
ctgcagatga actccctgag ggccgaggac accgccgtgt actactgcgc cgcctttggc    300
agcacctacg gcttcgccta ctggggccag ggaaccctgg tgaccgtgag cagcgcttcc    360
acaaccgcgc catcagtctt tccgttggcc ccatcatgcg ggtcgacgag cggatcgact    420
gtggccctgg cgtgcttggt gtcgggatac tttcccgaac ccgtcacggt cagctggaac    480
tccggatcgc ttacgagcgg tgtgcatacg ttccctcgg tcttgcaatc atcagggctc     540
tactcgctgt cgagcatggt aacggtgccc tcatcgaggt ggccctccga acgttcaca    600
tgtaacgtag cacatccagc ctccaaaacc aaggtggata aacccgtgcc gaaaagagag   660
aatgggcggg tgcctcgacc ccctgattgc cccaagtgtc cggctccgga atgctcggt     720
ggaccctcag tgtttatctt ccctccgaag cccaaggaca ctctgctgat cgcgcgcact    780
ccagaagtaa catgtgtagt ggtggcactt gatcccgagg accccgaagt ccagatctcc    840
tggtttgtag atgggaaaca gatgcagacc gcaaaaactc aacccagaga ggagcagttc    900
gcaggaacat accgagtggt atccgtcctt ccgattggcc accaggactg gttgaagggg    960
aagcagttta cgtgtaaagt caacaataag gcgttgccta gccctattga gcggacgatt   1020
tcgaaagcta ggggacaggc ccaccagcca tcggtctatg tcttccgcc ttcccgcgag    1080
gagctctcga gaatacagt gagccttaca tgcctcatta aggatttctt cccgcctgat   1140
atcgacgtag agtggcaatc aaacggtcaa caggagccgg aatccaagta tagaaccact  1200
ccgcccagc ttgacgagga cggatcatac ttttttgtatt caaaactgtc ggtggataag   1260
agccggtggc agagaggtga caccttcatc tgtgcggtga tgcacgaagc actccataat  1320
cactacaccc aagagagcct ctcgcattcc cccggaaag                         1359
```

<210> SEQ ID NO 166
<211> LENGTH: 453
<212> TYPE: PRT
<213> ORGANISM: Artificial Sequence
<220> FEATURE:
<223> OTHER INFORMATION: Chimeric canine mouse

<400> SEQUENCE: 166

Glu Val Gln Leu Val Glu Ser Gly Gly Asp Leu Val Lys Pro Gly Gly
1               5                   10                  15

Ser Leu Arg Leu Ser Cys Val Ala Ser Gly Tyr Thr Phe Thr Asn Tyr
                20                  25                  30

Trp Ile His Trp Val Arg Gln Ala Pro Gly Lys Gly Leu Gln Trp Ile
            35                  40                  45

Gly Arg Ile Asp Pro Asn Ser Gly Thr Lys Tyr Asn Glu Lys Phe
        50                  55                  60

Lys Ser Lys Ala Thr Leu Ser Val Asp Lys Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Phe Gly Ser Thr Tyr Gly Phe Ala Tyr Trp Gly Gln Gly Thr
                100                 105                 110

```
Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
        195                 200                 205

Lys Thr Lys Val Asp Lys Pro Val Pro Lys Arg Glu Asn Gly Arg Val
        210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Ala Leu Asp Pro
            260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Ala Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
        355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
        435                 440                 445

His Ser Pro Gly Lys
        450

<210> SEQ ID NO 167
<211> LENGTH: 1359
<212> TYPE: DNA
<213> ORGANISM: Artificial Sequence
<220> FEATURE:
<223> OTHER INFORMATION: Chimeric canine mouse
```

<400> SEQUENCE: 167

```
gaggtgcagc tggtggagag cggcggcgat ctggtgaagc ctggcggaag cctgagactg      60
agctgcgtgg ccagcggcta caccttcacc aactactgga ttcattggat gaggcaggcc     120
cctggcaagg gactgcagtg gatcggcaga atcgacccca acagcggcgg caccaagtac     180
aacgagaagt tcaagagcaa ggccaccctg agcgtggaca aggccaagaa caccgcctac     240
atgcagctga acagcctgag ggccgaggac accgccgtgt actactgcgc cgcctttggc     300
agcacctacg gcttcgccta ttggggccag ggcaccctgg tgaccgtgag cagcgcttcc     360
acaaccgcgc catcagtctt tccgttggcc ccatcatgcg ggtcgacgag cggatcgact     420
gtggccctgg cgtgcttggt gtcgggatac tttcccgaac ccgtcacggt cagctggaac     480
tccggatcgc ttacgagcgg tgtgcatacg ttccctcgg tcttgcaatc atcagggctc      540
tactcgctgt cgagcatggt aacggtgccc tcatcgaggt ggccctccga acgttcaca     600
tgtaacgtag cacatccagc ctccaaaacc aaggtggata aacccgtgcc gaaaagagag     660
aatgggcggg tgcctcgacc ccctgattgc cccaagtgtc cggctccgga atgctcggt     720
ggaccctcag tgtttatctt ccctccgaag cccaaggaca ctctgctgat cgcgcgcact     780
ccagaagtaa catgtgtagt ggtggcactt gatcccgagg accccgaagt ccagatctcc     840
tggtttgtag atgggaaaca gatgcagacc gcaaaaactc aacccagaga ggagcagttc     900
gcaggaacat accgagtggt atccgtcctt ccgattggcc accaggactg gttgaaaggg     960
aagcagtta cgtgtaaagt caacaataag gcgttgccta gccctattga gcggacgatt    1020
tcgaaagcta ggggacaggc ccaccagcca tcggtctatg tccttccgcc ttcccgcgag    1080
gagctctcga gaatacagt gagccttaca tgcctcatta aggatttctt cccgcctgat    1140
atcgacgtag agtggcaatc aaacggtcaa caggagccgg aatccaagta tagaaccact    1200
ccgcccagc ttgacgagga cggatcatac tttttgtatt caaaactgtc ggtggataag    1260
agccggtggc agagaggtga caccttcatc tgtgcggtga tgcacgaagc actccataat    1320
cactacaccc aagagagcct ctcgcattcc cccggaaag                            1359
```

<210> SEQ ID NO 168
<211> LENGTH: 453
<212> TYPE: PRT
<213> ORGANISM: Artificial Sequence
<220> FEATURE:
<223> OTHER INFORMATION: Chimeric canine mouse

<400> SEQUENCE: 168

```
Glu Val Gln Leu Val Glu Ser Gly Gly Asp Leu Val Lys Pro Gly Gly
1               5                   10                  15

Ser Leu Arg Leu Ser Cys Val Ala Ser Gly Tyr Thr Phe Thr Asn Tyr
            20                  25                  30

Trp Ile His Trp Met Arg Gln Ala Pro Gly Lys Gly Leu Gln Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Ser Val Asp Lys Ala Lys Asn Thr Ala Tyr
65                  70                  75                  80

Met Gln Leu Asn Ser Leu Arg Ala Glu Asp Thr Ala Val Tyr Tyr Cys
                85                  90                  95

Ala Ala Phe Gly Ser Thr Tyr Gly Phe Ala Tyr Trp Gly Gln Gly Thr
            100                 105                 110
```

Leu Val Thr Val Ser Ser Ala Ser Thr Thr Ala Pro Ser Val Phe Pro
    115                 120                 125

Leu Ala Pro Ser Cys Gly Ser Thr Ser Gly Ser Thr Val Ala Leu Ala
130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
            195                 200                 205

Lys Thr Lys Val Asp Lys Pro Val Pro Lys Arg Glu Asn Gly Arg Val
            210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Ala Leu Asp Pro
            260                 265                 270

Glu Asp Pro Glu Val Gln Ile Ser Trp Phe Val Asp Gly Lys Gln Met
            275                 280                 285

Gln Thr Ala Lys Thr Gln Pro Arg Glu Glu Gln Phe Ala Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
            435                 440                 445

His Ser Pro Gly Lys
    450

<210> SEQ ID NO 169
<211> LENGTH: 669
<212> TYPE: DNA
<213> ORGANISM: Artificial Sequence
<220> FEATURE:
<223> OTHER INFORMATION: Chimeric canine mouse

<400> SEQUENCE: 169

```
gacatcgtga tgacccagac ccctctgagc ctgtccgtga gccctggcga acctgccagc      60
atcagctgca agagcagcca gagcctgctg aacagcagga ccaggaagaa ctacctggcc     120
tggttcagac agaagcccgg ccagagcccc cagagactga tctactgggc cagcaccaga     180
gagagcggcg tgcctgacag atttagcggc agcggcagcg gcacagactt caccctgagg     240
atcagcagag tggaggccga cgatgccggc gtgtactact gcaagcagag ctacaacctg     300
tacaccttcg gccagggcac caaggtggag atcaagagga cgacgctca gccagccgtg     360
tacctcttcc agccttcgcc ggaccagctt catacggggt cagcgtcggt ggtgtgcctg     420
ttgaactcgt tttaccccaa ggacattaac gtgaagtgga aggtagacgg ggtaattcaa     480
gacactggca ttcaagagtc cgtcacggaa caagactcaa aagactcaac gtattcactg     540
tcgtcaacct tgacgatgtc aagcaccgag tatcttagcc atgagctgta ttcgtgcgag     600
atcacccaca gtccctccc ctccactctt atcaaatcct ttcagcggtc ggaatgtcag     660
cgggtcgat                                                              669
```

<210> SEQ ID NO 170
<211> LENGTH: 223
<212> TYPE: PRT
<213> ORGANISM: Artificial Sequence
<220> FEATURE:
<223> OTHER INFORMATION: Chimeric canine mouse

<400> SEQUENCE: 170

```
Asp Ile Val Met Thr Gln Thr Pro Leu Ser Leu Ser Val Ser Pro Gly
1               5                   10                  15
Glu Pro Ala Ser Ile Ser Cys Lys Ser Ser Gln Ser Leu Leu Asn Ser
            20                  25                  30
Arg Thr Arg Lys Asn Tyr Leu Ala Trp Phe Arg Gln Lys Pro Gly Gln
        35                  40                  45
Ser Pro Gln Arg Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Arg
65                  70                  75                  80
Ile Ser Arg Val Glu Ala Asp Asp Ala Gly Val Tyr Tyr Cys Lys Gln
                85                  90                  95
Ser Tyr Asn Leu Tyr Thr Phe Gly Gln Gly Thr Lys Val Glu Ile Lys
            100                 105                 110
Arg Asn Asp Ala Gln Pro Ala Val Tyr Leu Phe Gln Pro Ser Pro Asp
        115                 120                 125
Gln Leu His Thr Gly Ser Ala Ser Val Val Cys Leu Leu Asn Ser Phe
    130                 135                 140
Tyr Pro Lys Asp Ile Asn Val Lys Trp Lys Val Asp Gly Val Ile Gln
145                 150                 155                 160
Asp Thr Gly Ile Gln Glu Ser Val Thr Glu Gln Asp Ser Lys Asp Ser
                165                 170                 175
Thr Tyr Ser Leu Ser Ser Thr Leu Thr Met Ser Ser Thr Glu Tyr Leu
            180                 185                 190
Ser His Glu Leu Tyr Ser Cys Glu Ile Thr His Lys Ser Leu Pro Ser
        195                 200                 205
Thr Leu Ile Lys Ser Phe Gln Arg Ser Glu Cys Gln Arg Val Asp
    210                 215                 220
```

<210> SEQ ID NO 171
<211> LENGTH: 669
<212> TYPE: DNA
<213> ORGANISM: Artificial Sequence
<220> FEATURE:
<223> OTHER INFORMATION: Chimeric canine mouse

<400> SEQUENCE: 171

```
gacatcgtga tgacccagac ccctctgagc ctgagcgtga gccctggaga gcctgccagc      60
atcagctgca agagcagcca gagcctgctg aacagcagga ccaggaagaa ctacctggcc     120
tggtacaggc agaagcctgg ccagagcccc cagctgctga tctactgggc cagcaccaga     180
gagagcggag tgcctgacag gttcagcgga agcggcagcg gcaccgactt cacc ctgagg    240 atcagcagag tggaggccga tgacgccggc gtgtactact gcaagcagag ctacaacctg     300
tacaccttcg gccagggcac caaggtggag atcaagagga cgacgctca gccagccgtg      360 tacctcttcc agccttcgcc ggaccagctt catacggggt cagcgtcggt ggtgtgcctg     420
ttgaactcgt tttaccccaa ggacattaac gtgaagtgga aggtagacgg ggtaattcaa     480
gacactggca ttcaagagtc cgtcacggaa caagactcaa aagactcaac gtattcactg     540
tcgtcaacct tgacgatgtc aagcaccgag tatcttagcc atgagctgta ttcgtgcgag     600
atcacccaca agtccctccc ctccactctt atcaaatcct ttcagcggtc ggaatgtcag     660
cgggtcgat                                                             669
```

<210> SEQ ID NO 172
<211> LENGTH: 223
<212> TYPE: PRT
<213> ORGANISM: Artificial Sequence
<220> FEATURE:
<223> OTHER INFORMATION: Chimeric canine mouse

<400> SEQUENCE: 172

```
Asp Ile Val Met Thr Gln Thr Pro Leu Ser Leu Ser Val Ser Pro Gly
1               5                   10                  15

Glu Pro Ala Ser Ile Ser Cys Lys Ser Ser Gln Ser Leu Leu Asn Ser
            20                  25                  30

Arg Thr Arg Lys Asn Tyr Leu Ala Trp Tyr Arg Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Arg
65                  70                  75                  80

Ile Ser Arg Val Glu Ala Asp Asp Ala Gly Val Tyr Tyr Cys Lys Gln
                85                  90                  95

Ser Tyr Asn Leu Tyr Thr Phe Gly Gln Gly Thr Lys Val Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190
```

```
Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
        210                 215                 220
```

<210> SEQ ID NO 173
<211> LENGTH: 669
<212> TYPE: DNA
<213> ORGANISM: Artificial Sequence
<220> FEATURE:
<223> OTHER INFORMATION: Chimeric canine mouse

<400> SEQUENCE: 173

```
gacatcgtga tgacccagac ccctctgagc ctgagcgtga gccctggaga gcctgccagc    60
atcagctgca agagcagcca gagcctgctg aacagcagga ccaggaagaa ctacctggcc   120
tggtaccagc agaagcctgg ccagagcccc agctgctga tctactgggc cagcaccaga   180
gagagcggag tgcctgacag gttcagcgga agcggcagcg gcaccgactt cacccctgagg  240
atcagcagag tggaggccga tgacgccggc gtgtactact gcaagcagag ctacaacctg   300
tacaccttcg gccagggcac caaggtggag atcaagagga cgacgctca gccagccgtg   360
tacctcttcc agccttcgcc ggaccagctt catacggggt cagcgtcggt ggtgtgcctg   420
ttgaactcgt tttaccccaa ggacattaac gtgaagtgga aggtagacgg ggtaattcaa   480
gacactggca ttcaagagtc cgtcacggaa caagactcaa aagactcaac gtattcactg   540
tcgtcaacct tgacgatgtc aagcaccgag tatcttagcc atgagctgta ttcgtgcgag   600
atcacccaca gtccctcccc ctccactctt atcaaatcct ttcagcggtc ggaatgtcag   660
cgggtcgat                                                           669
```

<210> SEQ ID NO 174
<211> LENGTH: 223
<212> TYPE: PRT
<213> ORGANISM: Artificial Sequence
<220> FEATURE:
<223> OTHER INFORMATION: Chimeric canine mouse

<400> SEQUENCE: 174

```
Asp Ile Val Met Thr Gln Thr Pro Leu Ser Leu Ser Val Ser Pro Gly
1               5                   10                  15

Glu Pro Ala Ser Ile Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Arg
65                  70                  75                  80

Ile Ser Arg Val Glu Ala Asp Asp Ala Gly Val Tyr Tyr Cys Lys Gln
                85                  90                  95

Ser Tyr Asn Leu Tyr Thr Phe Gly Gln Gly Thr Lys Val Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140
```

```
Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

UNITED STATES PATENT AND TRADEMARK OFFICE
CERTIFICATE OF CORRECTION

PATENT NO. : 12,180,288 B2
APPLICATION NO. : 17/081188
DATED : December 31, 2024
INVENTOR(S) : Mohamad Morsey et al.

It is certified that error appears in the above-identified patent and that said Letters Patent is hereby corrected as shown below:

In the Claims

Claim 1:
In Column 193, Line 28, replace the first instance of "VH" with "heavy chain variable region (VH)".

Claim 11:
In Column 194, Line 34, replace "the amino acid" with "an amino acid".
In Column 194, Line 35, replace "sequence of" with "sequence selected from the group consisting of".

Claim 15:
In Column 194, Line 54, add "the antibody or antigen binding fragment thereof" before "binds".

Claim 16:
In Column 194, Line 61, add "the antibody or antigen binding fragment thereof" before "blocks".

Signed and Sealed this
Twenty-fifth Day of February, 2025

Coke Morgan Stewart
*Acting Director of the United States Patent and Trademark Office*